(12) United States Patent
Lu et al.

(10) Patent No.: US 12,312,413 B2
(45) Date of Patent: *May 27, 2025

(54) ANTIBODIES AND METHODS FOR MAKING AND USING THE SAME

(71) Applicants: AskGene Pharma Inc., Camarillo, CA (US); Jiangsu AoSaiKang Pharmaceutical Co., Ltd., Nanjing (CN)

(72) Inventors: Yuefeng Lu, Newbury Park, CA (US); Kurt Shanebeck, Camarillo, CA (US); Lu Li, Camarillo, CA (US); Lei Liu, Thousand Oaks, CA (US); Shiwen Zhang, Camarillo, CA (US); Lan Yang, Camarillo, CA (US); Jian-Feng Lu, Oak Park, CA (US)

(73) Assignees: AskGene Pharma Inc.; Jiangsu AoSaiKang Ph, Nanjing (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/991,775

(22) Filed: Nov. 21, 2022

(65) Prior Publication Data

US 2023/0303714 A1    Sep. 28, 2023

Related U.S. Application Data

(62) Division of application No. 16/516,223, filed on Jul. 18, 2019, now Pat. No. 11,505,618.

(60) Provisional application No. 62/792,798, filed on Jan. 15, 2019, provisional application No. 62/700,174, filed on Jul. 18, 2018.

(51) Int. Cl.
| | |
|---|---|
| C07K 16/30 | (2006.01) |
| A61K 31/282 | (2006.01) |
| A61K 31/337 | (2006.01) |
| A61K 39/00 | (2006.01) |
| A61K 39/395 | (2006.01) |
| A61K 47/68 | (2017.01) |
| A61P 35/00 | (2006.01) |
| C07K 14/54 | (2006.01) |
| C07K 14/55 | (2006.01) |
| C07K 14/765 | (2006.01) |
| C07K 16/28 | (2006.01) |

(52) U.S. Cl.
CPC ........ *C07K 16/3046* (2013.01); *A61K 31/282* (2013.01); *A61K 31/337* (2013.01); *A61K 39/39558* (2013.01); *A61K 47/6863* (2017.08); *A61P 35/00* (2018.01); *C07K 14/5443* (2013.01); *C07K 14/55* (2013.01); *C07K 14/765* (2013.01); *C07K 16/2809* (2013.01); *A61K 2039/505* (2013.01); *C07K 2317/24* (2013.01); *C07K 2317/31* (2013.01); *C07K 2317/33* (2013.01); *C07K 2317/565* (2013.01); *C07K 2317/732* (2013.01); *C07K 2317/734* (2013.01); *C07K 2317/76* (2013.01); *C07K 2317/92* (2013.01); *C07K 2319/30* (2013.01); *C07K 2319/31* (2013.01)

(58) Field of Classification Search
CPC ............ C07K 16/3046; A61K 47/6863; A61K 31/282; A61K 31/337
See application file for complete search history.

(56) References Cited

U.S. PATENT DOCUMENTS 11,505,618 B2 * 11/2022 Lu .................. C07K 14/765

OTHER PUBLICATIONS

Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Gerdes et al. Emerging understanding of multiscale tumor heterogeneity, Front. Oncol. Dec. 18, 2014 doi: 10.3389/fonc.2014.00366, pp. 1-12 (Year: 2014).*
Singh et al., Anti-claudin 18.2 antibody as new targeted therapy for advanced gastric cancer, Journal of Hematology & Oncology (2017) 10:105, Publication Date: May 12, 2017 (Year: 2017).*
Sahin et al., Claudin-18 SpliceVariant 2 Is a Pan-Cancer Target Suitable for Therapeutic Antibody Development, Clin Cancer Res. 14(23) 7624-7634, Publication Date: Dec. 1, 2008 (Year: 2008).*
Office Action from Chinese Patent Office, Application CN201980029283.3 (Publication CN112513093), dated Dec. 21, 2023, 6 pages.

* cited by examiner

*Primary Examiner* — Peter J Reddig
*Assistant Examiner* — Cheng Lu
(74) *Attorney, Agent, or Firm* — Entralta, P.C.

(57) ABSTRACT

Described and provided herein are novel antibodies for Claudin 18.2. Also described and provided are pharmaceutical compositions of the antibodies and methods of use for the treatment of cancer.

14 Claims, 22 Drawing Sheets
Specification includes a Sequence Listing.

| Load | KD (M) | kon(1/Ms) | kdis(1/s) | RMax | Full X^2 | Full R^2 |
|---|---|---|---|---|---|---|
| 5H1L3 | 2.49E-08 | 2.55E+03 | 6.35E-05 | 1.2132 | 3.0995 | 0.9951 |
| 6H1L2 | 4.03E-08 | 2.94E+03 | 1.19E-04 | 1.6376 | 7.9492 | 0.9931 |
| 26H3L3 | 2.52E-08 | 1.77E+03 | 4.46E-05 | 1.1683 | 2.2476 | 0.9887 |
| 30H10L2 | 3.08E-08 | 2.41E+03 | 7.42E-05 | 1.405 | 3.2817 | 0.9956 |
| 31H12L1 | 1.52E-07 | 1.17E+03 | 1.78E-04 | 1.0688 | 1.715 | 0.9696 |
| 33H3L1 | 1.64E-08 | 2.43E+03 | 4.00E-05 | 1.339 | 2.3685 | 0.995 |
| 42H1L11 | 3.02E-08 | 1.59E+03 | 4.78E-05 | 1.3831 | 1.2273 | 0.997 |
| 46H2L5 | 1.25E-08 | 2.32E+03 | 2.90E-05 | 1.2807 | 1.3601 | 0.9975 |
| 48H1L6 | 5.31E-08 | 1.21E+03 | 6.41E-05 | 1.1931 | 2.0349 | 0.9817 |
| 272 H1L5 | 1.31E-08 | 1.96E+03 | 2.57E-05 | 1.2669 | 1.1167 | 0.9971 |
| 312 H3L6 | 1.08E-08 | 2.11E+03 | 2.28E-05 | 1.1679 | 1.1946 | 0.9974 |
| reference | 8.69E-08 | 1.60E+03 | 1.39E-04 | 1.0563 | 2.266 | 0.9877 |

| 10 ug/ml | 5H1L3 | 6H1L2 | 26H3L3 | 42H1L11 | 46H2L5 | 48H1L6 | 215H5L3 | 272H1L5 | 32H1L1 | 100F |
|---|---|---|---|---|---|---|---|---|---|---|
| mouse-18.2 | 2130.4 | 1534.5 | 2530.2 | 1121.9 | 3491.1 | 370.2 | 427.6 | 3862.3 | 2802.7 | 38.3 |
| Human 18.2 | 479.7 | 425.1 | 488.3 | 391.5 | 553.1 | 492.2 | 443.4 | 621.8 | 738.1 | 67.1 |
| mouse-18.1 | 21.1 | 22.2 | 20.3 | 17.6 | 18.9 | 17.6 | 17.4 | 18.2 | 20.0 | 39.4 |
| Human 18.1 | 21.9 | 21.1 | 21.7 | 18.6 | 19.4 | 18.6 | 18.6 | 18.7 | 20.9 | 99.9 |
| HEK293 | 15.9 | 13.8 | 14.3 | 14.2 | 14.2 | 15.0 | 13.9 | 14.3 | 15.1 | 24.9 |

Figure 8A
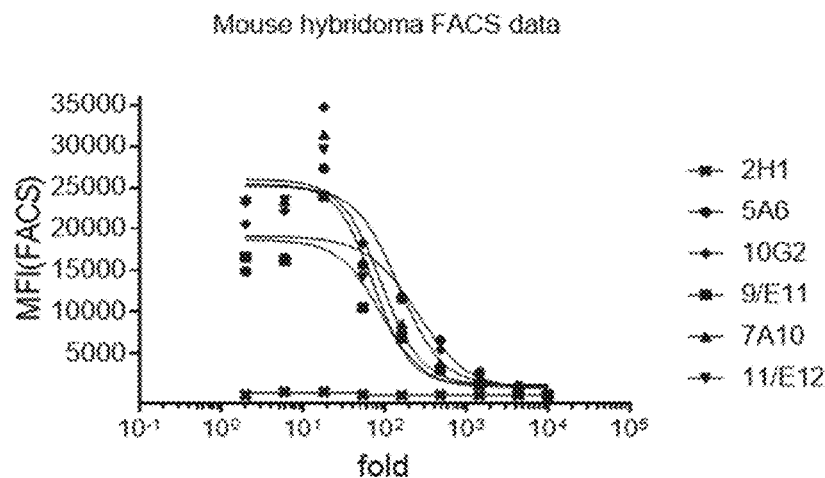
Figure 8B
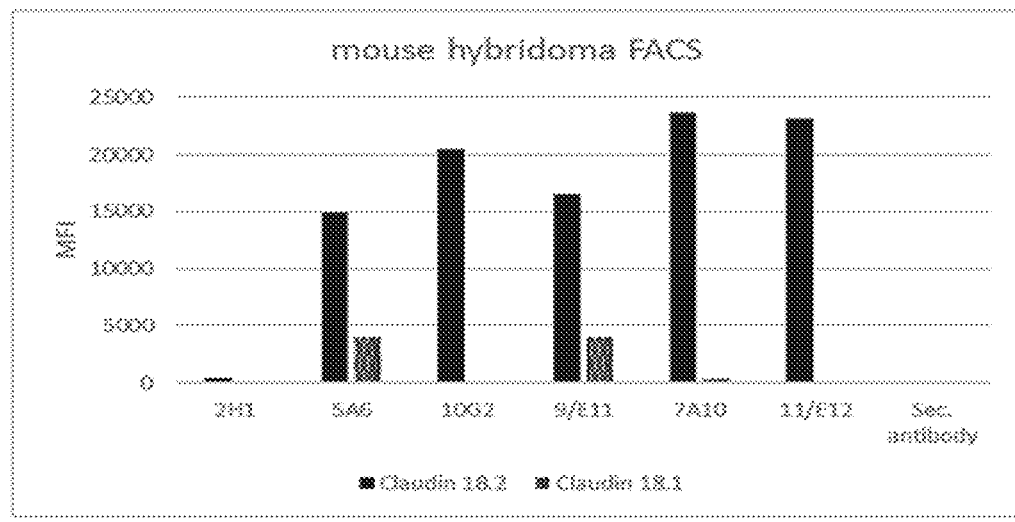
Figure 8C
|  | 2H1 | 5A6 | 10G2 | 9/E11 | 7A10 | 11/E12 | Sec. antibody |
|---|---|---|---|---|---|---|---|
| Claudin 18.2 | 425 | 14876 | 20534 | 16588 | 23630 | 23181 | 53 |
| Claudin 18.1 | 16 | 3925 | 95 | 3983 | 337 | 30 | 18 |

|  | 30B5/<br>vHA/vLG | 79C4/<br>vHD/vLF | 83G3/<br>vHA/vLG | 83G3/<br>vHE/vLG | 85H12<br>vHE/vLG | A PDL1 antibody<br>(negative control) |
|---|---|---|---|---|---|---|
| CLDN18.2 | 21.63 | 72.47 | 22.38 | 544.87 | 829.32 | 21.73 |
| CLDN18.1 | 20.88 | 22.49 | 21.85 | 21.75 | 36.91 | 30.71 |

| | EC50 |
|---|---|
| 24G4-11E12 (p6) | 29.42 |
| 67B7-10G2 | 17.13 |

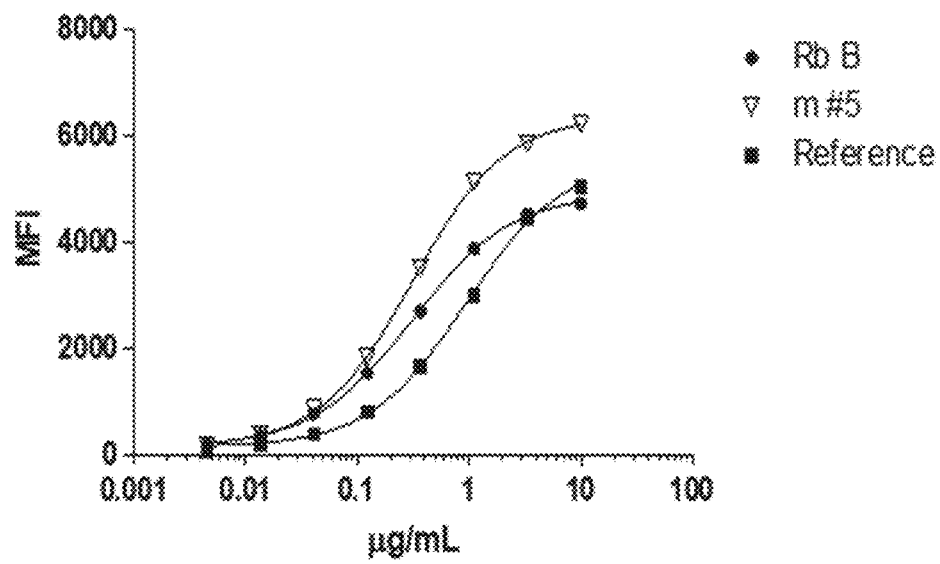
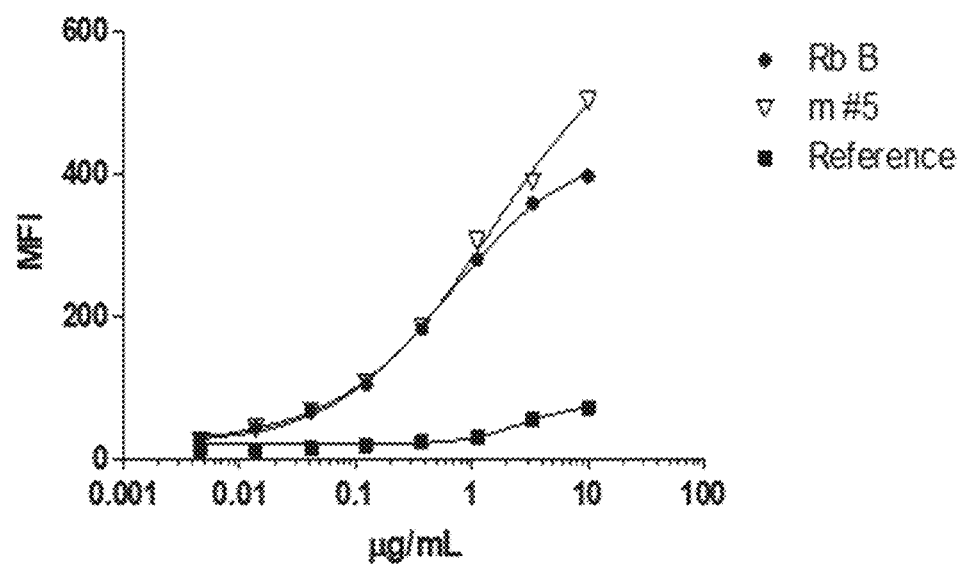

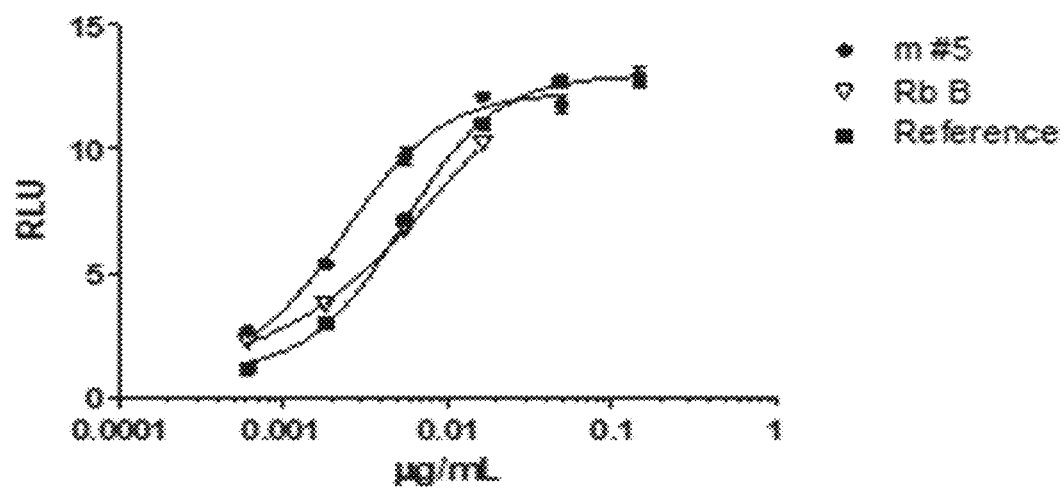
Figure 12A ADCC Reporter 18.2 Targets
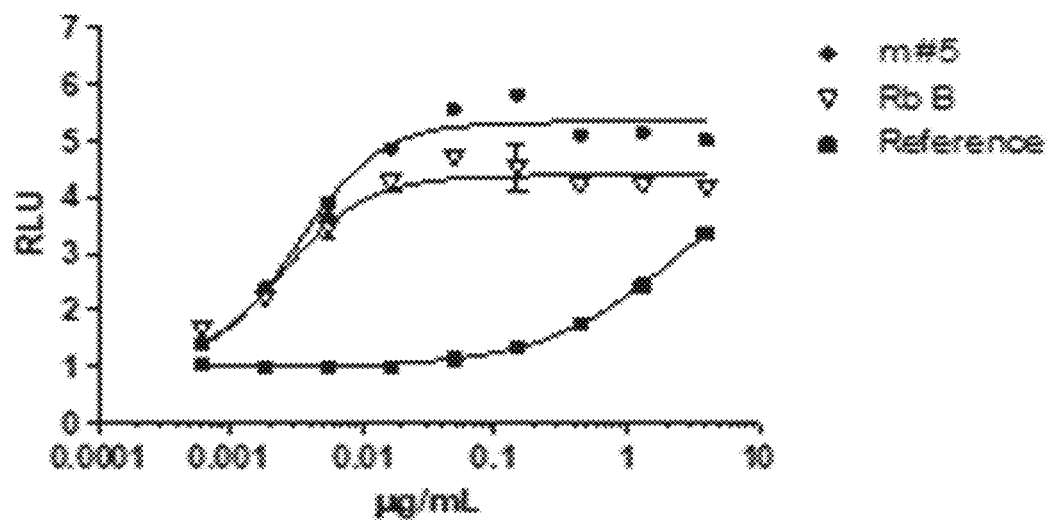
Figure 12B ADCC Reporter NUGC4 Targets

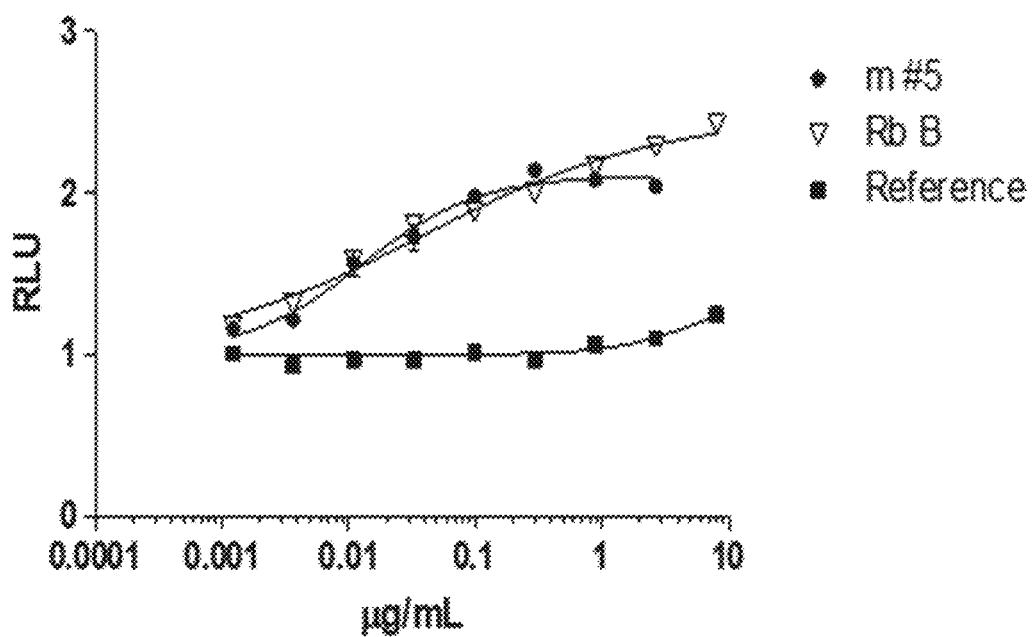

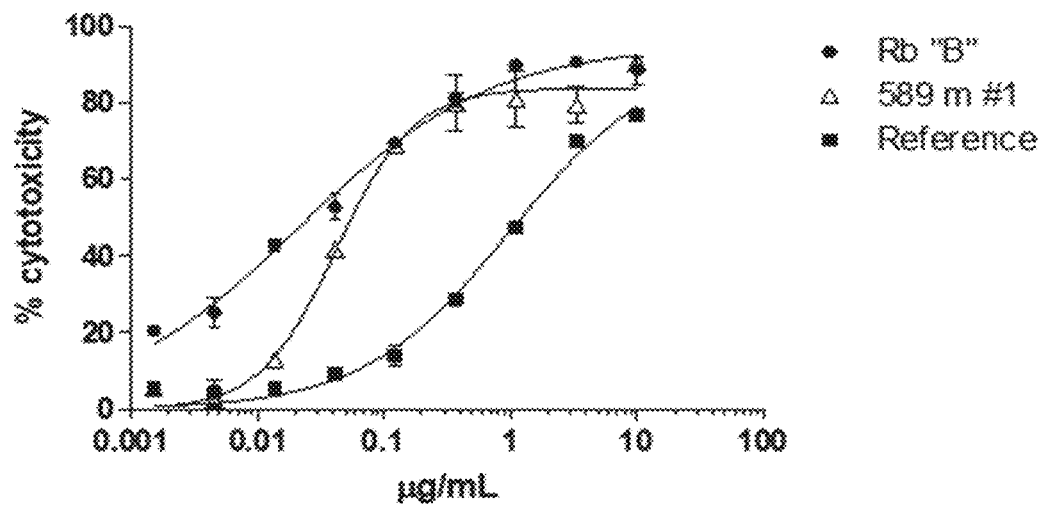
Figure 13A CDC Assay 18.2 targets
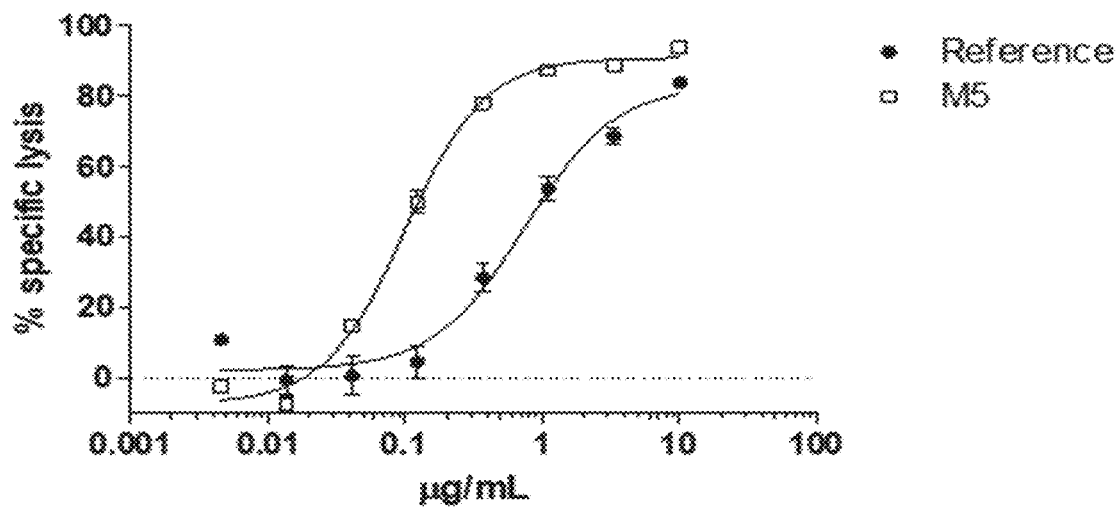
Figure 13B CDC Assay 18.2 targets
|  | Reference | M5 |
|---|---|---|
| EC50 | 0.7456 | 0.09966 |

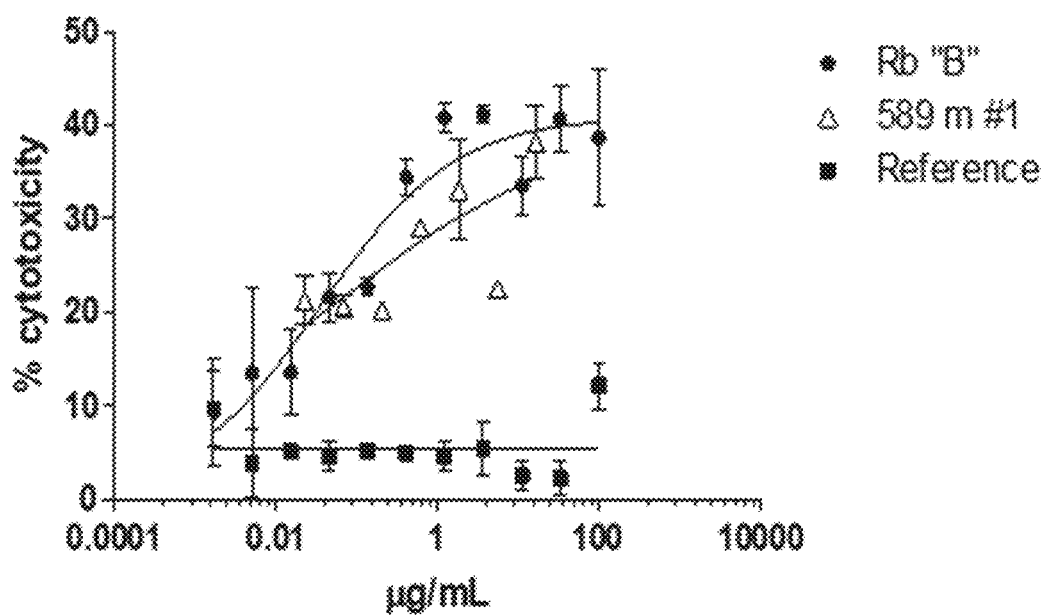

Figure 14A
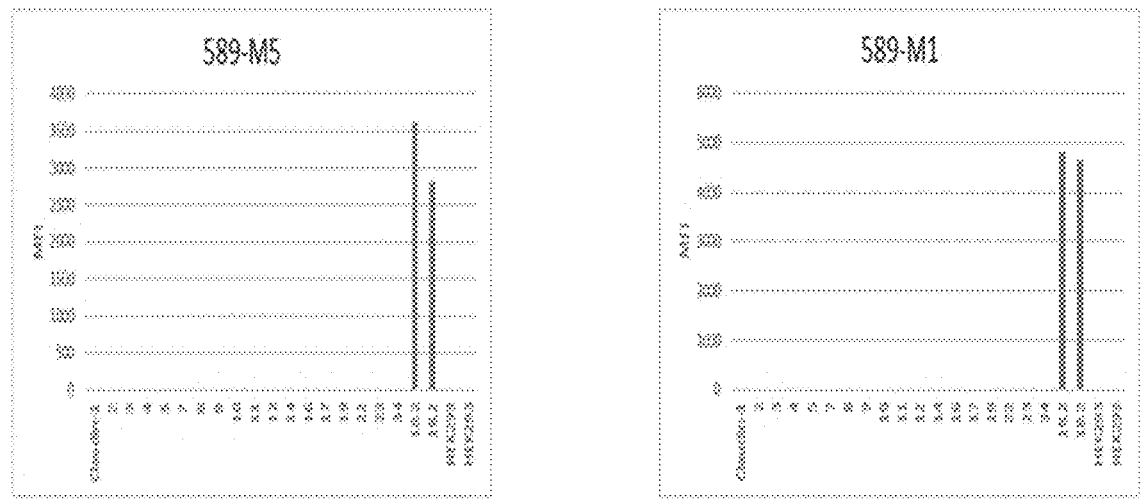
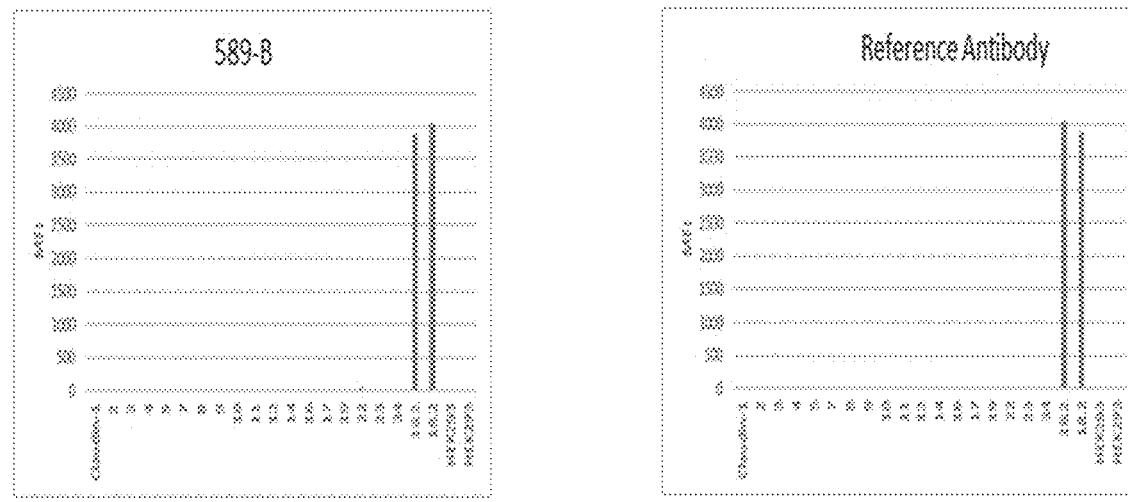

```
                        SEQUENCE LISTING

Sequence total quantity: 269
SEQ ID NO: 1            moltype = AA  length = 127
FEATURE                 Location/Qualifiers
REGION                  1..127
                        note = Heavy chain variable domain Protein Sequence
source                  1..127
                        mol_type = protein
                        organism = synthetic construct
SEQUENCE: 1
CQSLEESGGG LVKPGGTLTL TCKASGIDFS SYYYMCWVRQ APGKGLEWIA CIFNGDASTY   60
YASWAHGRFT ISKTSSTTVT LQMTGLTAAD TATYFCARSD YSVAFAAFLY PTYFTLWGPG  120
TLVTVSS                                                            127

SEQ ID NO: 2            moltype = AA  length = 121
FEATURE                 Location/Qualifiers
REGION                  1..121
                        note = Heavy chain variable domain Protein Sequence
source                  1..121
                        mol_type = protein
                        organism = synthetic construct
SEQUENCE: 2
CQSLEESGGD LVKPGASLTL TCTASGFDLS SFVYICWVRQ APGKGLEWIG CIAINGGVTY   60
YASWAKGRFT ISKTSSTTVT LQMTSLTGAD TATYFCARDD TSSNSYYNDL WGPGTLVTVS  120
S                                                                  121

SEQ ID NO: 3            moltype = AA  length = 119
FEATURE                 Location/Qualifiers
REGION                  1..119
                        note = Heavy chain variable domain Protein Sequence
source                  1..119
                        mol_type = protein
                        organism = synthetic construct
SEQUENCE: 3
CQSLEESGGG LVQPGASLTL TCKASGFSFS SSYWICWVRQ APGKGLEWIA CIYTTTSNIG   60
YASWAKGRFT ISKTSSTTVT LQMTSLTAAD TATYFCARED YDYYSFHPWG PGTLVTVSS   119

SEQ ID NO: 4            moltype = AA  length = 119
FEATURE                 Location/Qualifiers
REGION                  1..119
                        note = Heavy chain variable domain Protein Sequence
source                  1..119
                        mol_type = protein
```

```
                            organism = synthetic construct
SEQUENCE: 4
CQSLEESGGG LVQPEGSLTL TCTASGFSFS SSYWICWVRQ APGKGLEWIA CVYTTTGNIG      60
YASWAKGRFT ISVPSSTTVT LQLTSLTAAD TATYFCAREG SDIYAFHPWG PGTLVTVSS      119

SEQ ID NO: 5              moltype = AA   length = 121
FEATURE                   Location/Qualifiers
REGION                    1..121
                          note = Heavy chain variable domain Protein Sequence
source                    1..121
                          mol_type = protein
                          organism = synthetic construct
SEQUENCE: 5
QSLEESGGDL VKPGASLTLT CKASGFSFSS GYYISWIRQA PGKGLEWIAC IYAGGSGTTY      60
YATWAKGRFT VSETSSTTVT LQMTSLTAAD TATYFCARDY IGTRTYYFDF WGPGTLVTVS     120
T                                                                    121

SEQ ID NO: 6              moltype = AA   length = 122
FEATURE                   Location/Qualifiers
REGION                    1..122
                          note = Heavy chain variable domain Protein Sequence
source                    1..122
                          mol_type = protein
                          organism = synthetic construct
SEQUENCE: 6
QEQLVESGGG LVQPEGSLTL TCTASGFSFS GNYYMWWVRQ APGKGLEWIA CIHIDSGRPW      60
YASWAKGRFT ISKTSSTTVT LQMTSLTVAD TATYFCARGV SSVYWRTYFN LWGPGTLVTV     120
SS                                                                   122

SEQ ID NO: 7              moltype = AA   length = 118
FEATURE                   Location/Qualifiers
REGION                    1..118
                          note = Heavy chain variable domain Protein Sequence
source                    1..118
                          mol_type = protein
                          organism = synthetic construct
SEQUENCE: 7
QQQLVESGGG LVKPGGTLTL TCTVSGFYFN RGYWICWVRQ APGKGLEWIG CIDTGSGVPY      60
YANWAKGRFT ISKTSSTAVT LQMTSLTAAD TATYFCARNS DSIYFNLWGP GTLVTVSS      118

SEQ ID NO: 8              moltype = AA   length = 124
FEATURE                   Location/Qualifiers
REGION                    1..124
                          note = Heavy chain variable domain Protein Sequence
source                    1..124
                          mol_type = protein
                          organism = synthetic construct
SEQUENCE: 8
QEQLVESGGG LVKPGGTLTL TCTASGFSFS SGFYISWVRQ APGKGPELIS HIYTTSTTTW      60
YASWAKGRFT ISKTSSTTVT LQMTSLTAAD TATYFCARAG YVDYGYAPYD MDLWGPGTLV    120
TVSS                                                                 124

SEQ ID NO: 9              moltype = AA   length = 120
FEATURE                   Location/Qualifiers
REGION                    1..120
                          note = Heavy chain variable domain Protein Sequence
source                    1..120
                          mol_type = protein
                          organism = synthetic construct
SEQUENCE: 9
QSLEESGGGL VQPEGSLTLT CKASGFSFSY NVYMCWVRQA PGKGLEWIGC IYAVSSNTIY      60
YANWAKGRFT ISKTSSTTVT LQLPSLTAAD TATYFCATRD ANAGYSFNLW GPGTLVTVSS     120

SEQ ID NO: 10             moltype = AA   length = 124
FEATURE                   Location/Qualifiers
REGION                    1..124
                          note = Heavy chain variable domain Protein Sequence
source                    1..124
                          mol_type = protein
                          organism = synthetic construct
SEQUENCE: 10
QSLEESGGDL VQPEGSLTLT CKASGFSFSS GYYMCWVRQA PGKGLGLIAC IDAGGRGDTV      60
YASWAKGRFT ISKTSSTTVT LQLNSLTAAD TAIYFCARRG YSSISSNFGA FNPWGPGTLV    120
TVSS                                                                 124

SEQ ID NO: 11             moltype = AA   length = 122
FEATURE                   Location/Qualifiers
REGION                    1..122
                          note = Heavy chain variable domain Protein Sequence
```

```
source                  1..122
                        mol_type = protein
                        organism = synthetic construct
SEQUENCE: 11
QELKESGGRL VTPGGSLTLT CTASGFSFNS NYYMCWVRQA PGKGLEWIAC IYGGTTVNTY       60
YATWAKGRFA ISKTSSTTVT LQMTSLTAAD TATYFCARED LTAYSSYVIT LWGPGTLVTV      120
SS                                                                    122

SEQ ID NO: 12           moltype = AA   length = 118
FEATURE                 Location/Qualifiers
REGION                  1..118
                        note = Heavy chain variable domain Protein Sequence
source                  1..118
                        mol_type = protein
                        organism = synthetic construct
SEQUENCE: 12
QEQLEESGGD LVKPEGSLTL TCTVSGFSFN RGYWICWVRQ APGKGLEWIG CVDTGSGSSY       60
YANWAKGRFT ISKTSSTAVT LQMTSLTAAD TATYFCARNS DSIYFNLWGP GTLVTVSS       118

SEQ ID NO: 13           moltype = AA   length = 121
FEATURE                 Location/Qualifiers
REGION                  1..121
                        note = Heavy chain variable domain Protein Sequence
source                  1..121
                        mol_type = protein
                        organism = synthetic construct
SEQUENCE: 13
CQSLEESGGA LVKPGASLTL TCTASGFSFT SRDYICWVRQ APGKGLEWTG CIAIDGGVIY       60
YATWAKGRFT ISKTSSTTVT LQMTSLTAAD TATYFCARDD IGSNSYYNDL WGPGTLVTVS      120
S                                                                     121

SEQ ID NO: 14           moltype = AA   length = 119
FEATURE                 Location/Qualifiers
REGION                  1..119
                        note = Heavy chain variable domain Protein Sequence
source                  1..119
                        mol_type = protein
                        organism = synthetic construct
SEQUENCE: 14
QEQLEESGGG LVKPGASLTL TCTASGFSFS NNYYISWVRQ APGKGLEWIA CIYTGYSWTY       60
YASWAKGRFT ISKTSSTTVT LQMTSLTVAD TATYFCARAD SGYSGFNLWG PGTLVTVSS      119

SEQ ID NO: 15           moltype = AA   length = 119
FEATURE                 Location/Qualifiers
REGION                  1..119
                        note = Heavy chain variable domain Protein Sequence
source                  1..119
                        mol_type = protein
                        organism = synthetic construct
SEQUENCE: 15
CQSLEESGGG LVQPGASLTL TCTASGFSFS SSYWICWVRQ APGKGLEWIA CIYTTTNNIG       60
YANWAKGRFT ISKTSSTTVT LQMTSLTAAD TATYFCARED YDYYSFHPWG PGTLVTVSS      119

SEQ ID NO: 16           moltype = AA   length = 120
FEATURE                 Location/Qualifiers
REGION                  1..120
                        note = Heavy chain variable domain Protein Sequence
source                  1..120
                        mol_type = protein
                        organism = synthetic construct
SEQUENCE: 16
QQQLEESGGG LVKPGGTLTL TCTASGFTFS SYWISWVRQA PGKGLEWIAY IFTSSITFTA       60
YASWAKGRFT VSKTSSTTVT LQLTSLTAAD TATYFCARDL SSTSYYFNLW GPGTLVTVSS     120

SEQ ID NO: 17           moltype = AA   length = 122
FEATURE                 Location/Qualifiers
REGION                  1..122
                        note = Heavy chain variable domain Protein Sequence
source                  1..122
                        mol_type = protein
                        organism = synthetic construct
SEQUENCE: 17
QEQLVESGGG LVQPEGSLTL TCTASGFSFS GNYHMWVRQ APGKGLEWIA CIHTDSGRTW       60
YASWAKGRFT ISKTSSTTVT LQMTSLTVAD TATYFCARGV SSVYWRTYFN LWGPGTLVTV     120
SS                                                                    122

SEQ ID NO: 18           moltype = AA   length = 128
FEATURE                 Location/Qualifiers
REGION                  1..128
```

```
                         note = Heavy chain variable domain Protein Sequence
source                   1..128
                         mol_type = protein
                         organism = synthetic construct
SEQUENCE: 18
QEQLEESGGD LVKPEGSLTL TCTVSGFSFS NNYWICWVRQ APGKGLEWIA CIYLGSSGYT    60
YFASWARGRF TISKPSSTTV TLQMTSLTAA DTATYFCARS YYTYGYAGYI YPTYFNLWGP   120
GTLVTVSS                                                            128

SEQ ID NO: 19            moltype = AA   length = 124
FEATURE                  Location/Qualifiers
REGION                   1..124
                         note = Heavy chain variable domain Protein Sequence
source                   1..124
                         mol_type = protein
                         organism = synthetic construct
SEQUENCE: 19
QEQLVESGGG LVKPGGTLTL TCTASGFSFS SGFYISWVRQ APGKGPELIS HIYTTSTTTW    60
YASWAKGRFT ISKTSSTTVT LQMTSLTAAD TATYFCARAG YVDYGYAPYD MDLWGPGTLV   120
TVSS                                                                124

SEQ ID NO: 20            moltype = AA   length = 120
FEATURE                  Location/Qualifiers
REGION                   1..120
                         note = Heavy chain variable domain Protein Sequence
source                   1..120
                         mol_type = protein
                         organism = synthetic construct
SEQUENCE: 20
EQLVESGGGL VQPEGSLTLT CTASGFSFSS YYMCWVRQAP GKGLEWIGCI HTDSGRTWYA    60
SWAKGRFTIS KTSSTTVTLQ MTSLTVADTA TYFCARGISS VYWRTYFNLW GPGTLVTVSS   120

SEQ ID NO: 21            moltype = AA   length = 118
FEATURE                  Location/Qualifiers
REGION                   1..118
                         note = Heavy chain variable domain Protein Sequence
source                   1..118
                         mol_type = protein
                         organism = synthetic construct
SEQUENCE: 21
QQQLEESGGG LVKPGGTLTL TCTVSGFSFN AGYWICWVRQ APGKGLEWIG CIDTGSGVSY    60
YASWAKGRFT ISKTSSTAVT LQMTGLTVAD TATYFCARNT DSIYFNLWGP GTLVTVSS     118

SEQ ID NO: 22            moltype = AA   length = 124
FEATURE                  Location/Qualifiers
REGION                   1..124
                         note = Heavy chain variable domain Protein Sequence
source                   1..124
                         mol_type = protein
                         organism = synthetic construct
SEQUENCE: 22
QSLEESGGDL VQPEGSLTLT CKASGFSFSS GYYMCWVRQA PGKGLGLIAC IDAGGRGDTV    60
YASWAKGRFT ISKTSSTTVT LQLNSLTAAD TAIYFCARRG YSSISSNFGA FNPWGPGTLV   120
TVSS                                                                124

SEQ ID NO: 23            moltype = AA   length = 121
FEATURE                  Location/Qualifiers
REGION                   1..121
                         note = Heavy chain variable domain Protein Sequence
source                   1..121
                         mol_type = protein
                         organism = synthetic construct
SEQUENCE: 23
QQQLEESGGG LVKPEGSLTL TCKASGFDFT SYYYMCWVRQ APGKGLELIA YIESSSGRIW    60
YASWAKGRFT ISKTSSTTVT LQMTSLTGAD TASYFCARDI SSSGYHGFKW WGPGTLVTVS   120
S                                                                   121

SEQ ID NO: 24            moltype = AA   length = 112
FEATURE                  Location/Qualifiers
REGION                   1..112
                         note = Light chain variable domain Protein Sequence
source                   1..112
                         mol_type = protein
                         organism = synthetic construct
SEQUENCE: 24
DIVMTQTPVS VSEPVGGIVT IKCQASQSIG SNLAWYQQKP GQPPKLLIYL ASTLASGVPS    60
RFKGSGSGTE FTLTISDLEC ADAATYYCQG YYWSSSRSYG SAFGGGTEVV VV           112

SEQ ID NO: 25            moltype = AA   length = 110
```

```
FEATURE              Location/Qualifiers
REGION               1..110
                     note = Light chain variable domain Protein Sequence
source               1..110
                     mol_type = protein
                     organism = synthetic construct
SEQUENCE: 25
AYDMTQTPAS VSEPVGGAVT IKCQASQSIG SNLAWYQQKP GQPPKLLIYG ASTLASGVSS    60
RFKGSGSGTQ FTLTISGVEC ADAATYYCQQ GYTYSHADNA FGGGTEVVVV              110

SEQ ID NO: 26        moltype = AA   length = 110
FEATURE              Location/Qualifiers
REGION               1..110
                     note = Light chain variable domain Protein Sequence
source               1..110
                     mol_type = protein
                     organism = synthetic construct
SEQUENCE: 26
AYDMTQTPSS VSAAVGGTVT IKCQASQSIG TYLAWYQQKP GQPPKRLIYK ASSLPSGVSS    60
RFKGGGSGTE FTLTISGVEC ADAATYYCQQ AYTHTYLDNG FGGGTEVVVV              110

SEQ ID NO: 27        moltype = AA   length = 110
FEATURE              Location/Qualifiers
REGION               1..110
                     note = Light chain variable domain Protein Sequence
source               1..110
                     mol_type = protein
                     organism = synthetic construct
SEQUENCE: 27
AYDMTQTPAS VEVAVGGTVT IKCQASQSIS SYLSWYQQKP GQPPKLLIYK ASTLASGVSS    60
RFKGSGSGTE FTLTISGVEC ADAATYYCQQ AYTHTNLDNG FGGGTEVVVV              110

SEQ ID NO: 28        moltype = AA   length = 113
FEATURE              Location/Qualifiers
REGION               1..113
                     note = Light chain variable domain Protein Sequence
source               1..113
                     mol_type = protein
                     organism = synthetic construct
SEQUENCE: 28
AQVLTQTPSS VSAAVGGTVT INCQASQSVY KNNYLSWYQQ KPGQPPKLLI YEASKLASGV    60
PSRFSGSGSG TQFTLTISGV QCDDAATYYC AGEFTCISAD CFAFGGGTEV VVV          113

SEQ ID NO: 29        moltype = AA   length = 110
FEATURE              Location/Qualifiers
REGION               1..110
                     note = Light chain variable domain Protein Sequence
source               1..110
                     mol_type = protein
                     organism = synthetic construct
SEQUENCE: 29
DVVLTQTPSS ASEPVGGTVT IKCQASQTIG SNLAWYQQKP GQPPKLLIYG ASNLPSGVPS    60
RFSGSASGTE FTLTISGVQC DDAATYYCQS AYWLDSGDNG FGGGTEVVVV              110

SEQ ID NO: 30        moltype = AA   length = 110
FEATURE              Location/Qualifiers
REGION               1..110
                     note = Light chain variable domain Protein Sequence
source               1..110
                     mol_type = protein
                     organism = synthetic construct
SEQUENCE: 30
DIVMTQTPAS VSEPVGGTVT IKCQASQSIG GYLSWYQQKP GQPPKLLIYK ASTLASGVPS    60
RFKGSGSGTD FTLTISDLEC ADAATYYCQN YAGVSIYGAV FGGGTKVVVV              110

SEQ ID NO: 31        moltype = AA   length = 110
FEATURE              Location/Qualifiers
REGION               1..110
                     note = Light chain variable domain Protein Sequence
source               1..110
                     mol_type = protein
                     organism = synthetic construct
SEQUENCE: 31
ALVMTQTPSS VSAAVGGTVT IKCQASQSIS GYLAWYQQKP GQPPKLLIYR ASTLASGVSS    60
RFKGSGSGTE YTLTISGVEC ADAATYYCQQ GYSMYYIETS FGGGTKVVVV              110

SEQ ID NO: 32        moltype = AA   length = 109
FEATURE              Location/Qualifiers
REGION               1..109
```

```
                        note = Light chain variable domain Protein Sequence
source                  1..109
                        mol_type = protein
                        organism = synthetic construct
SEQUENCE: 32
GYDMTQTPAS VSAAVGGTIT IKCQASQSIS NWLAWYQQKP GQPPKLLIYS ASTLASGVPS    60
RFKGSGSGTQ FTLTISDMQC DDAATYYCEG GYSSGDRNVF GGGTKVVVV               109

SEQ ID NO: 33           moltype = AA  length = 110
FEATURE                 Location/Qualifiers
REGION                  1..110
                        note = Light chain variable domain Protein Sequence
source                  1..110
                        mol_type = protein
                        organism = synthetic construct
SEQUENCE: 33
AYDMTQTPAS VEVAVGGTVT IKCQASQSIS SYLAWYQQKP GQPPKQLIYG ASTLASGVSS    60
RFKGSGSGTQ FTLTISGVEC ADSATYYCQQ GYTSIYVDNA FGGGTKVVVV              110

SEQ ID NO: 34           moltype = AA  length = 110
FEATURE                 Location/Qualifiers
REGION                  1..110
                        note = Light chain variable domain Protein Sequence
source                  1..110
                        mol_type = protein
                        organism = synthetic construct
SEQUENCE: 34
AYDMTQTPAS VSEPVGGTVT IKCQASETIY RNLAWYQQKP GQPPKLLIYA ASTLASGVPS    60
RFKGSGSGTQ FTLTISDLEC ADAATYYCQQ AYTRVNIDNA FGGGTKVVVV              110

SEQ ID NO: 35           moltype = AA  length = 110
FEATURE                 Location/Qualifiers
REGION                  1..110
                        note = Light chain variable domain Protein Sequence
source                  1..110
                        mol_type = protein
                        organism = synthetic construct
SEQUENCE: 35
DIVMTQTPVS VSEPVGGTVT IKCQASQSIS SYLSWYQQKP GQPPKLLIYR ASTLASGVPS    60
RFKGSGSGTE YTLTISDLEC ADAAAYYCQN YAGVSLYGAV FGGGTEVVVV              110

SEQ ID NO: 36           moltype = AA  length = 110
FEATURE                 Location/Qualifiers
REGION                  1..110
                        note = Light chain variable domain Protein Sequence
source                  1..110
                        mol_type = protein
                        organism = synthetic construct
SEQUENCE: 36
AYDMTQTPAS VSAAVGGTVT INCQASQNIY SNLAWYQQKP GQRPKLLIYR ASTLASGVPS    60
RFRGSGSGTQ FTLTISDLEC ADAATYYCQQ GYTYIHADNA FGGGTEVVVV              110

SEQ ID NO: 37           moltype = AA  length = 111
FEATURE                 Location/Qualifiers
REGION                  1..111
                        note = Light chain variable domain Protein Sequence
source                  1..111
                        mol_type = protein
                        organism = synthetic construct
SEQUENCE: 37
DVVMTQTPAS VSEPVGGTVT IKCQASQSID SRLAWYQQKP GQPPKLLIYG ASTLASGVPS    60
RFKGSGSGTE YTLTISGVQC ADAATYYCQC SVTISTGVGG AFGGGTKVVV V            111

SEQ ID NO: 38           moltype = AA  length = 110
FEATURE                 Location/Qualifiers
REGION                  1..110
                        note = Light chain variable domain Protein Sequence
source                  1..110
                        mol_type = protein
                        organism = synthetic construct
SEQUENCE: 38
AYDMTQTPAS VSAAVGGTVT IKCQASQSIG TYLAWYQQKP GQPPKRLLYK ASSLASGVSS    60
RFKGGGSGTE FSLTISGVEC ADAATYYCQQ AYTHTYLDNG FGGGTKVVVV              110

SEQ ID NO: 39           moltype = AA  length = 110
FEATURE                 Location/Qualifiers
REGION                  1..110
                        note = Light chain variable domain Protein Sequence
source                  1..110
```

```
                    mol_type = protein
                    organism = synthetic construct
SEQUENCE: 39
AYDVTQTPAS VEVAVGGTVT IKCQASETVS YRLAWYQQKP GQPPKLLIYD ASTLASGVPS    60
RFSGSGSETE FTLTISGVEC ADAAIYYCQQ GYTRNNIDNT FGGGTKVVVV              110

SEQ ID NO: 40           moltype = AA   length = 110
FEATURE                 Location/Qualifiers
REGION                  1..110
                        note = Light chain variable domain Protein Sequence
source                  1..110
                        mol_type = protein
                        organism = synthetic construct
SEQUENCE: 40
DVVLTQTPSS ASEPVGGTVT IKCQASQTIG SNLAWYHQKP GQPPKLLIYG ASNLASGVPS    60
RFSGSASGTQ FTLTISGVQC DDAATYYCQS AYWLDSGDNG FGGGTKVVVV              110

SEQ ID NO: 41           moltype = AA   length = 113
FEATURE                 Location/Qualifiers
REGION                  1..113
                        note = Light chain variable domain Protein Sequence
source                  1..113
                        mol_type = protein
                        organism = synthetic construct
SEQUENCE: 41
NIVMTQTPSP VSAAVGGTVT IKCQASQSIS SYLAWYQQKP GQPPKLLIYK ASTLASGVSS    60
RLKGSGSGTE FTLTISDLEC ADAATYYCQT YDYSSSNSYG SNAFGGGTKV VVV          113

SEQ ID NO: 42           moltype = AA   length = 110
FEATURE                 Location/Qualifiers
REGION                  1..110
                        note = Light chain variable domain Protein Sequence
source                  1..110
                        mol_type = protein
                        organism = synthetic construct
SEQUENCE: 42
ALVMTQTPSS VSAAVGGTVT IKCQASQSIS GYLAWYQQKP GQPPKLLIYR ASTLASGVSS    60
RFKGSGSGTE YTLTISGVEC ADAATYYCQQ GYSMYYIETS FGGGTEVVVV              110

SEQ ID NO: 43           moltype = AA   length = 110
FEATURE                 Location/Qualifiers
REGION                  1..110
                        note = Light chain variable domain Protein Sequence
source                  1..110
                        mol_type = protein
                        organism = synthetic construct
SEQUENCE: 43
DVVMTQTPSS VSEPVGGTVT IRCQASQSIG SNLAWYQQKP GQPPKLLIYG ASNLASGVPS    60
RFSGSASGTQ FTLTISGVQC DDAATYYCQS AYWLDSGDNG FGGGTEVVVV              110

SEQ ID NO: 44           moltype = AA   length = 110
FEATURE                 Location/Qualifiers
REGION                  1..110
                        note = Light chain variable domain Protein Sequence
source                  1..110
                        mol_type = protein
                        organism = synthetic construct
SEQUENCE: 44
DIVMTQTPAS VEAAVGGTVT IKCQASQTIY SYLSWYQQKP GQPPKLLIYK ASTLASGVSS    60
RFKGSGSGTE FTLTISDLEC ADAAAYYCQT YAGVSIYGAA FGGGTKVVVV              110

SEQ ID NO: 45           moltype = AA   length = 110
FEATURE                 Location/Qualifiers
REGION                  1..110
                        note = Light chain variable domain Protein Sequence
source                  1..110
                        mol_type = protein
                        organism = synthetic construct
SEQUENCE: 45
AYDMTQTPAS VEVAVGGTVT IKCQASQSIS SYLAWYQQKP GQPPKQLIYG ASTLASGVSS    60
RFKGSGSGTQ FTLTISGVEC ADSATYYCQQ GYTSIYVDNA FGGGTKVVVV              110

SEQ ID NO: 46           moltype = AA   length = 110
FEATURE                 Location/Qualifiers
REGION                  1..110
                        note = Light chain variable domain Protein Sequence
source                  1..110
                        mol_type = protein
                        organism = synthetic construct
```

```
SEQUENCE: 46
AIKMTQTPAS VEAAVGGTVT IKCQASQSIS NYLAWYQQKP GQPPKLLIYR ASTLESGVPS    60
RFKGSGSGTD FTLTISDLEC ADAATYYCQQ VYSITNIDNA FGGGTEVVVV              110

SEQ ID NO: 47           moltype = AA  length = 9
FEATURE                 Location/Qualifiers
REGION                  1..9
                        note = Clone 49E05
source                  1..9
                        mol_type = protein
                        organism = synthetic construct
SEQUENCE: 47
GIDFSSYYY                                                            9

SEQ ID NO: 48           moltype = AA  length = 8
FEATURE                 Location/Qualifiers
REGION                  1..8
                        note = Clone 49E05
source                  1..8
                        mol_type = protein
                        organism = synthetic construct
SEQUENCE: 48
IFNGDAST                                                             8

SEQ ID NO: 49           moltype = AA  length = 19
FEATURE                 Location/Qualifiers
REGION                  1..19
                        note = Clone 49E05
source                  1..19
                        mol_type = protein
                        organism = synthetic construct
SEQUENCE: 49
RSDYSVAFAA FLYPTYFTL                                                 19

SEQ ID NO: 50           moltype = AA  length = 6
FEATURE                 Location/Qualifiers
REGION                  1..6
                        note = Clone 49E05
source                  1..6
                        mol_type = protein
                        organism = synthetic construct
SEQUENCE: 50
QSIGSN                                                               6

SEQ ID NO: 51           moltype =     length =
SEQUENCE: 51
000

SEQ ID NO: 52           moltype = AA  length = 14
FEATURE                 Location/Qualifiers
REGION                  1..14
                        note = Clone 49E12
source                  1..14
                        mol_type = protein
                        organism = synthetic construct
SEQUENCE: 52
QGYYWSSSRS YGSA                                                      14

SEQ ID NO: 53           moltype = AA  length = 9
FEATURE                 Location/Qualifiers
REGION                  1..9
                        note = Clone 49E12
source                  1..9
                        mol_type = protein
                        organism = synthetic construct
SEQUENCE: 53
GFDLSSFVY                                                            9

SEQ ID NO: 54           moltype = AA  length = 7
FEATURE                 Location/Qualifiers
REGION                  1..7
                        note = Clone 49E12
source                  1..7
                        mol_type = protein
                        organism = synthetic construct
SEQUENCE: 54
IAINGGV                                                              7

SEQ ID NO: 55           moltype = AA  length = 14
```

```
FEATURE                 Location/Qualifiers
REGION                  1..14
                        note = Clone 49E12
source                  1..14
                        mol_type = protein
                        organism = synthetic construct
SEQUENCE: 55
ARDDTSSNSY YNDL                                                          14

SEQ ID NO: 56           moltype = AA  length = 6
FEATURE                 Location/Qualifiers
REGION                  1..6
                        note = Clone 49E12
source                  1..6
                        mol_type = protein
                        organism = synthetic construct
SEQUENCE: 56
QSIGSN                                                                    6

SEQ ID NO: 57           moltype =     length =
SEQUENCE: 57
000

SEQ ID NO: 58           moltype = AA  length = 12
FEATURE                 Location/Qualifiers
REGION                  1..12
                        note = Clone 49E12
source                  1..12
                        mol_type = protein
                        organism = synthetic construct
SEQUENCE: 58
QQGYTYSHAD NA                                                            12

SEQ ID NO: 59           moltype = AA  length = 9
FEATURE                 Location/Qualifiers
REGION                  1..9
                        note = Clone 50H08
source                  1..9
                        mol_type = protein
                        organism = synthetic construct
SEQUENCE: 59
GFSFSSSYW                                                                 9

SEQ ID NO: 60           moltype = AA  length = 7
FEATURE                 Location/Qualifiers
REGION                  1..7
                        note = Clone 50H08
source                  1..7
                        mol_type = protein
                        organism = synthetic construct
SEQUENCE: 60
IYTTTSN                                                                   7

SEQ ID NO: 61           moltype = AA  length = 12
FEATURE                 Location/Qualifiers
REGION                  1..12
                        note = Clone 50H08
source                  1..12
                        mol_type = protein
                        organism = synthetic construct
SEQUENCE: 61
AREDYDYYSF HP                                                            12

SEQ ID NO: 62           moltype = AA  length = 6
FEATURE                 Location/Qualifiers
REGION                  1..6
                        note = Clone 50H08
source                  1..6
                        mol_type = protein
                        organism = synthetic construct
SEQUENCE: 62
QSIGTY                                                                    6

SEQ ID NO: 63           moltype =     length =
SEQUENCE: 63
000

SEQ ID NO: 64           moltype = AA  length = 12
FEATURE                 Location/Qualifiers
```

```
REGION                    1..12
                          note = Clone 50H08
source                    1..12
                          mol_type = protein
                          organism = synthetic construct
SEQUENCE: 64
QQAYTHTYLD NG                                                                    12

SEQ ID NO: 65             moltype = AA  length = 9
FEATURE                   Location/Qualifiers
REGION                    1..9
                          note = Clone 52E07
source                    1..9
                          mol_type = protein
                          organism = synthetic construct
SEQUENCE: 65
GFSFSSSYW                                                                         9

SEQ ID NO: 66             moltype = AA  length = 7
FEATURE                   Location/Qualifiers
REGION                    1..7
                          note = Clone 52E07
source                    1..7
                          mol_type = protein
                          organism = synthetic construct
SEQUENCE: 66
VYTTTGN                                                                           7

SEQ ID NO: 67             moltype = AA  length = 12
FEATURE                   Location/Qualifiers
REGION                    1..12
                          note = Clone 52E07
source                    1..12
                          mol_type = protein
                          organism = synthetic construct
SEQUENCE: 67
AREGSDIYAF HP                                                                    12

SEQ ID NO: 68             moltype = AA  length = 6
FEATURE                   Location/Qualifiers
REGION                    1..6
                          note = Clone 52E07
source                    1..6
                          mol_type = protein
                          organism = synthetic construct
SEQUENCE: 68
QSISSY                                                                            6

SEQ ID NO: 69             moltype =    length =
SEQUENCE: 69
000

SEQ ID NO: 70             moltype = AA  length = 12
FEATURE                   Location/Qualifiers
REGION                    1..12
                          note = Clone 52E07
source                    1..12
                          mol_type = protein
                          organism = synthetic construct
SEQUENCE: 70
QQAYTHTNLD NG                                                                    12

SEQ ID NO: 71             moltype = AA  length = 9
FEATURE                   Location/Qualifiers
REGION                    1..9
                          note = Clone 52G02
source                    1..9
                          mol_type = protein
                          organism = synthetic construct
SEQUENCE: 71
GFSFSSGYY                                                                         9

SEQ ID NO: 72             moltype = AA  length = 9
FEATURE                   Location/Qualifiers
REGION                    1..9
                          note = Clone 52G02
source                    1..9
                          mol_type = protein
                          organism = synthetic construct
```

| | | |
|---|---|---|
| SEQUENCE: 72 | | |
| IYAGGSGTT | | 9 |
| | | |
| SEQ ID NO: 73 | moltype = AA  length = 14 | |
| FEATURE | Location/Qualifiers | |
| REGION | 1..14 | |
| | note = Clone 52G02 | |
| source | 1..14 | |
| | mol_type = protein | |
| | organism = synthetic construct | |
| SEQUENCE: 73 | | |
| ARDYIGTRTY YFDF | | 14 |
| | | |
| SEQ ID NO: 74 | moltype = AA  length = 8 | |
| FEATURE | Location/Qualifiers | |
| REGION | 1..8 | |
| | note = Clone 52G02 | |
| source | 1..8 | |
| | mol_type = protein | |
| | organism = synthetic construct | |
| SEQUENCE: 74 | | |
| QSVYKNNY | | 8 |
| | | |
| SEQ ID NO: 75 | moltype =   length = | |
| SEQUENCE: 75 | | |
| 000 | | |
| | | |
| SEQ ID NO: 76 | moltype = AA  length = 13 | |
| FEATURE | Location/Qualifiers | |
| REGION | 1..13 | |
| | note = Clone 52G02 | |
| source | 1..13 | |
| | mol_type = protein | |
| | organism = synthetic construct | |
| SEQUENCE: 76 | | |
| AGEFTCISAD CFA | | 13 |
| | | |
| SEQ ID NO: 77 | moltype = AA  length = 9 | |
| FEATURE | Location/Qualifiers | |
| REGION | 1..9 | |
| | note = Clone 54B08 | |
| source | 1..9 | |
| | mol_type = protein | |
| | organism = synthetic construct | |
| SEQUENCE: 77 | | |
| GFSFSGNYY | | 9 |
| | | |
| SEQ ID NO: 78 | moltype = AA  length = 8 | |
| FEATURE | Location/Qualifiers | |
| REGION | 1..8 | |
| | note = Clone 54B08 | |
| source | 1..8 | |
| | mol_type = protein | |
| | organism = synthetic construct | |
| SEQUENCE: 78 | | |
| IHIDSGRP | | 8 |
| | | |
| SEQ ID NO: 79 | moltype = AA  length = 14 | |
| FEATURE | Location/Qualifiers | |
| REGION | 1..14 | |
| | note = Clone 54B08 | |
| source | 1..14 | |
| | mol_type = protein | |
| | organism = synthetic construct | |
| SEQUENCE: 79 | | |
| RGVSSVYWRT YFNL | | 14 |
| | | |
| SEQ ID NO: 80 | moltype = AA  length = 6 | |
| FEATURE | Location/Qualifiers | |
| REGION | 1..6 | |
| | note = Clone 54B08 | |
| source | 1..6 | |
| | mol_type = protein | |
| | organism = synthetic construct | |
| SEQUENCE: 80 | | |
| QTIGSN | | 6 |
| | | |
| SEQ ID NO: 81 | moltype =   length = | |
| SEQUENCE: 81 | | |

-continued

```
000

SEQ ID NO: 82          moltype = AA   length = 12
FEATURE                Location/Qualifiers
REGION                 1..12
                       note = Clone 54B08
source                 1..12
                       mol_type = protein
                       organism = synthetic construct
SEQUENCE: 82
QSAYWLDSGD NG                                                                12

SEQ ID NO: 83          moltype = AA   length = 9
FEATURE                Location/Qualifiers
REGION                 1..9
                       note = Clone 54C02
source                 1..9
                       mol_type = protein
                       organism = synthetic construct
SEQUENCE: 83
GFYFNRGYW                                                                     9

SEQ ID NO: 84          moltype = AA   length = 7
FEATURE                Location/Qualifiers
REGION                 1..7
                       note = Clone 54C02
source                 1..7
                       mol_type = protein
                       organism = synthetic construct
SEQUENCE: 84
IDTGSGV                                                                       7

SEQ ID NO: 85          moltype = AA   length = 11
FEATURE                Location/Qualifiers
REGION                 1..11
                       note = Clone 54C02
source                 1..11
                       mol_type = protein
                       organism = synthetic construct
SEQUENCE: 85
ARNSDSIYFN L                                                                 11

SEQ ID NO: 86          moltype = AA   length = 6
FEATURE                Location/Qualifiers
REGION                 1..6
                       note = Clone 54C02
source                 1..6
                       mol_type = protein
                       organism = synthetic construct
SEQUENCE: 86
QSIGGY                                                                        6

SEQ ID NO: 87          moltype =     length =
SEQUENCE: 87
000

SEQ ID NO: 88          moltype = AA   length = 12
FEATURE                Location/Qualifiers
REGION                 1..12
                       note = Clone 54C02
source                 1..12
                       mol_type = protein
                       organism = synthetic construct
SEQUENCE: 88
QNYAGVSIYG AV                                                                12

SEQ ID NO: 89          moltype = AA   length = 9
FEATURE                Location/Qualifiers
REGION                 1..9
                       note = Clone 59A08
source                 1..9
                       mol_type = protein
                       organism = synthetic construct
SEQUENCE: 89
GFSFSSGFY                                                                     9

SEQ ID NO: 90          moltype = AA   length = 8
FEATURE                Location/Qualifiers
REGION                 1..8
```

```
                              note = Clone 59A08
source                        1..8
                              mol_type = protein
                              organism = synthetic construct
SEQUENCE: 90
IYTTSTTT                                                                  8

SEQ ID NO: 91        moltype = AA  length = 16
FEATURE              Location/Qualifiers
REGION               1..16
                     note = Clone 59A08
source               1..16
                     mol_type = protein
                     organism = synthetic construct
SEQUENCE: 91
RAGYVDYGYA PYDMDL                                                        16

SEQ ID NO: 92        moltype = AA  length = 6
FEATURE              Location/Qualifiers
REGION               1..6
                     note = Clone 59A08
source               1..6
                     mol_type = protein
                     organism = synthetic construct
SEQUENCE: 92
QSISGY                                                                    6

SEQ ID NO: 93        moltype =     length =
SEQUENCE: 93
000

SEQ ID NO: 94        moltype = AA  length = 12
FEATURE              Location/Qualifiers
REGION               1..12
                     note = Clone 59A08
source               1..12
                     mol_type = protein
                     organism = synthetic construct
SEQUENCE: 94
QQGYSMYYIE TS                                                            12

SEQ ID NO: 95        moltype = AA  length = 9
FEATURE              Location/Qualifiers
REGION               1..9
                     note = Clone 59E07
source               1..9
                     mol_type = protein
                     organism = synthetic construct
SEQUENCE: 95
GFSFSYNVY                                                                 9

SEQ ID NO: 96        moltype = AA  length = 9
FEATURE              Location/Qualifiers
REGION               1..9
                     note = Clone 59E07
source               1..9
                     mol_type = protein
                     organism = synthetic construct
SEQUENCE: 96
IYAVSSNTI                                                                 9

SEQ ID NO: 97        moltype = AA  length = 13
FEATURE              Location/Qualifiers
REGION               1..13
                     note = Clone 59E07
source               1..13
                     mol_type = protein
                     organism = synthetic construct
SEQUENCE: 97
ATRDANAGYS FNL                                                           13

SEQ ID NO: 98        moltype = AA  length = 6
FEATURE              Location/Qualifiers
REGION               1..6
                     note = Clone 59E07
source               1..6
                     mol_type = protein
                     organism = synthetic construct
SEQUENCE: 98
```

QSISNW 6

SEQ ID NO: 99    moltype =   length =
SEQUENCE: 99
000

SEQ ID NO: 100   moltype = AA   length = 11
FEATURE          Location/Qualifiers
REGION           1..11
                 note = Clone 59E07
source           1..11
                 mol_type = protein
                 organism = synthetic construct
SEQUENCE: 100
EGGYSSGDRN V 11

SEQ ID NO: 101   moltype = AA   length = 9
FEATURE          Location/Qualifiers
REGION           1..9
                 note = Clone 59F10
source           1..9
                 mol_type = protein
                 organism = synthetic construct
SEQUENCE: 101
GFSFSSGYY 9

SEQ ID NO: 102   moltype = AA   length = 9
FEATURE          Location/Qualifiers
REGION           1..9
                 note = Clone 59F10
source           1..9
                 mol_type = protein
                 organism = synthetic construct
SEQUENCE: 102
IDAGGRGDT 9

SEQ ID NO: 103   moltype = AA   length = 17
FEATURE          Location/Qualifiers
REGION           1..17
                 note = Clone 59F10
source           1..17
                 mol_type = protein
                 organism = synthetic construct
SEQUENCE: 103
ARRGYSSISS NFGAFNP 17

SEQ ID NO: 104   moltype = AA   length = 6
FEATURE          Location/Qualifiers
REGION           1..6
                 note = Clone 59F10
source           1..6
                 mol_type = protein
                 organism = synthetic construct
SEQUENCE: 104
QSISSY 6

SEQ ID NO: 105   moltype =   length =
SEQUENCE: 105
000

SEQ ID NO: 106   moltype = AA   length = 12
FEATURE          Location/Qualifiers
REGION           1..12
                 note = Clone 59F10
source           1..12
                 mol_type = protein
                 organism = synthetic construct
SEQUENCE: 106
QQGYTSIYVD NA 12

SEQ ID NO: 107   moltype = AA   length = 9
FEATURE          Location/Qualifiers
REGION           1..9
                 note = Clone 59G03
source           1..9
                 mol_type = protein
                 organism = synthetic construct
SEQUENCE: 107
GFSFNSYY 9

```
SEQ ID NO: 108         moltype = AA  length = 9
FEATURE                Location/Qualifiers
REGION                 1..9
                       note = Clone 59G03
source                 1..9
                       mol_type = protein
                       organism = synthetic construct
SEQUENCE: 108
IYGGTTVNT                                                              9

SEQ ID NO: 109         moltype = AA  length = 15
FEATURE                Location/Qualifiers
REGION                 1..15
                       note = Clone 59G03
source                 1..15
                       mol_type = protein
                       organism = synthetic construct
SEQUENCE: 109
AREDLTAYSS YVITL                                                      15

SEQ ID NO: 110         moltype = AA  length = 6
FEATURE                Location/Qualifiers
REGION                 1..6
                       note = Clone 59G03
source                 1..6
                       mol_type = protein
                       organism = synthetic construct
SEQUENCE: 110
ETIYRN                                                                 6

SEQ ID NO: 111         moltype =    length =
SEQUENCE: 111
000

SEQ ID NO: 112         moltype = AA  length = 12
FEATURE                Location/Qualifiers
REGION                 1..12
                       note = Clone 59G03
source                 1..12
                       mol_type = protein
                       organism = synthetic construct
SEQUENCE: 112
QQAYTRVNID NA                                                         12

SEQ ID NO: 113         moltype = AA  length = 9
FEATURE                Location/Qualifiers
REGION                 1..9
                       note = Clone 77B06
source                 1..9
                       mol_type = protein
                       organism = synthetic construct
SEQUENCE: 113
GFSFNRGYW                                                              9

SEQ ID NO: 114         moltype = AA  length = 7
FEATURE                Location/Qualifiers
REGION                 1..7
                       note = Clone 77B06
source                 1..7
                       mol_type = protein
                       organism = synthetic construct
SEQUENCE: 114
VDTGSGS                                                                7

SEQ ID NO: 115         moltype = AA  length = 11
FEATURE                Location/Qualifiers
REGION                 1..11
                       note = Clone 77B06
source                 1..11
                       mol_type = protein
                       organism = synthetic construct
SEQUENCE: 115
ARNSDSIYFN L                                                          11

SEQ ID NO: 116         moltype = AA  length = 6
FEATURE                Location/Qualifiers
REGION                 1..6
                       note = Clone 77B06
```

```
source                  1..6
                        mol_type = protein
                        organism = synthetic construct
SEQUENCE: 116
QSISSY                                                                    6

SEQ ID NO: 117          moltype =    length =
SEQUENCE: 117
000

SEQ ID NO: 118          moltype = AA   length = 12
FEATURE                 Location/Qualifiers
REGION                  1..12
                        note = Clone 77B06
source                  1..12
                        mol_type = protein
                        organism = synthetic construct
SEQUENCE: 118
QNYAGVSLYG AV                                                            12

SEQ ID NO: 119          moltype = AA   length = 9
FEATURE                 Location/Qualifiers
REGION                  1..9
                        note = Clone 80D08
source                  1..9
                        mol_type = protein
                        organism = synthetic construct
SEQUENCE: 119
GFSFTSRDY                                                                 9

SEQ ID NO: 120          moltype = AA   length = 7
FEATURE                 Location/Qualifiers
REGION                  1..7
                        note = Clone 80D08
source                  1..7
                        mol_type = protein
                        organism = synthetic construct
SEQUENCE: 120
IAIDGGV                                                                   7

SEQ ID NO: 121          moltype = AA   length = 14
FEATURE                 Location/Qualifiers
REGION                  1..14
                        note = Clone 80D08
source                  1..14
                        mol_type = protein
                        organism = synthetic construct
SEQUENCE: 121
ARDDIGSNSY YNDL                                                          14

SEQ ID NO: 122          moltype = AA   length = 6
FEATURE                 Location/Qualifiers
REGION                  1..6
                        note = Clone 80D08
source                  1..6
                        mol_type = protein
                        organism = synthetic construct
SEQUENCE: 122
QNIYSN                                                                    6

SEQ ID NO: 123          moltype =    length =
SEQUENCE: 123
000

SEQ ID NO: 124          moltype = AA   length = 12
FEATURE                 Location/Qualifiers
REGION                  1..12
                        note = Clone 80D08
source                  1..12
                        mol_type = protein
                        organism = synthetic construct
SEQUENCE: 124
QQGYTYIHAD NA                                                            12

SEQ ID NO: 125          moltype = AA   length = 9
FEATURE                 Location/Qualifiers
REGION                  1..9
                        note = Clone 80G08
source                  1..9
```

```
                        mol_type = protein
                        organism = synthetic construct
SEQUENCE: 125
GFSFSNNYY                                                                        9

SEQ ID NO: 126          moltype = AA   length = 7
FEATURE                 Location/Qualifiers
REGION                  1..7
                        note = Clone 80G08
source                  1..7
                        mol_type = protein
                        organism = synthetic construct
SEQUENCE: 126
IYTGYSW                                                                          7

SEQ ID NO: 127          moltype = AA   length = 12
FEATURE                 Location/Qualifiers
REGION                  1..12
                        note = Clone 80G08
source                  1..12
                        mol_type = protein
                        organism = synthetic construct
SEQUENCE: 127
ARADSGYSGF NL                                                                   12

SEQ ID NO: 128          moltype = AA   length = 6
FEATURE                 Location/Qualifiers
REGION                  1..6
                        note = Clone 80G08
source                  1..6
                        mol_type = protein
                        organism = synthetic construct
SEQUENCE: 128
QSIDSR                                                                           6

SEQ ID NO: 129          moltype =   length =
SEQUENCE: 129
000

SEQ ID NO: 130          moltype = AA   length = 13
FEATURE                 Location/Qualifiers
REGION                  1..13
                        note = Clone 80G08
source                  1..13
                        mol_type = protein
                        organism = synthetic construct
SEQUENCE: 130
QCSVTISTGV GGA                                                                  13

SEQ ID NO: 131          moltype = AA   length = 9
FEATURE                 Location/Qualifiers
REGION                  1..9
                        note = Clone 81E11
source                  1..9
                        mol_type = protein
                        organism = synthetic construct
SEQUENCE: 131
GFSFSSSYW                                                                        9

SEQ ID NO: 132          moltype = AA   length = 7
FEATURE                 Location/Qualifiers
REGION                  1..7
                        note = Clone 81E11
source                  1..7
                        mol_type = protein
                        organism = synthetic construct
SEQUENCE: 132
IYTTTNN                                                                          7

SEQ ID NO: 133          moltype = AA   length = 12
FEATURE                 Location/Qualifiers
REGION                  1..12
                        note = Clone 81E11
source                  1..12
                        mol_type = protein
                        organism = synthetic construct
SEQUENCE: 133
AREDYDYYSF HP                                                                   12
```

```
SEQ ID NO: 134          moltype = AA  length = 6
FEATURE                 Location/Qualifiers
REGION                  1..6
                        note = Clone 81E11
source                  1..6
                        mol_type = protein
                        organism = synthetic construct
SEQUENCE: 134
QSIGTY                                                                    6

SEQ ID NO: 135          moltype =     length =
SEQUENCE: 135
000

SEQ ID NO: 136          moltype = AA  length = 12
FEATURE                 Location/Qualifiers
REGION                  1..12
                        note = Clone 81E11
source                  1..12
                        mol_type = protein
                        organism = synthetic construct
SEQUENCE: 136
QQAYTHTYLD NG                                                            12

SEQ ID NO: 137          moltype = AA  length = 8
FEATURE                 Location/Qualifiers
REGION                  1..8
                        note = Clone 82C08
source                  1..8
                        mol_type = protein
                        organism = synthetic construct
SEQUENCE: 137
GFTFSSYW                                                                  8

SEQ ID NO: 138          moltype = AA  length = 8
FEATURE                 Location/Qualifiers
REGION                  1..8
                        note = Clone 82C08
source                  1..8
                        mol_type = protein
                        organism = synthetic construct
SEQUENCE: 138
IFTSSITF                                                                  8

SEQ ID NO: 139          moltype = AA  length = 13
FEATURE                 Location/Qualifiers
REGION                  1..13
                        note = Clone 82C08
source                  1..13
                        mol_type = protein
                        organism = synthetic construct
SEQUENCE: 139
ARDLSSTSYY FNL                                                           13

SEQ ID NO: 140          moltype = AA  length = 6
FEATURE                 Location/Qualifiers
REGION                  1..6
                        note = Clone 82C08
source                  1..6
                        mol_type = protein
                        organism = synthetic construct
SEQUENCE: 140
ETVSYR                                                                    6

SEQ ID NO: 141          moltype =     length =
SEQUENCE: 141
000

SEQ ID NO: 142          moltype = AA  length = 12
FEATURE                 Location/Qualifiers
REGION                  1..12
                        note = Clone 82C08
source                  1..12
                        mol_type = protein
                        organism = synthetic construct
SEQUENCE: 142
QQGYTRNNID NT                                                            12

SEQ ID NO: 143          moltype = AA  length = 9
```

```
FEATURE                 Location/Qualifiers
REGION                  1..9
                        note = Clone 82F02
source                  1..9
                        mol_type = protein
                        organism = synthetic construct
SEQUENCE: 143
GFSFSGNYH                                                                9

SEQ ID NO: 144          moltype = AA  length = 8
FEATURE                 Location/Qualifiers
REGION                  1..8
                        note = Clone 82F02
source                  1..8
                        mol_type = protein
                        organism = synthetic construct
SEQUENCE: 144
IHTDSGRT                                                                 8

SEQ ID NO: 145          moltype = AA  length = 14
FEATURE                 Location/Qualifiers
REGION                  1..14
                        note = Clone 82F02
source                  1..14
                        mol_type = protein
                        organism = synthetic construct
SEQUENCE: 145
RGVSSVYWRT YFNL                                                         14

SEQ ID NO: 146          moltype = AA  length = 6
FEATURE                 Location/Qualifiers
REGION                  1..6
                        note = Clone 82F02
source                  1..6
                        mol_type = protein
                        organism = synthetic construct
SEQUENCE: 146
QTIGSN                                                                   6

SEQ ID NO: 147          moltype =     length =
SEQUENCE: 147
000

SEQ ID NO: 148          moltype = AA  length = 12
FEATURE                 Location/Qualifiers
REGION                  1..12
                        note = Clone 82F02
source                  1..12
                        mol_type = protein
                        organism = synthetic construct
SEQUENCE: 148
QSAYWLDSGD NG                                                           12

SEQ ID NO: 149          moltype = AA  length = 9
FEATURE                 Location/Qualifiers
REGION                  1..9
                        note = Clone 99A09
source                  1..9
                        mol_type = protein
                        organism = synthetic construct
SEQUENCE: 149
GFSFSNNYW                                                                9

SEQ ID NO: 150          moltype = AA  length = 9
FEATURE                 Location/Qualifiers
REGION                  1..9
                        note = Clone 99A09
source                  1..9
                        mol_type = protein
                        organism = synthetic construct
SEQUENCE: 150
IYLGSSGYT                                                                9

SEQ ID NO: 151          moltype = AA  length = 20
FEATURE                 Location/Qualifiers
REGION                  1..20
                        note = Clone 99A09
source                  1..20
                        mol_type = protein
```

```
                          organism = synthetic construct
SEQUENCE: 151
ARSYYTYGYA GYIYPTYFNL                                                    20

SEQ ID NO: 152           moltype = AA   length = 6
FEATURE                  Location/Qualifiers
REGION                   1..6
                         note = Clone 99A09
source                   1..6
                         mol_type = protein
                         organism = synthetic construct
SEQUENCE: 152
QSISSY                                                                    6

SEQ ID NO: 153           moltype =    length =
SEQUENCE: 153
000

SEQ ID NO: 154           moltype = AA   length = 15
FEATURE                  Location/Qualifiers
REGION                   1..15
                         note = Clone 99A09
source                   1..15
                         mol_type = protein
                         organism = synthetic construct
SEQUENCE: 154
QTYDYSSSNS YGSNA                                                         15

SEQ ID NO: 155           moltype = AA   length = 9
FEATURE                  Location/Qualifiers
REGION                   1..9
                         note = Clone SD215
source                   1..9
                         mol_type = protein
                         organism = synthetic construct
SEQUENCE: 155
GFSFSSGFY                                                                 9

SEQ ID NO: 156           moltype = AA   length = 8
FEATURE                  Location/Qualifiers
REGION                   1..8
                         note = Clone SD215
source                   1..8
                         mol_type = protein
                         organism = synthetic construct
SEQUENCE: 156
IYTTSTTT                                                                  8

SEQ ID NO: 157           moltype = AA   length = 16
FEATURE                  Location/Qualifiers
REGION                   1..16
                         note = Clone SD215
source                   1..16
                         mol_type = protein
                         organism = synthetic construct
SEQUENCE: 157
RAGYVDYGYA PYDMDL                                                        16

SEQ ID NO: 158           moltype = AA   length = 6
FEATURE                  Location/Qualifiers
REGION                   1..6
                         note = Clone SD215
source                   1..6
                         mol_type = protein
                         organism = synthetic construct
SEQUENCE: 158
QSISGY                                                                    6

SEQ ID NO: 159           moltype =    length =
SEQUENCE: 159
000

SEQ ID NO: 160           moltype = AA   length = 12
FEATURE                  Location/Qualifiers
REGION                   1..12
                         note = Clone SD215
source                   1..12
                         mol_type = protein
                         organism = synthetic construct
```

```
SEQUENCE: 160
QQGYSMYYIE TS                                                           12

SEQ ID NO: 161          moltype = AA  length = 8
FEATURE                 Location/Qualifiers
REGION                  1..8
                        note = Clone SD232
source                  1..8
                        mol_type = protein
                        organism = synthetic construct
SEQUENCE: 161
GFSFSSYY                                                                8

SEQ ID NO: 162          moltype = AA  length = 7
FEATURE                 Location/Qualifiers
REGION                  1..7
                        note = Clone SD232
source                  1..7
                        mol_type = protein
                        organism = synthetic construct
SEQUENCE: 162
IHTDSGR                                                                 7

SEQ ID NO: 163          moltype = AA  length = 15
FEATURE                 Location/Qualifiers
REGION                  1..15
                        note = Clone SD232
source                  1..15
                        mol_type = protein
                        organism = synthetic construct
SEQUENCE: 163
ARGISSVYWR TYFNL                                                        15

SEQ ID NO: 164          moltype = AA  length = 6
FEATURE                 Location/Qualifiers
REGION                  1..6
                        note = Clone SD232
source                  1..6
                        mol_type = protein
                        organism = synthetic construct
SEQUENCE: 164
QSIGSN                                                                  6

SEQ ID NO: 165          moltype =     length =
SEQUENCE: 165
000

SEQ ID NO: 166          moltype = AA  length = 12
FEATURE                 Location/Qualifiers
REGION                  1..12
                        note = Clone SD232
source                  1..12
                        mol_type = protein
                        organism = synthetic construct
SEQUENCE: 166
QSAYWLDSGD NG                                                           12

SEQ ID NO: 167          moltype = AA  length = 9
FEATURE                 Location/Qualifiers
REGION                  1..9
                        note = Clone SD272
source                  1..9
                        mol_type = protein
                        organism = synthetic construct
SEQUENCE: 167
GFSFNAGYW                                                               9

SEQ ID NO: 168          moltype = AA  length = 8
FEATURE                 Location/Qualifiers
REGION                  1..8
                        note = Clone SD272
source                  1..8
                        mol_type = protein
                        organism = synthetic construct
SEQUENCE: 168
IDTGSGVS                                                                8

SEQ ID NO: 169          moltype = AA  length = 10
FEATURE                 Location/Qualifiers
```

```
REGION                  1..10
                        note = Clone SD272
source                  1..10
                        mol_type = protein
                        organism = synthetic construct
SEQUENCE: 169
RNTDSIYFNL                                                                      10

SEQ ID NO: 170          moltype = AA  length = 6
FEATURE                 Location/Qualifiers
REGION                  1..6
                        note = Clone SD272
source                  1..6
                        mol_type = protein
                        organism = synthetic construct
SEQUENCE: 170
QTIYSY                                                                          6

SEQ ID NO: 171          moltype =    length =
SEQUENCE: 171
000

SEQ ID NO: 172          moltype = AA  length = 12
FEATURE                 Location/Qualifiers
REGION                  1..12
                        note = Clone SD272
source                  1..12
                        mol_type = protein
                        organism = synthetic construct
SEQUENCE: 172
QTYAGVSIYG AA                                                                   12

SEQ ID NO: 173          moltype = AA  length = 9
FEATURE                 Location/Qualifiers
REGION                  1..9
                        note = Clone SD312
source                  1..9
                        mol_type = protein
                        organism = synthetic construct
SEQUENCE: 173
GFSFSSGYY                                                                       9

SEQ ID NO: 174          moltype = AA  length = 9
FEATURE                 Location/Qualifiers
REGION                  1..9
                        note = Clone SD312
source                  1..9
                        mol_type = protein
                        organism = synthetic construct
SEQUENCE: 174
IDAGGRGDT                                                                       9

SEQ ID NO: 175          moltype = AA  length = 17
FEATURE                 Location/Qualifiers
REGION                  1..17
                        note = Clone SD312
source                  1..17
                        mol_type = protein
                        organism = synthetic construct
SEQUENCE: 175
ARRGYSSISS NFGAFNP                                                              17

SEQ ID NO: 176          moltype = AA  length = 6
FEATURE                 Location/Qualifiers
REGION                  1..6
                        note = Clone SD312
source                  1..6
                        mol_type = protein
                        organism = synthetic construct
SEQUENCE: 176
QSISSY                                                                          6

SEQ ID NO: 177          moltype =    length =
SEQUENCE: 177
000

SEQ ID NO: 178          moltype = AA  length = 12
FEATURE                 Location/Qualifiers
REGION                  1..12
```

|  |  |  |
|---|---|---|
| source | 1..12<br>mol_type = protein<br>organism = synthetic construct | |
| SEQUENCE: 178<br>QQGYTSIYVD NA | | 12 |
| SEQ ID NO: 179<br>FEATURE<br>REGION | moltype = AA  length = 9<br>Location/Qualifiers<br>1..9<br>note = Clone SD331 | |
| source | 1..9<br>mol_type = protein<br>organism = synthetic construct | |
| SEQUENCE: 179<br>GFDFTSYYY | | 9 |
| SEQ ID NO: 180<br>FEATURE<br>REGION | moltype = AA  length = 8<br>Location/Qualifiers<br>1..8<br>note = Clone SD331 | |
| source | 1..8<br>mol_type = protein<br>organism = synthetic construct | |
| SEQUENCE: 180<br>IESSSGRI | | 8 |
| SEQ ID NO: 181<br>FEATURE<br>REGION | moltype = AA  length = 13<br>Location/Qualifiers<br>1..13<br>note = Clone SD331 | |
| source | 1..13<br>mol_type = protein<br>organism = synthetic construct | |
| SEQUENCE: 181<br>RDISSSGYHG FKW | | 13 |
| SEQ ID NO: 182<br>FEATURE<br>REGION | moltype = AA  length = 6<br>Location/Qualifiers<br>1..6<br>note = Clone SD331 | |
| source | 1..6<br>mol_type = protein<br>organism = synthetic construct | |
| SEQUENCE: 182<br>QSISNY | | 6 |
| SEQ ID NO: 183<br>SEQUENCE: 183<br>000 | moltype =    length = | |
| SEQ ID NO: 184<br>FEATURE<br>REGION | moltype = AA  length = 12<br>Location/Qualifiers<br>1..12<br>note = Clone SD331 | |
| source | 1..12<br>mol_type = protein<br>organism = synthetic construct | |
| SEQUENCE: 184<br>QQVYSITNID NA | | 12 |
| SEQ ID NO: 185<br>SEQUENCE: 185<br>000 | moltype =    length = | |
| SEQ ID NO: 186<br>FEATURE<br>REGION | moltype = AA  length = 467<br>Location/Qualifiers<br>1..467<br>note = Heavy Chain Humanized Variant | |
| source | 1..467<br>mol_type = protein<br>organism = synthetic construct | |

SEQUENCE: 186
MGWTLVFLFL LSVTAGVHSQ QQLVESGGGL VKPGGTLTLT CTVSGFYFNR GYWICWVRQA  60
PGKGLEWIGC IDTGSGVPYY ANWAKGRFTI SKTSSTAVTL QMTSLTAADT ATYFCARNSD 120
SIYFNLWGPG TLVTVSSAST KGPSVFPLAP SSKSTSGGTA ALGCLVKDYF PEPVTVSWNS 180
GALTSGVHTF PAVLQSSGLY SLSSVVTVPS SSLGTQTYIC NVNHKPSNTK VDKKVEPKSC 240
DKTHTCPPCP APELLGGPSV FLFPPKPKDT LMISRTPEVT CVVVDVSHED PEVKFNWYVD 300
GVEVHNAKTK PREEQYNSTY RVVSVLTVLH QDWLNGKEYK CKVSNKALPA PIEKTISKAK 360

```
GQPREPQVYT LPPSRDELTK NQVSLTCLVK GFYPSDIAVE WESNGQPENN YKTTPPVLDS   420
DGSFFLYSKL TVDKSRWQQG NVFSCSVMHE ALHNHYTQKS LSLSPGK                467

SEQ ID NO: 187          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 187
MGWTLVFLFL LSVTAGVHSE VQLVESGGGL VKPGGSLRLS CTASGFYFNR GYWICWLRQA    60
PGKGLEWVAC IDTGSGVPYY ANWAKGRFTV SRDNAKNSLF LQMNSLRAED TAVYYCARNS   120
DSIYFNLWGP GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 188          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 188
MGWTLVFLFL LSVTAGVHSQ VQLVESGGGV VQPGRSLRLP CAASGFYFNR GYWICWVRQA    60
PGKGLEWVAC IDTGSGVPYY ANWAKGRFTI SRDTSKNTLY LQMDSLRAED TAVYYCARNS   120
DSIYFNLWGR GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 189          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 189
MGWTLVFLFL LSVTAGVHSE VQLVESGGDL AQPGGSLRLS CAVSGFYFNR GYWICWVRQA    60
PGKGLEWVSC IDTGSGVPYY ANWAKGRFTI SRDNSKNTVY LQMTSLRAED TALYFCARNS   120
DSIYFNLWGQ GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 190          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 190
MGWTLVFLFL LSVTAGVHSQ VQLVESGGGL VKPGGSLRLS CAASGFYFNR GYWICWIRQA    60
PGKGLEWVSC IDTGSGVPYY ANWAKGRFTI SRDNAKNSLY LQMNSLRTED TAVYFCARNS   120
DSIYFNLWGQ GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 191          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 191
```

```
MGWTLVFLFL LSVTAGVHSE VQLVESGGGL VKPGGSLRLS CAVSGFYFNR GYWICWVRQA    60
PGKGLEWIGC IDTGSGVPYY ANWAKGRFTI SRHTSKTTLT LQMNSLRAED TASYFCARNS   120
DSIYFNLWGP GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 192          moltype = AA   length = 237
FEATURE                 Location/Qualifiers
REGION                  1..237
                        note = Heavy Chain Humanized Variant
source                  1..237
                        mol_type = protein
                        organism = synthetic construct
SEQUENCE: 192
MVSSAQFLGL LLLCFQGTRC DIVMTQTPAS VSEPVGGTVT IKCQASQSIG GYLSWYQQKP    60
GQPPKLLIYK ASTLASGVPS RFKGSGSGTD FTLTISDLEC ADAATYYCQN YAGVSIYGAV   120
FGGGTKVVVV RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 193          moltype = AA   length = 237
FEATURE                 Location/Qualifiers
REGION                  1..237
                        note = Heavy Chain Humanized Variant
source                  1..237
                        mol_type = protein
                        organism = synthetic construct
SEQUENCE: 193
MVSSAQFLGL LLLCFQGTRC DIVMTQSPSS LSASVGDRVT ITCQASQSIG GYLSWYQQKP    60
GKAPKLLIYK ASTLASGVPS RFSGSGSGTD FTLTISSLQP EDFATYYCQN YAGVSIYGAV   120
FGGGTKVVIK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 194          moltype = AA   length = 237
FEATURE                 Location/Qualifiers
REGION                  1..237
                        note = Heavy Chain Humanized Variant
source                  1..237
                        mol_type = protein
                        organism = synthetic construct
SEQUENCE: 194
MVSSAQFLGL LLLCFQGTRC DIVLTQSPSS LSASVGDRIT ITCQASQSIG GYLSWYQQKP    60
GTPPKLLIYK ASTLASGVPS RFSGSGSGTD FTLTISRLQP EDVATYYCQN YAGVSIYGAV   120
FGGGTKLEIK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 195          moltype = AA   length = 237
FEATURE                 Location/Qualifiers
REGION                  1..237
                        note = Heavy Chain Humanized Variant
source                  1..237
                        mol_type = protein
                        organism = synthetic construct
SEQUENCE: 195
MVSSAQFLGL LLLCFQGTRC DIQMTQSPSS LSASVGDRIT ITCQASQSIG GYLSWYQQKP    60
GRVPKLLIYK ASTLASGVPS RFSGSGSGTE FTLTISSLQA EDVATYYCQN YAGVSIYGAV   120
FGGGTKVEIK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 196          moltype = AA   length = 237
FEATURE                 Location/Qualifiers
REGION                  1..237
                        note = Heavy Chain Humanized Variant
source                  1..237
                        mol_type = protein
                        organism = synthetic construct
SEQUENCE: 196
MVSSAQFLGL LLLCFQGTRC DIQMTQSPSS LSASVGDRVT ISCQASQSIG GYLSWYQQKP    60
GQAPKLLIYK ASTLASGVPS RFSGSGSGTD FTLTISSLQP EDVATYYCQN YAGVSIYGAV   120
FGQGTKVEIK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 197          moltype = AA   length = 237
FEATURE                 Location/Qualifiers
REGION                  1..237
                        note = Heavy Chain Humanized Variant
source                  1..237
```

```
                        mol_type = protein
                        organism = synthetic construct
SEQUENCE: 197
MVSSAQFLGL LLLCFQGTRC DIQMTQSPSS VSASVGDRVT ITCQASQSIG GYLSWYQQKP    60
GQPPKLLIYK ASTLASGVPS RFKGSGSGTD FTLTISSLDS EDAATYYCQN YAGVSIYGAV   120
FGGGTKVVVK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 198          moltype = AA  length = 11
FEATURE                 Location/Qualifiers
REGION                  1..11
                        note = Heavy Chain Humanized Variant
source                  1..11
                        mol_type = protein
                        organism = synthetic construct
SEQUENCE: 198
ARNSDSIYFN I                                                         11

SEQ ID NO: 199          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 199
MGWTLVFLFL LSVTAGVHSQ VQLVESGGGL VKPGGSLRLS CAASGFYFNR GYWICWIRQA    60
PGKGLEWVSC IDTGSGVPYY ANWAKGRFTI SRDNAKNSLY LQMNSLRTED TAVYFCARNS   120
DSIYFNIWGQ GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 200          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 200
MGWTLVFLFL LSVTAGVHSQ VQLVESGGGL VKPGGSLRLS CAASGFYFNR GYWISWIRQA    60
PGKGLEWVSS IDTGSGVPYY ANWAKGRFTI SRDNAKNSLY LQMNSLRTED TAVYFCARNS   120
DSIYFNLWGQ GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 201          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 201
MGWTLVFLFL LSVTAGVHSQ VQLVESGGGL VKPGGSLRLS CAASGFYFNR GYWISWIRQA    60
PGKGLEWVSS IDTGSGVPYY ANWAKGRFTI SRDNAKNSLY LQMNSLRTED TAVYFCARNS   120
DSIYFNIWGQ GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 202          moltype = AA  length = 468
FEATURE                 Location/Qualifiers
REGION                  1..468
                        note = Heavy Chain Humanized Variant
source                  1..468
                        mol_type = protein
                        organism = synthetic construct
SEQUENCE: 202
MGWTLVFLFL LSVTAGVHSE VQLVESGGGL VKPGGSLRLS CAVSGFYFNR GYWICWVRQA    60
PGKGLEWIGC IDTGSGVPYY ANWAKGRFTI SRHTSKTTLT LQMNSLRAED TASYFCARNS   120
```

```
DSIYFNIWGP GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK               468

SEQ ID NO: 203           moltype = AA  length = 468
FEATURE                  Location/Qualifiers
REGION                   1..468
                         note = Heavy Chain Humanized Variant
source                   1..468
                         mol_type = protein
                         organism = synthetic construct
SEQUENCE: 203
MGWTLVFLFL LSVTAGVHSE VQLVESGGGL VKPGGSLRLS CAVSGFYFNR GYWISWVRQA    60
PGKGLEWIGS IDTGSGVPYY ANWAKGRFTI SRHTSKTTLT LQMNSLRAED TASYFCARNS   120
DSIYFNLWGP GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK               468

SEQ ID NO: 204           moltype = AA  length = 468
FEATURE                  Location/Qualifiers
REGION                   1..468
                         note = Heavy Chain Humanized Variant
source                   1..468
                         mol_type = protein
                         organism = synthetic construct
SEQUENCE: 204
MGWTLVFLFL LSVTAGVHSE VQLVESGGGL VKPGGSLRLS CAVSGFYFNR GYWISWVRQA    60
PGKGLEWIGS IDTGSGVPYY ANWAKGRFTI SRHTSKTTLT LQMNSLRAED TASYFCARNS   120
DSIYFNIWGP GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK               468

SEQ ID NO: 205           moltype = AA  length = 237
FEATURE                  Location/Qualifiers
REGION                   1..237
                         note = Heavy Chain Humanized Variant
source                   1..237
                         mol_type = protein
                         organism = synthetic construct
SEQUENCE: 205
MVSSAQFLGL LLLCFQGTRC DIVMTQSPSS LSASVGDRVT ITCQASQSIG GYISWYQQKP    60
GKAPKLLIYK ASTLASGVPS RFSGSGSGTD FTLTISSLQP EDFATYYCQN YAGVSIYGAV   120
FGGGTKVVIK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 206           moltype = AA  length = 237
FEATURE                  Location/Qualifiers
REGION                   1..237
                         note = Heavy Chain Humanized Variant
source                   1..237
                         mol_type = protein
                         organism = synthetic construct
SEQUENCE: 206
MVSSAQFLGL LLLCFQGTRC DIQMTQSPSS VSASVGDRVT ITCQASQSIG GYISWYQQKP    60
GQPPKLLIYK ASTLASGVPS RFKGSGSGTD FTLTISSLDS EDAATYYCQN YAGVSIYGAV   120
FGGGTKVVVK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC      237

SEQ ID NO: 207           moltype = AA  length = 10
FEATURE                  Location/Qualifiers
REGION                   1..10
                         note = Clone 79C4
source                   1..10
                         mol_type = protein
                         organism = synthetic construct
SEQUENCE: 207
GFTFSNYWMN                                                           10

SEQ ID NO: 208           moltype = AA  length = 19
FEATURE                  Location/Qualifiers
```

```
REGION                   1..19
                         note = Clone 79C4
source                   1..19
                         mol_type = protein
                         organism = synthetic construct
SEQUENCE: 208
EIRLKSKNYA THYAESVKG                                                     19

SEQ ID NO: 209           moltype = AA  length = 10
FEATURE                  Location/Qualifiers
REGION                   1..10
                         note = Clone 79C4
source                   1..10
                         mol_type = protein
                         organism = synthetic construct
SEQUENCE: 209
GHYGTNYGDY                                                               10

SEQ ID NO: 210           moltype = AA  length = 11
FEATURE                  Location/Qualifiers
REGION                   1..11
                         note = Clone 79C4
source                   1..11
                         mol_type = protein
                         organism = synthetic construct
SEQUENCE: 210
RASQEISGYL S                                                             11

SEQ ID NO: 211           moltype = AA  length = 7
FEATURE                  Location/Qualifiers
REGION                   1..7
                         note = Clone 79C4
source                   1..7
                         mol_type = protein
                         organism = synthetic construct
SEQUENCE: 211
AASTLDS                                                                   7

SEQ ID NO: 212           moltype = AA  length = 9
FEATURE                  Location/Qualifiers
REGION                   1..9
                         note = Clone 79C4
source                   1..9
                         mol_type = protein
                         organism = synthetic construct
SEQUENCE: 212
LQYDSSPWT                                                                 9

SEQ ID NO: 213           moltype = AA  length = 10
FEATURE                  Location/Qualifiers
REGION                   1..10
                         note = Clone 11E12
source                   1..10
                         mol_type = protein
                         organism = synthetic construct
SEQUENCE: 213
GYTFTSYVIN                                                               10

SEQ ID NO: 214           moltype = AA  length = 17
FEATURE                  Location/Qualifiers
REGION                   1..17
                         note = Clone 11E12
source                   1..17
                         mol_type = protein
                         organism = synthetic construct
SEQUENCE: 214
EIHPRGGNTY YSEKFRG                                                       17

SEQ ID NO: 215           moltype = AA  length = 9
FEATURE                  Location/Qualifiers
REGION                   1..9
                         note = Clone 11E12
source                   1..9
                         mol_type = protein
                         organism = synthetic construct
SEQUENCE: 215
LRRGNAMDY                                                                 9

SEQ ID NO: 216           moltype = AA  length = 17
```

```
                          -continued

FEATURE                 Location/Qualifiers
REGION                  1..17
                        note = Clone 11E12
source                  1..17
                        mol_type = protein
                        organism = synthetic construct
SEQUENCE: 216
KSSQSLLNSG NQRNYLT                                                  17

SEQ ID NO: 217          moltype = AA  length = 7
FEATURE                 Location/Qualifiers
REGION                  1..7
                        note = Clone 11E12
source                  1..7
                        mol_type = protein
                        organism = synthetic construct
SEQUENCE: 217
WASTRES                                                              7

SEQ ID NO: 218          moltype = AA  length = 9
FEATURE                 Location/Qualifiers
REGION                  1..9
                        note = Clone 11E12
source                  1..9
                        mol_type = protein
                        organism = synthetic construct
SEQUENCE: 218
QNSYNYPYT                                                            9

SEQ ID NO: 219          moltype = AA  length = 10
FEATURE                 Location/Qualifiers
REGION                  1..10
                        note = Clone 83G3
source                  1..10
                        mol_type = protein
                        organism = synthetic construct
SEQUENCE: 219
GFTFTSYWIH                                                          10

SEQ ID NO: 220          moltype = AA  length = 17
FEATURE                 Location/Qualifiers
REGION                  1..17
                        note = Clone 83G3
source                  1..17
                        mol_type = protein
                        organism = synthetic construct
SEQUENCE: 220
YIDPSNTYTK FNQKFKD                                                  17

SEQ ID NO: 221          moltype = AA  length = 6
FEATURE                 Location/Qualifiers
REGION                  1..6
                        note = Clone 83G3
source                  1..6
                        mol_type = protein
                        organism = synthetic construct
SEQUENCE: 221
GRGFAY                                                               6

SEQ ID NO: 222          moltype = AA  length = 18
FEATURE                 Location/Qualifiers
REGION                  1..18
                        note = Clone 83G3
source                  1..18
                        mol_type = protein
                        organism = synthetic construct
SEQUENCE: 222
DKSSQSLFNS GNQKHYLT                                                 18

SEQ ID NO: 223          moltype = AA  length = 7
FEATURE                 Location/Qualifiers
REGION                  1..7
                        note = Clone 83G3
source                  1..7
                        mol_type = protein
                        organism = synthetic construct
SEQUENCE: 223
RASTRES                                                              7
```

```
SEQ ID NO: 224           moltype = AA   length = 9
FEATURE                  Location/Qualifiers
REGION                   1..9
                         note = Clone 83G3
source                   1..9
                         mol_type = protein
                         organism = synthetic construct
SEQUENCE: 224
QNDYSFPLT                                                                 9

SEQ ID NO: 225           moltype = AA   length = 10
FEATURE                  Location/Qualifiers
REGION                   1..10
                         note = Clone 30B5
source                   1..10
                         mol_type = protein
                         organism = synthetic construct
SEQUENCE: 225
GFTFSNYWMN                                                               10

SEQ ID NO: 226           moltype = AA   length = 19
FEATURE                  Location/Qualifiers
REGION                   1..19
                         note = Clone 30B5
source                   1..19
                         mol_type = protein
                         organism = synthetic construct
SEQUENCE: 226
EIRLKSKNYA THYAESVKG                                                     19

SEQ ID NO: 227           moltype = AA   length = 10
FEATURE                  Location/Qualifiers
REGION                   1..10
                         note = Clone 30B5
source                   1..10
                         mol_type = protein
                         organism = synthetic construct
SEQUENCE: 227
GHYGTNYGDY                                                               10

SEQ ID NO: 228           moltype = AA   length = 17
FEATURE                  Location/Qualifiers
REGION                   1..17
                         note = Clone 30B5
source                   1..17
                         mol_type = protein
                         organism = synthetic construct
SEQUENCE: 228
KSSQSLFNSG NQKHYLT                                                       17

SEQ ID NO: 229           moltype = AA   length = 7
FEATURE                  Location/Qualifiers
REGION                   1..7
                         note = Clone 30B5
source                   1..7
                         mol_type = protein
                         organism = synthetic construct
SEQUENCE: 229
RASTRES                                                                   7

SEQ ID NO: 230           moltype = AA   length = 9
FEATURE                  Location/Qualifiers
REGION                   1..9
                         note = Clone 30B5
source                   1..9
                         mol_type = protein
                         organism = synthetic construct
SEQUENCE: 230
QNDYSFPLT                                                                 9

SEQ ID NO: 231           moltype = AA   length = 10
FEATURE                  Location/Qualifiers
REGION                   1..10
                         note = Clone 85H12
source                   1..10
                         mol_type = protein
                         organism = synthetic construct
SEQUENCE: 231
GFTFSNYWMN                                                               10
```

```
SEQ ID NO: 232          moltype = AA   length = 19
FEATURE                 Location/Qualifiers
REGION                  1..19
                        note = Clone 85H12
source                  1..19
                        mol_type = protein
                        organism = synthetic construct
SEQUENCE: 232
EIRLKSKNYA THYAESVKG                                                    19

SEQ ID NO: 233          moltype = AA   length = 10
FEATURE                 Location/Qualifiers
REGION                  1..10
                        note = Clone 85H12
source                  1..10
                        mol_type = protein
                        organism = synthetic construct
SEQUENCE: 233
GHYGTNYGDY                                                              10

SEQ ID NO: 234          moltype = AA   length = 17
FEATURE                 Location/Qualifiers
REGION                  1..17
                        note = Clone 85H12
source                  1..17
                        mol_type = protein
                        organism = synthetic construct
SEQUENCE: 234
KSSQSLFNSG NQKHYLT                                                      17

SEQ ID NO: 235          moltype = AA   length = 7
FEATURE                 Location/Qualifiers
REGION                  1..7
                        note = Clone 85H12
source                  1..7
                        mol_type = protein
                        organism = synthetic construct
SEQUENCE: 235
RASTRES                                                                  7

SEQ ID NO: 236          moltype = AA   length = 9
FEATURE                 Location/Qualifiers
REGION                  1..9
                        note = Clone 85H12
source                  1..9
                        mol_type = protein
                        organism = synthetic construct
SEQUENCE: 236
QNDYSFPLT                                                                9

SEQ ID NO: 237          moltype = AA   length = 121
FEATURE                 Location/Qualifiers
REGION                  1..121
                        note = Heavy chain variable domain
source                  1..121
                        mol_type = protein
                        organism = synthetic construct
SEQUENCE: 237
EVKLEESGGG LVQPGGSMKL SCVASGFTFS NYWMNWVRQS PEKGLEWVAE IRLKSKNYAT        60
HYAESVKGRF TISRDDSIGS VYLQMNNLRA EDTGIYYCAR GHYGTNYGDY WGQGTSVTVS       120
S                                                                      121

SEQ ID NO: 238          moltype = AA   length = 118
FEATURE                 Location/Qualifiers
REGION                  1..118
                        note = Heavy chain variable domain
source                  1..118
                        mol_type = protein
                        organism = synthetic construct
SEQUENCE: 238
QVQLQQSGAE LARPGASVKL SCKASGYTFT SYVINWVKQK TGQGLEWIGE IHPRGGNTYY        60
SEKFRGRATL TADKSSSTAY MEFRSLTSED SAVYFCAILR RGNAMDYWDQ GTAVTVSS         118

SEQ ID NO: 239          moltype = AA   length = 115
FEATURE                 Location/Qualifiers
REGION                  1..115
                        note = Heavy chain variable domain
source                  1..115
```

```
                             mol_type = protein
                             organism = synthetic construct
SEQUENCE: 239
QVQLQQSGAE LAKPGASVKL SCKASGFTFT SYWIHWVKQR PGQGLEWIGY IDPSNTYTKF    60
NQKFKDKATL TADKSSSTAY MQLNSLTFED SAVYYCATGR GFAYWGQGTL VTVSS        115

SEQ ID NO: 240               moltype = AA  length = 121
FEATURE                      Location/Qualifiers
REGION                       1..121
                             note = Heavy chain variable domain
source                       1..121
                             mol_type = protein
                             organism = synthetic construct
SEQUENCE: 240
EVKLEESGGG LVQPGGSMKL SCVASGFTFS NYWMNWVRQS PEKGLEWVAE IRLKSKNYAT    60
HYAESVKGRF TISRDDSIGS VYLQMNNLRA EDTGIYYCAR GHYGTNYGDY WGQGTSVTVS   120
S                                                                  121

SEQ ID NO: 241               moltype = AA  length = 121
FEATURE                      Location/Qualifiers
REGION                       1..121
                             note = Heavy chain variable domain
source                       1..121
                             mol_type = protein
                             organism = synthetic construct
SEQUENCE: 241
EVKLEESGGG LVQPGGSMKL SCVASGFTFS NYWMNWVRQS PEKGLEWVAE IRLKSKNYAT    60
HYAESVKGRF TISRDDSIGS VYLQMNNLRA EDTGIYYCAR GHYGTNYGDY WGQGTSVTVS   120
S                                                                  121

SEQ ID NO: 242               moltype = AA  length = 107
FEATURE                      Location/Qualifiers
REGION                       1..107
                             note = Light chain variable domain Protein Sequence
source                       1..107
                             mol_type = protein
                             organism = synthetic construct
SEQUENCE: 242
DIQTTQSPSS LSASLGERVT LTCRASQEIS GYLSWLQQKP DGTIKRLIYA ASTLDSGVPK    60
RFSGSRSGSD YSLTINSLES EDFVDYYCLQ YDSSPWTFGG GTKLEIK                107

SEQ ID NO: 243               moltype = AA  length = 113
FEATURE                      Location/Qualifiers
REGION                       1..113
                             note = Light chain variable domain Protein Sequence
source                       1..113
                             mol_type = protein
                             organism = synthetic construct
SEQUENCE: 243
DIVMTQSPSS LPVTAGEMVT MSCKSSQSLL NSGNQRNYLT WYQQKPGQPP KLLIYWASTR    60
ESGVPDRFTG SGSGTDFTLT ISSVQAEDLA VYYCQNSYNY PYTFGGGTKL ERK          113

SEQ ID NO: 244               moltype = AA  length = 113
FEATURE                      Location/Qualifiers
REGION                       1..113
                             note = Light chain variable domain Protein Sequence
source                       1..113
                             mol_type = protein
                             organism = synthetic construct
SEQUENCE: 244
DIVMTQSPSS LTVTAGEKVT VSCKSSQSLF NSGNQKHYLT WYQQKPGQPP KLLIYRASTR    60
ESGVPDRFTG SGSGTDFTLT IRNVQAEDLA VYYCQNDYSF PLTFGAGTKL ELK          113

SEQ ID NO: 245               moltype = AA  length = 113
FEATURE                      Location/Qualifiers
REGION                       1..113
                             note = Light chain variable domain Protein Sequence
source                       1..113
                             mol_type = protein
                             organism = synthetic construct
SEQUENCE: 245
DIVMTQSPSS LTVTAGEKVT VSCKSSQSLF NSGNQKHYLT WYQQKPGQPP KLLIYRASTR    60
ESGVPDRFTG SGSGTDFTLT IRNVQAEDLA VYYCQNDYSF PLTFGAGTKL ELK          113

SEQ ID NO: 246               moltype = AA  length = 113
FEATURE                      Location/Qualifiers
REGION                       1..113
                             note = Light chain variable domain Protein Sequence
source                       1..113
```

```
                        mol_type = protein
                        organism = synthetic construct
SEQUENCE: 246
DIVMTQSPSS LTVTAGEKVT VSCKSSQSLF NSGNQKHYLT WYQQKPGQPP KLLIYRASTR    60
ESGVPDRFTG SGSGTDFTLT IRNVQAEDLA VYYCQNDYSF PLTFGAGTKL ELK           113

SEQ ID NO: 247          moltype = AA   length = 9
FEATURE                 Location/Qualifiers
REGION                  1..9
                        note = Clone 11E12
source                  1..9
                        mol_type = protein
                        organism = synthetic construct
SEQUENCE: 247
IRRGNAMDY                                                             9

SEQ ID NO: 248          moltype = AA   length = 118
FEATURE                 Location/Qualifiers
REGION                  1..118
                        note = Heavy chain variable domain
source                  1..118
                        mol_type = protein
                        organism = synthetic construct
SEQUENCE: 248
QVQLQQSGAE LARPGASVKL SCKASGYTFT SYVINWVKQK TGQGLEWIGE IHPRGGNTYY    60
SEKFRGRATL TADKSSSTAY MEFRSLTSED SAVYFCARIR RGNAMDYWDQ GTAVTVSS      118

SEQ ID NO: 249          moltype = AA   length = 448
FEATURE                 Location/Qualifiers
REGION                  1..448
                        note = Heavy Chain Humanized Variant
source                  1..448
                        mol_type = protein
                        organism = synthetic construct
SEQUENCE: 249
QVQLVQSGAE VKKPGASVKV SCKASGYTFT SYVINWVRQA TGQGLEWIGE IHPRGGNTYY    60
SEKFRGRATM TRDTSISTAY MELSSLRSED TAVYYCARIR RGNAMDYWGQ GTTLTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 250          moltype = AA   length = 448
FEATURE                 Location/Qualifiers
REGION                  1..448
                        note = Heavy Chain Humanized Variant
source                  1..448
                        mol_type = protein
                        organism = synthetic construct
SEQUENCE: 250
QVQLVQSGAE VKKPGASVKV SCKASGYTFT SYVINWVRQA TGQGLEWIGE IHPRGGNTYY    60
SEKFRGRATL TRDTSISTAY MELSSLRSED TAVYYCARIR RGNAMDYWGQ GTTLTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 251          moltype = AA   length = 448
FEATURE                 Location/Qualifiers
REGION                  1..448
                        note = Heavy Chain Humanized Variant
source                  1..448
                        mol_type = protein
                        organism = synthetic construct
SEQUENCE: 251
QVQLVQSGAE VKKPGASVKV SCKASGYTFT SYVINWVRQA TGQGLEWIGE IHPRGGNTYY    60
SEKFRGRATL TRDTSISTAY MELSSLRSED TAVYYCARLR RGNAMDYWGQ GTTLTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 252          moltype = AA   length = 220
```

```
FEATURE                 Location/Qualifiers
REGION                  1..220
                        note = Heavy Chain Humanized Variant
source                  1..220
                        mol_type = protein
                        organism = synthetic construct
SEQUENCE: 252
DIVMTQSPSS LAVSLGERAT INCKSSQSLL NSGNQRNYLT WYQQKPGQPP KLLIYWASTR  60
ESGVPDRFSG SGSGTDFTLT ISSLQAEDVA VYYCQNSYNY PYTFGQGTKL EIKRTVAAPS 120
VFIFPPSDEQ LKSGTASVVC LLNNFYPREA KVQWKVDNAL QSGNSQESVT EQDSKDSTYS 180
LSSTLTLSKA DYEKHKVYAC EVTHQGLSSP VTKSFNRGEC                      220

SEQ ID NO: 253          moltype = AA  length = 220
FEATURE                 Location/Qualifiers
REGION                  1..220
                        note = Heavy Chain Humanized Variant
source                  1..220
                        mol_type = protein
                        organism = synthetic construct
SEQUENCE: 253
DIVMTQSPSS LPVSLGERAT INCKSSQSLL NSGNQRNYLT WYQQKPGQPP KLLIYWASTR  60
ESGVPDRFSG SGSGTDFTLT ISSLQAEDVA VYYCQNSYNY PYTFGQGTKL EIKRTVAAPS 120
VFIFPPSDEQ LKSGTASVVC LLNNFYPREA KVQWKVDNAL QSGNSQESVT EQDSKDSTYS 180
LSSTLTLSKA DYEKHKVYAC EVTHQGLSSP VTKSFNRGEC                      220

SEQ ID NO: 254          moltype = AA  length = 118
FEATURE                 Location/Qualifiers
REGION                  1..118
                        note = Humanized heavy chain and light chain variable
                         domain Protein Sequences
source                  1..118
                        mol_type = protein
                        organism = synthetic construct
SEQUENCE: 254
QVQLVQSGAE VKKPGASVKV SCKASGYTFT SYVINWVRQA TGQGLEWIGE IHPRGGNTYY  60
SEKFRGRVTL TADTSISTAY MELSSLRSED TAVYYCAILR RGNAMDYWDQ GTTVTVSS   118

SEQ ID NO: 255          moltype = AA  length = 118
FEATURE                 Location/Qualifiers
REGION                  1..118
                        note = Humanized heavy chain and light chain variable
                         domain Protein Sequences
source                  1..118
                        mol_type = protein
                        organism = synthetic construct
SEQUENCE: 255
QVQLVQSGAE VKKPGASVKV SCKASGYTFT SYVINWVKQK TGQGLEWIGE IHPRGGNTYY  60
SEKFRGRATL TADKSISTAY MELSSLRSED TAVYFCAILR RGNAMDYWDQ GTTVTVSS   118

SEQ ID NO: 256          moltype = AA  length = 118
FEATURE                 Location/Qualifiers
REGION                  1..118
                        note = Humanized heavy chain and light chain variable
                         domain Protein Sequences
source                  1..118
                        mol_type = protein
                        organism = synthetic construct
SEQUENCE: 256
QVQLVQSGAE VKKPGASVKL SCKASGYTFT SYVINWVKQK TGQGLEWIGE IHPRGGNTYY  60
SEKFRGRATL TADKSISTAY MELSSLRSED TAVYFCAILR RGNAMDYWDQ GTTVTVSS   118

SEQ ID NO: 257          moltype = AA  length = 118
FEATURE                 Location/Qualifiers
REGION                  1..118
                        note = Humanized heavy chain and light chain variable
                         domain Protein Sequences
source                  1..118
                        mol_type = protein
                        organism = synthetic construct
SEQUENCE: 257
QVQLVQSGAE VKKPGASVKV SCKASGYTFT SYVINWVRQA TGQGLEWIGE IHPRGGNTYY  60
SEKFRGRVTL TADTSISTAY MELSSLRSED TAVYYCARLR RGNAMDYWDQ GTTVTVSS   118

SEQ ID NO: 258          moltype = AA  length = 118
FEATURE                 Location/Qualifiers
REGION                  1..118
                        note = Humanized heavy chain and light chain variable
                         domain Protein Sequences
source                  1..118
```

```
                        mol_type = protein
                        organism = synthetic construct
SEQUENCE: 258
QVQLVQSGAE VKKPGASVKV SCKASGYTFT SYVINWVKQK TGQGLEWIGE IHPRGGNTYY    60
SEKFRGRATL TADKSISTAY MELSSLRSED TAVYFCARLR RGNAMDYWDQ GTTVTVSS     118

SEQ ID NO: 259          moltype = AA   length = 118
FEATURE                 Location/Qualifiers
REGION                  1..118
                        note = Humanized heavy chain and light chain variable
                         domain Protein Sequences
source                  1..118
                        mol_type = protein
                        organism = synthetic construct
SEQUENCE: 259
QVQLVQSGAE VKKPGASVKL SCKASGYTFT SYVINWVKQK TGQGLEWIGE IHPRGGNTYY    60
SEKFRGRATL TADKSISTAY MELSSLRSED TAVYFCARLR RGNAMDYWDQ GTTVTVSS     118

SEQ ID NO: 260          moltype = AA   length = 113
FEATURE                 Location/Qualifiers
REGION                  1..113
                        note = Humanized heavy chain and light chain variable
                         domain Protein Sequences
source                  1..113
                        mol_type = protein
                        organism = synthetic construct
SEQUENCE: 260
DIVMTQSPSS LAVSLGEMAT INCKSSQSLL NSGNQRNYLT WYQQKPGQPP KLLIYWASTR    60
ESGVPDRFSG SGSGTDFTLT ISSLQAEDVA VYYCQNSYNY PYTFGQGTKL ERK          113

SEQ ID NO: 261          moltype = AA   length = 113
FEATURE                 Location/Qualifiers
REGION                  1..113
                        note = Humanized heavy chain and light chain variable
                         domain Protein Sequences
source                  1..113
                        mol_type = protein
                        organism = synthetic construct
SEQUENCE: 261
DIVMTQSPSS LAVSAGEMVT MNCKSSQSLL NSGNQRNYLT WYQQKPGQPP KLLIYWASTR    60
ESGVPDRFSG SGSGTDFTLT ISSVQAEDLA VYYCQNSYNY PYTFGQGTKL EIK          113

SEQ ID NO: 262          moltype = AA   length = 113
FEATURE                 Location/Qualifiers
REGION                  1..113
                        note = Humanized heavy chain and light chain variable
                         domain Protein Sequences
source                  1..113
                        mol_type = protein
                        organism = synthetic construct
SEQUENCE: 262
DIVMTQSPSS LAVSAGEMVT MNCKSSQSLL NSGNQRNYLT WYQQKPGQPP KLLIYWASTR    60
ESGVPDRFSG SGSGTDFTLT ISSVQAEDLA VYYCQNSYNY PYTFGQGTKL ERK          113

SEQ ID NO: 263          moltype = AA   length = 115
FEATURE                 Location/Qualifiers
REGION                  1..115
                        note = 83G3 Humanized Sequences
source                  1..115
                        mol_type = protein
                        organism = synthetic construct
SEQUENCE: 263
QVQLVQSGAE VKKPGASVKV SCKASGFTFT SYWIHWVRQR PGQGLEWIGY IDPSNTYTKF    60
NQKFKDRVTL TADTSTSTAY MELSSLRSED TAVYYCATGR GFAYWGQGTL VTSS         115

SEQ ID NO: 264          moltype = AA   length = 115
FEATURE                 Location/Qualifiers
REGION                  1..115
                        note = 83G3 Humanized Sequences
source                  1..115
                        mol_type = protein
                        organism = synthetic construct
SEQUENCE: 264
QVQLVQSGAE VKKPGASVKL SCKASGFTFT SYWIHWVRQR PGQGLEWIGY IDPSNTYTKF    60
NQKFKDRATL TADTSTSTAY MELSSLRSED TAVYYCATGR GFAYWGQGTL VTSS         115

SEQ ID NO: 265          moltype = AA   length = 115
FEATURE                 Location/Qualifiers
REGION                  1..115
```

```
                        note = 83G3 Humanized Sequences
source                  1..115
                        mol_type = protein
                        organism = synthetic construct
SEQUENCE: 265
QVQLQQSGAE VKKPGASVKL SCKASGFTFT SYWIHWVRQR PGQGLEWIGY IDPSNTYTKF    60
NQKFKDRATL TADTSTSTAY MELSSLRSED TAVYYCATGR GFAYWGQGTL VTVSS        115

SEQ ID NO: 266          moltype = AA  length = 113
FEATURE                 Location/Qualifiers
REGION                  1..113
                        note = 83G3 Humanized Sequences
source                  1..113
                        mol_type = protein
                        organism = synthetic construct
SEQUENCE: 266
DIVMTQSPSS LAVSLGERAT INCKSSQSLF NSGNQKHYLT WYQQKPGQPP KLLIYRASTR    60
ESGVPDRFSG SGSGTDFTLT ISSLQAEDVA VYYCQNDYSF PLTFGQGTKL EIK          113

SEQ ID NO: 267          moltype = AA  length = 113
FEATURE                 Location/Qualifiers
REGION                  1..113
                        note = 83G3 Humanized Sequences
source                  1..113
                        mol_type = protein
                        organism = synthetic construct
SEQUENCE: 267
DIVMTQSPSS LAVSLGERAT VNCKSSQSLF NSGNQKHYLT WYQQKPGQPP KLLIYRASTR    60
ESGVPDRFSG SGSGTDFTLT ISSLQAEDVA VYYCQNDYSF PLTFGQGTKL EIK          113

SEQ ID NO: 268          moltype = AA  length = 113
FEATURE                 Location/Qualifiers
REGION                  1..113
                        note = 83G3 Humanized Sequences
source                  1..113
                        mol_type = protein
                        organism = synthetic construct
SEQUENCE: 268
DIVMTQSPSS LAVSLGERAT VNCKSSQSLF NSGNQKHYLT WYQQKPGQPP KLLIYRASTR    60
ESGVPDRFSG SGSGTDFTLT IRSLQAEDVA VYYCQNDYSF PLTFGQGTKL EIK          113

SEQ ID NO: 269          moltype = AA  length = 113
FEATURE                 Location/Qualifiers
REGION                  1..113
                        note = 83G3 Humanized Sequences
source                  1..113
                        mol_type = protein
                        organism = synthetic construct
SEQUENCE: 269
DIVMTQSPSS LAVSLGERAT VNCKSSQSLF NSGNQKHYLT WYQQKPGQPP KLLIYRASTR    60
ESGVPDRFTG SGSGTDFTLT ISSLQAEDVA VYYCQNDYSF PLTFGQGTKL EIK          113
```

ANTIBODIES AND METHODS FOR MAKING AND USING THE SAME

CROSS REFERENCE TO RELATED APPLICATIONS

The present application is a Divisional Application of U.S. patent application Ser. No. 16/516,223 filed Jul. 18, 2019 which claims priority to US provisional patent applications 62/700,174 filed on Jul. 18, 2018 and 62/792,798 filed on Jan. 15, 2019, and each is incorporated by reference herein in their entirety.

REFERENCE TO SEQUENCE LISTING

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed .xml file as follows: File Name: AG3-015USC1; Date of Creation: May 24, 2023; Size (bytes): 322 KB.

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art.

It was recently shown that there were close to one million new cases of gastric cancer worldwide every year. The worldwide mortality rate for gastric cancer was over 700,000 in 2012. According to the American Cancer Society, in 2018, about 26,400 people were diagnosed with gastric cancer in the United States with about 10,800 expected fatalities. The incidence of gastric cancer as a percentage of the overall population is higher in Asia, with about 40% of all gastric cancer cases reported worldwide in 2012 or approximately 400,000 cases found to occur in China. 325,000 people died of gastric cancer in China in 2012. These demographic data make it clear that gastric cancer is a severe unmet medical condition with limited therapy options in which existing methods of treatment are not adequate and new therapeutic compounds and treatments are urgently needed.

To treat gastric cancer, a combination of 5-Fu and Cis-platin is often the first line treatment in many countries. However, the combination of Paclitaxel and Cisplatin is often used to treat gastric patients in China and was said to have better therapeutic efficacy.

Antibodies are a relatively new class of targeted therapeutic compounds that are now widely used for a variety of cancers. Antibody-based therapeutics have the potential for higher specificity and lower side effects compared to many traditional non-antibody type oncology therapeutics. Generally, potential targets for antibody-based therapeutics need to discriminate between normal and neoplastic cells. Not surprisingly, cell surface proteins are a potential area of development of antibody-based targets that might be exposed on tumor cells. Claudin 18.2 was recently found to be a target for antibody therapy for gastric and esophageal cancers (J Hematol Oncol. 2017 (1):105). It was also a target for developing antibody drugs for pancreatic cancer. Claudin 18.2 belongs to the claudin family of proteins, which has at least 24 closely related transmembrane proteins (for review, see Ouban A, Ahmed AA.: "Claudins in human cancer: a review", Histol Histopathol. 2010 January; 25(1):83-90).

Claudins are tight junction proteins which regulate paracellular ion flux. Certain claudin protein members are differentially expressed in malignancies. In the case of Claudin 18.2, it is a highly selective gastric lineage antigen expressed exclusively on short-lived differentiated gastric epithelial cells, which has only limited accessibility to antibody drugs (Sahin U et al: "Claudin18 splice variant 2 is a pan-cancer target suitable for therapeutic antibody development." Clin Cancer Res 2008, 14:7624-34; and Tureci O et al. "Claudin-18 gene structure, regulation, and expression is evolutionary conserved in mammal." Gene 2011, 481:83-92). Claudin18.2 is maintained during the course of malignant transformation and thus frequently displayed on the surface of human gastric cancer cells (Wöll et all: "Claudin 18.2 is a target for IMAB362 antibody in pancreatic neoplasms." Int. J. Cancer: 134, 731-739, 2014).

An antibody against Claudin 18.2 designated IMAB362 was recently disclosed in U.S. Pat. No. 8,168,427. In a Phase 2 study published in 2016, patients with advanced or recurrent gastric cancer and gastroesophageal junction carcinomas treated with IMAB362 added to standard chemotherapy demonstrated a 53% reduced risk for progression and a 49% reduced risk of death compared with patients who received only standard EOX (Epirubicin, Oxaliplatin and Capecitabine). However, the binding affinity of the particular antibody IMAb362 to the target Claudin 18.2 appeared to be relatively modest, and the dosages required appeared to be relatively high. In addition, the antibody in the clinical development was a chimeric molecule, which could potentially have immunogenicity risk after repeating doses.

New antibodies to Claudin 18.2 with higher efficacy, lower dosage/cost, and/or lower immunogenicity risk are needed.

SUMMARY

The inventions described and claimed herein have many attributes and embodiments including, but not limited to, those set forth or described or referenced in this Brief Summary. The inventions described and claimed herein are not limited to, or by, the features or embodiments identified in this Summary, which is included for purposes of illustration only and not restriction.

Described and provided herein are novel antibodies for Claudin 18.2. As will be described in further detail herein, antibodies according to the invention include but are not limited to the following characteristics: i) high relative binding affinity for Claudin 18.2, ii) human or humanized antibody, iii) enhanced antibody-drug conjugation capabilities, iv) enhanced combination use with immune-therapy, v) enhanced ADCC functionality, and vi) enhanced therapeutic efficacy.

In one aspect, the present invention provides an antibody which binds to human CLDN18.2 protein, the antibody selected from the group consisting of:

(1) an antibody comprising a heavy chain variable region comprising heavy chain CDR1 having the amino acid sequence as set forth in SEQ ID NO: 47, heavy chain CDR2 having the amino acid sequence as set forth in SEQ ID NO: 48, and heavy chain CDR3 having the amino acid sequence as set forth in SEQ ID NO: 49, and a light chain variable region comprising light chain CDR1 having the amino acid sequence as set forth in SEQ ID NO: 50, light chain CDR2 having the amino acid sequence as set forth in SEQ ID NO: 51, and light chain CDR3 having the amino acid sequence as set forth in SEQ ID NO: 52;

(2) an antibody comprising a heavy chain variable region comprising heavy chain CDR1 having the amino acid sequence as set forth in SEQ ID NO: 53, heavy chain CDR2 having the amino acid sequence as set forth in SEQ ID NO: 54, and heavy chain CDR3 having the amino acid sequence as set forth in SEQ ID NO: 55, and a light chain variable region comprising light chain CDR1 having the amino acid sequence as set forth in SEQ ID NO: 56, light chain CDR2 having the amino acid sequence as set forth in SEQ ID NO: 57, and light chain CDR3 having the amino acid sequence as set forth in SEQ ID NO: 58;

(3) an antibody comprising a heavy chain variable region comprising heavy chain CDR1 having the amino acid sequence as set forth in SEQ ID NO: 59, heavy chain CDR2 having the amino acid sequence as set forth in SEQ ID NO: 60, and heavy chain CDR3 having the amino acid sequence as set forth in SEQ ID NO: 61, and a light chain variable region comprising light chain CDR1 having the amino acid sequence as set forth in SEQ ID NO: 62, light chain CDR2 having the amino acid sequence as set forth in SEQ ID NO: 63, and light chain CDR3 having the amino acid sequence as set forth in SEQ ID NO: 64;

(4) an antibody comprising a heavy chain variable region comprising heavy chain CDR1 having the amino acid sequence as set forth in SEQ ID NO: 65, heavy chain CDR2 having the amino acid sequence as set forth in SEQ ID NO: 66, and heavy chain CDR3 having the amino acid sequence as set forth in SEQ ID NO: 67, and a light chain variable region comprising light chain CDR1 having the amino acid sequence as set forth in SEQ ID NO: 68, light chain CDR2 having the amino acid sequence as set forth in SEQ ID NO: 69, and light chain CDR3 having the amino acid sequence as set forth in SEQ ID NO: 70;

(5) an antibody comprising a heavy chain variable region comprising heavy chain CDR1 having the amino acid sequence as set forth in SEQ ID NO: 71, heavy chain CDR2 having the amino acid sequence as set forth in SEQ ID NO: 72, and heavy chain CDR3 having the amino acid sequence as set forth in SEQ ID NO: 73, and a light chain variable region comprising light chain CDR1 having the amino acid sequence as set forth in SEQ ID NO: 74, light chain CDR2 having the amino acid sequence as set forth in SEQ ID NO: 75, and light chain CDR3 having the amino acid sequence as set forth in SEQ ID NO: 76;

(6) an antibody comprising a heavy chain variable region comprising heavy chain CDR1 having the amino acid sequence as set forth in SEQ ID NO: 77, heavy chain CDR2 having the amino acid sequence as set forth in SEQ ID NO: 78, and heavy chain CDR3 having the amino acid sequence as set forth in SEQ ID NO: 79, and a light chain variable region comprising light chain CDR1 having the amino acid sequence as set forth in SEQ ID NO: 80, light chain CDR2 having the amino acid sequence as set forth in SEQ ID NO: 81, and light chain CDR3 having the amino acid sequence as set forth in SEQ ID NO: 82;

(7) an antibody comprising a heavy chain variable region comprising heavy chain CDR1 having the amino acid sequence as set forth in SEQ ID NO: 83, heavy chain CDR2 having the amino acid sequence as set forth in SEQ ID NO: 84, and heavy chain CDR3 having the amino acid sequence as set forth in SEQ ID NO: 85, and a light chain variable region comprising light chain CDR1 having the amino acid sequence as set forth in SEQ ID NO: 86, light chain CDR2 having the amino acid sequence as set forth in SEQ ID NO: 87, and light chain CDR3 having the amino acid sequence as set forth in SEQ ID NO: 88;

(8) an antibody comprising a heavy chain variable region comprising heavy chain CDR1 having the amino acid sequence as set forth in SEQ ID NO: 89, heavy chain CDR2 having the amino acid sequence as set forth in SEQ ID NO: 90, and heavy chain CDR3 having the amino acid sequence as set forth in SEQ ID NO: 91, and a light chain variable region comprising light chain CDR1 having the amino acid sequence as set forth in SEQ ID NO: 92, light chain CDR2 having the amino acid sequence as set forth in SEQ ID NO: 93, and light chain CDR3 having the amino acid sequence as set forth in SEQ ID NO: 94;

(9) an antibody comprising a heavy chain variable region comprising heavy chain CDR1 having the amino acid sequence as set forth in SEQ ID NO: 95, heavy chain CDR2 having the amino acid sequence as set forth in SEQ ID NO: 96, and heavy chain CDR3 having the amino acid sequence as set forth in SEQ ID NO: 97, and a light chain variable region comprising light chain CDR1 having the amino acid sequence as set forth in SEQ ID NO: 98, light chain CDR2 having the amino acid sequence as set forth in SEQ ID NO: 99, and light chain CDR3 having the amino acid sequence as set forth in SEQ ID NO: 100;

(10) an antibody comprising a heavy chain variable region comprising heavy chain CDR1 having the amino acid sequence as set forth in SEQ ID NO: 101, heavy chain CDR2 having the amino acid sequence as set forth in SEQ ID NO: 102, and heavy chain CDR3 having the amino acid sequence as set forth in SEQ ID NO: 103, and a light chain variable region comprising light chain CDR1 having the amino acid sequence as set forth in SEQ ID NO: 104, light chain CDR2 having the amino acid sequence as set forth in SEQ ID NO: 105, and light chain CDR3 having the amino acid sequence as set forth in SEQ ID NO: 106;

(11) an antibody comprising a heavy chain variable region comprising heavy chain CDR1 having the amino acid sequence as set forth in SEQ ID NO: 107, heavy chain CDR2 having the amino acid sequence as set forth in SEQ ID NO: 108, and heavy chain CDR3 having the amino acid sequence as set forth in SEQ ID NO: 109, and a light chain variable region comprising light chain CDR1 having the amino acid sequence as set forth in SEQ ID NO: 110, light chain CDR2 having the amino acid sequence as set forth in SEQ ID NO: 111, and light chain CDR3 having the amino acid sequence as set forth in SEQ ID NO: 112;

(12) an antibody comprising a heavy chain variable region comprising heavy chain CDR1 having the amino acid sequence as set forth in SEQ ID NO: 113, heavy chain CDR2 having the amino acid sequence as set forth in SEQ ID NO: 114, and heavy chain CDR3 having the amino acid sequence as set forth in SEQ ID NO: 115, and a light chain variable region comprising light chain CDR1 having the amino acid sequence as set forth in SEQ ID NO: 116, light chain CDR2 having the amino acid sequence as set forth in SEQ ID NO: 117, and light chain CDR3 having the amino acid sequence as set forth in SEQ ID NO: 118;

(13) an antibody comprising a heavy chain variable region comprising heavy chain CDR1 having the amino acid sequence as set forth in SEQ ID NO: 119, heavy chain CDR2 having the amino acid sequence as set forth in SEQ ID NO: 120, and heavy chain CDR3 having the amino acid sequence as set forth in SEQ ID NO: 121, and a light chain variable region comprising light chain CDR1 having the amino acid sequence as set forth in SEQ ID NO: 122, light chain CDR2 having the amino acid sequence as set forth in SEQ ID NO: 123, and light chain CDR3 having the amino acid sequence as set forth in SEQ ID NO: 124;

(14) an antibody comprising a heavy chain variable region comprising heavy chain CDR1 having the amino acid sequence as set forth in SEQ ID NO: 125, heavy chain CDR2 having the amino acid sequence as set forth in SEQ ID NO: 126, and heavy chain CDR3 having the amino acid sequence as set forth in SEQ ID NO: 127, and a light chain variable region comprising light chain CDR1 having the amino acid sequence as set forth in SEQ ID NO: 128, light chain CDR2 having the amino acid sequence as set forth in SEQ ID NO: 129, and light chain CDR3 having the amino acid sequence as set forth in SEQ ID NO: 130;

(15) an antibody comprising a heavy chain variable region comprising heavy chain CDR1 having the amino acid sequence as set forth in SEQ ID NO: 131, heavy chain CDR2 having the amino acid sequence as set forth in SEQ ID NO: 132, and heavy chain CDR3 having the amino acid sequence as set forth in SEQ ID NO: 133, and a light chain variable region comprising light chain CDR1 having the amino acid sequence as set forth in SEQ ID NO: 134, light chain CDR2 having the amino acid sequence as set forth in SEQ ID NO: 135, and light chain CDR3 having the amino acid sequence as set forth in SEQ ID NO: 136;

(16) an antibody comprising a heavy chain variable region comprising heavy chain CDR1 having the amino acid sequence as set forth in SEQ ID NO: 137, heavy chain CDR2 having the amino acid sequence as set forth in SEQ ID NO: 138, and heavy chain CDR3 having the amino acid sequence as set forth in SEQ ID NO: 139, and a light chain variable region comprising light chain CDR1 having the amino acid sequence as set forth in SEQ ID NO: 140, light chain CDR2 having the amino acid sequence as set forth in SEQ ID NO: 141, and light chain CDR3 having the amino acid sequence as set forth in SEQ ID NO: 142;

(17) an antibody comprising a heavy chain variable region comprising heavy chain CDR1 having the amino acid sequence as set forth in SEQ ID NO: 143, heavy chain CDR2 having the amino acid sequence as set forth in SEQ ID NO: 144, and heavy chain CDR3 having the amino acid sequence as set forth in SEQ ID NO: 145, and a light chain variable region comprising light chain CDR1 having the amino acid sequence as set forth in SEQ ID NO: 146, light chain CDR2 having the amino acid sequence as set forth in SEQ ID NO: 147, and light chain CDR3 having the amino acid sequence as set forth in SEQ ID NO: 148;

(18) an antibody comprising a heavy chain variable region comprising heavy chain CDR1 having the amino acid sequence as set forth in SEQ ID NO: 149, heavy chain CDR2 having the amino acid sequence as set forth in SEQ ID NO: 150, and heavy chain CDR3 having the amino acid sequence as set forth in SEQ ID NO: 151, and a light chain variable region comprising light chain CDR1 having the amino acid sequence as set forth in SEQ ID NO: 152, light chain CDR2 having the amino acid sequence as set forth in SEQ ID NO: 153, and light chain CDR3 having the amino acid sequence as set forth in SEQ ID NO: 154;

(19) an antibody comprising a heavy chain variable region comprising heavy chain CDR1 having the amino acid sequence as set forth in SEQ ID NO: 155, heavy chain CDR2 having the amino acid sequence as set forth in SEQ ID NO: 156, and heavy chain CDR3 having the amino acid sequence as set forth in SEQ ID NO: 157, and a light chain variable region comprising light chain CDR1 having the amino acid sequence as set forth in SEQ ID NO: 158, light chain CDR2 having the amino acid sequence as set forth in SEQ ID NO: 159, and light chain CDR3 having the amino acid sequence as set forth in SEQ ID NO: 160;

(20) an antibody comprising a heavy chain variable region comprising heavy chain CDR1 having the amino acid sequence as set forth in SEQ ID NO: 161, heavy chain CDR2 having the amino acid sequence as set forth in SEQ ID NO: 162, and heavy chain CDR3 having the amino acid sequence as set forth in SEQ ID NO: 163, and a light chain variable region comprising light chain CDR1 having the amino acid sequence as set forth in SEQ ID NO: 164, light chain CDR2 having the amino acid sequence as set forth in SEQ ID NO: 165, and light chain CDR3 having the amino acid sequence as set forth in SEQ ID NO: 166;

(21) an antibody comprising a heavy chain variable region comprising heavy chain CDR1 having the amino acid sequence as set forth in SEQ ID NO: 167, heavy chain CDR2 having the amino acid sequence as set forth in SEQ ID NO: 168, and heavy chain CDR3 having the amino acid sequence as set forth in SEQ ID NO: 169, and a light chain variable region comprising light chain CDR1 having the amino acid sequence as set forth in SEQ ID NO: 170, light chain CDR2 having the amino acid sequence as set forth in SEQ ID NO: 171, and light chain CDR3 having the amino acid sequence as set forth in SEQ ID NO: 172;

(22) an antibody comprising a heavy chain variable region comprising heavy chain CDR1 having the amino acid sequence as set forth in SEQ ID NO: 173, heavy chain CDR2 having the amino acid sequence as set forth in SEQ ID NO: 174, and heavy chain CDR3 having the amino acid sequence as set forth in SEQ ID NO: 175, and a light chain variable region comprising light chain CDR1 having the amino acid sequence as set forth in SEQ ID NO: 176, light chain CDR2 having the amino acid sequence as set forth in SEQ ID NO: 177, and light chain CDR3 having the amino acid sequence as set forth in SEQ ID NO: 178;

(23) an antibody comprising a heavy chain variable region comprising heavy chain CDR1 having the amino acid sequence as set forth in SEQ ID NO: 179, heavy chain CDR2 having the amino acid sequence as set forth in SEQ ID NO: 180, and heavy chain CDR3 having the amino acid sequence as set forth in SEQ ID NO: 181, and a light chain variable region comprising light chain CDR1 having the amino acid sequence as set forth in SEQ ID NO: 182, light chain CDR2 having the amino acid sequence as set forth in SEQ ID NO: 183, and light chain CDR3 having the amino acid sequence as set forth in SEQ ID NO: 184;

(24) an antibody comprising a heavy chain variable region comprising heavy chain CDR1 containing the amino acid sequence as set forth in SEQ ID NO: 207, heavy chain CDR2 containing the amino acid sequence as set forth in SEQ ID NO: 208, and heavy chain CDR3 containing the amino acid sequence as set forth in SEQ ID NO: 209, and a light chain variable region comprising light chain CDR1 containing the amino acid sequence as set forth in SEQ ID NO: 210, light chain CDR2 containing the amino acid sequence as set forth in SEQ ID NO: 211, and light chain CDR3 containing the amino acid sequence as set forth in SEQ ID NO: 212.

(25) an antibody comprising a heavy chain variable region comprising heavy chain CDR1 containing the amino acid sequence as set forth in SEQ ID NO: 213, heavy chain CDR2 containing the amino acid sequence as set forth in SEQ ID NO: 214, and heavy chain CDR3 containing the amino acid sequence as set forth in SEQ ID NO: 215, and a light chain variable region comprising light chain CDR1 containing the amino acid sequence as set forth in SEQ ID NO: 216, light chain CDR2 containing the amino acid sequence as set forth in SEQ ID NO: 217, and light chain CDR3 containing the amino acid sequence as set forth in SEQ ID NO: 218.

(26) an antibody comprising a heavy chain variable region comprising heavy chain CDR1 containing the amino acid sequence as set forth in SEQ ID NO: 213, heavy chain CDR2 containing the amino acid sequence as set forth in SEQ ID NO: 214, and heavy chain CDR3 containing the amino acid sequence as set forth in SEQ ID NO: 247, and a light chain variable region comprising light chain CDR1 containing the amino acid sequence as set forth in SEQ ID NO: 216, light chain CDR2 containing the amino acid sequence as set forth in SEQ ID NO: 217, and light chain CDR3 containing the amino acid sequence as set forth in SEQ ID NO: 218.

(27) an antibody comprising a heavy chain variable region comprising heavy chain CDR1 containing the amino acid sequence as set forth in SEQ ID NO: 219, heavy chain CDR2 containing the amino acid sequence as set forth in SEQ ID NO: 220, and heavy chain CDR3 containing the amino acid sequence as set forth in SEQ ID NO: 221, and a light chain variable region comprising light chain CDR1 containing the amino acid sequence as set forth in SEQ ID NO: 222, light chain CDR2 containing the amino acid sequence as set forth in SEQ ID NO: 223, and light chain CDR3 containing the amino acid sequence as set forth in SEQ ID NO: 224.

(28) an antibody comprising a heavy chain variable region comprising heavy chain CDR1 containing the amino acid sequence as set forth in SEQ ID NO: 225, heavy chain CDR2 containing the amino acid sequence as set forth in SEQ ID NO: 226, and heavy chain CDR3 containing the amino acid sequence as set forth in SEQ ID NO: 227, and a light chain variable region comprising light chain CDR1 containing the amino acid sequence as set forth in SEQ ID NO: 228, light chain CDR2 containing the amino acid sequence as set forth in SEQ ID NO: 229, and light chain CDR3 containing the amino acid sequence as set forth in SEQ ID NO: 230.

(29) an antibody comprising a heavy chain variable region comprising heavy chain CDR1 containing the amino acid sequence as set forth in SEQ ID NO: 231, heavy chain CDR2 containing the amino acid sequence as set forth in SEQ ID NO: 232, and heavy chain CDR3 containing the amino acid sequence as set forth in SEQ ID NO: 233, and a light chain variable region comprising light chain CDR1 containing the amino acid sequence as set forth in SEQ ID NO: 234, light chain CDR2 containing the amino acid sequence as set forth in SEQ ID NO: 235, and light chain CDR3 containing the amino acid sequence as set forth in SEQ ID NO: 236.

In one aspect, the present invention provides an antibody which binds to human CLDN18.2 protein, comprising a heavy chain variable domain selected from the group consisting of SEQ ID NO: 1, 2, 3, 4, 5, 6, 7, 8, 9, 10, 11, 12, 13, 14, 15, 16, 17, 18, 19, 20, 21, 22, 23, 237, 238, 239, 240, 241, and 248, and in another aspect the present invention provides an antibody which binds to human CLDN18.2 protein comprising a light chain variable domain selected from the group consisting of SEQ ID NO: 24, 25, 26, 27, 28, 29, 30 31, 32, 33, 34, 35, 36, 37, 38, 39, 40, 41, 42, 43, 44, 45, 46, 242, 243, 244, 245, and 246.

In one embodiment, the antibody is humanized. In another embodiment, the CDR domains of the antibody have one, two, three, four or five amino acids substituted, mutated, deleted or added.

In one embodiment, the antibody is humanized, which comprises a light chain with an amino acid sequence at least 95%, at least 99%, or 100% identical as the one selected from SEQ ID NO: 193-197, 205 and 206, and a heavy chain with an amino acid sequence at least 95%, at least 99%, or 100% identical as the one selected from SEQ ID NO: 187-191, 199-203, and 204.

In one embodiment, the antibody is humanized, which comprises a light chain with an amino acid sequence at least 95%, at least 99%, or 100% identical as the one selected from SEQ ID NO: 252 and 253, and a heavy chain with an amino acid sequence at least 95%, at least 99%, or 100% identical as the one selected from SEQ ID NO: 249, 250 and 251.

In one embodiment, the antibody is humanized, which comprises a heavy chain variable domain with an amino acid sequence at least 95%, at least 99%, or 100% identical as the one selected from SEQ ID NO: 254-258, and 259, and a light chain variable domain with an amino acid sequence at least 95%, at least 99%, or 100% identical as the one selected from SEQ ID NO: 260, 261 and 262.

In one embodiment, the antibody is humanized, which comprises a heavy chain variable domain with an amino acid sequence at least 95%, at least 99%, or 100% identical as the one selected from consisting of SEQ ID NO: 263, 264, and 265, and a light chain variable domain with an amino acid sequence at least 95%, at least 99%, or 100% identical as the one selected from the group consisting of SEQ ID NO: 266, 267, 268 and 269.

In one embodiment, the antibody is selected from a single-chain Fv antibody (scFv), a Fab antibody, a Fab' antibody, a (Fab')2 antibody, a domain antibody, a nanobody, a minibody, a maxibody, and a diabody.

In one aspect, the above said antibody is conjugated with one or more cytotoxic agent. In one embodiment, the heavy chain and/or light chain of said antibody is fused with a human albumin; and wherein said albumin domain is conjugated with one or more cytotoxic agent.

In one aspect, the antibody is fused with an immunestimulant. In some embodiment, the heavy chain and/or light chain of said antibody is fused with one or more IL-2 polypeptides, one or more IL-2 analogs, one or more IL-15 polypeptides, or one or more IL-15 analogs. In some embodiment, said antibody further comprises one or more antagonists of IL-2 or IL-15. In some embodiment, the heavy chain and/or light chain of said antibody is fused with an antigen binding domain, and wherein said antigen binding domain binds human CD3. In some embodiment, the heavy chain and/or light chain of said antibody is fused with one or more antigen binding domains, and wherein said antigen binding domain binds human PD-L1, CD47 or signal-regulatory protein alpha (SIRPα).

In another aspect, the present invention provides a pharmaceutical composition comprising an antibody as described above.

In another aspect, the present invention provides a method of treating cancer, the method comprising the step of administering a pharmaceutical composition as described above to a subject in need thereof, wherein the cancer is selected from the group consisting of pancreas, stomach, esophagus, and liver cancer.

In another aspect, the present invention further provides a method of treating cancer, wherein the method comprising the step of administration of above said pharmaceutical composition to a patient in need thereof, and in combination of a chemotherapy regimen suitable for said cancer, wherein the cancer is selected from the group consisting of gastric, esophagus, pancreatic, and liver cancer.

In some embodiment, said chemotherapy regimen is selected from nucleoside analogs, platinum compounds, camptothecin analogs, taxanes, prodrugs thereof, salts thereof, and combinations thereof.

In some embodiment, said chemotherapy regimen consists of gemcitabine, 5-fluorouracil, oxaliplatin, irinotecan, paclitaxel, prodrugs thereof, salts thereof, and combinations thereof.

In some embodiment, said chemotherapy regimen consists of the combination of oxaliplatin and paclitaxel, or their prodrugs or salts.

BRIEF DESCRIPTION OF THE DRAWINGS

The accompanying drawings illustrate aspects of the present invention. In such drawings:

FIG. 8. FACS Analysis the Supernants from the Cultured Positive Hybridoma Subclones. FIG. 8A shows titration curves of the bindings of the supernants of the hybridomas to CLDN 18.2 expressed on HEK 293 cells. FIG. 8B shows the specificity of the bindings of the supernants to HEK 293 cells expressing CLDN 18.2 vs. 18.1. FIG. 8C shows the FACS intensity of the binding of the supernants to CLDN 18.2 vs CLDN 18.1 expressed on the HEK 293 cells.

FIG. 9. FACS Analysis of the Supernants of HEK 293 Cells Transiently Transfected with the Genes Cloned from Positive Subclones.

FIG. 11. Binding of the Humanized Antibodies to CLDN18.2 Expressed on HEK 293 Cells (FIG. 11A) and NUGC4 Gastric Cancer Cells (FIG. 11B) as Analyzed by FACS FIG. 12. Results of ADCC Reporter Assay for the Humanized Antibodies M5 and B with Target Cells HEK 293 Expressing CLDN 18.2 (FIG. 12A), Gastric Cancer Cells NUGC4 (FIG. 12B) and Gastric Cancer Cells DAN-G (FIG. 12C).

FIG. 13. CDC Results of the Humanized Molecules B, M1 and M5. FIG. 13A Shows the Results with B and M1 versus Reference against Target HEK293 Cells Expressing CLDN 18.2; FIG. 13B Shows the Results with M5 versus Reference against Target HEK293 Cells Expressing CLDN 18.2; FIG. 13C Shows the Results with B and M1 versus Reference against Target NUGC4 Cells.

FIG. 14. Specificity Results of the humanized mouse and rabbit antibodies. FIG. 14A shows the FACS binding of the humanized antibodies M1, M5 and B to claudin family proteins.

Figure 1:
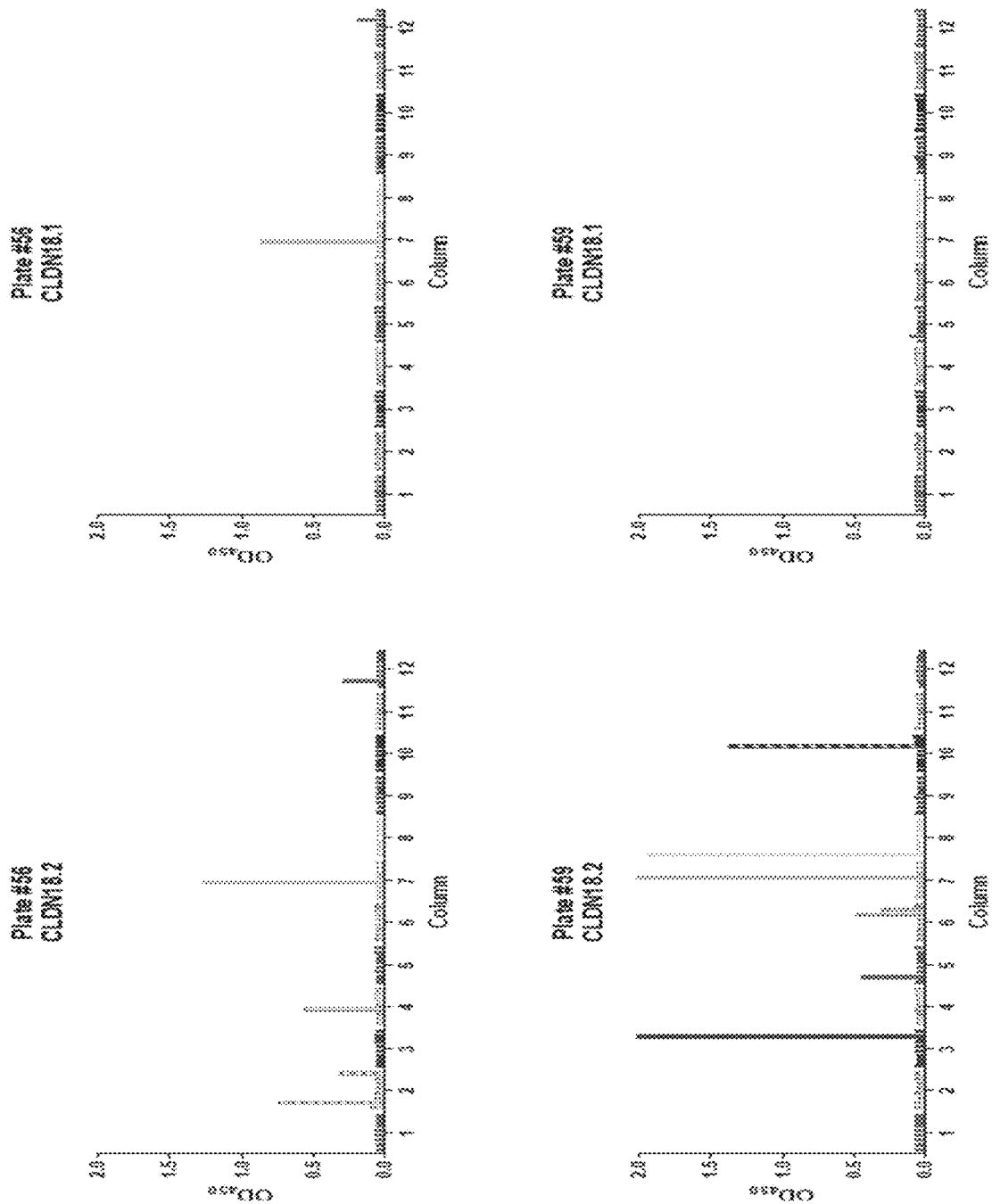
FIG. 1: ELISA-based screening of B cells. B cells selectively binding to CLDN 18.2 but not CLDN 18.1 were identified.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments

DETAILED DESCRIPTION

The present invention relates to compositions and methods for therapy of a subject afflicted with diseases such as cancer, which methods comprise administering to the subject a composition comprising a therapeutically effective amount of an anti-CLDN18.2 antibody or portion thereof that potentiates an endogenous immune response, either stimulating the activation of the endogenous response or inhibiting the suppression of the endogenous response. In one embodiment, an antibody is designated 49E05, 49E12, 50H08, 52E07, 52G02, 54B08, 54C02, 59A08, 59E07, 59F10, 59G03, 77B06, 80D08, 80G08, 81E11, 82C08, 82F02, 99A09, SD215, SD232, SD272, SD312, SD331, 79C4, 11E12, 83G3, 30B5, or 85H12. These antibodies have the respective CDRs listed in Tables 4-26, 29-32, and 33 below. In another embodiment, antibodies 49E05, 49E12, 50H08, 52E07, 52G02, 54B08, 54C02, 59A08, 59E07, 59F10, 59G03, 77B06, 80D08, 80G08, 81E11, 82C08, 82F02, 99A09, SD215, SD232, SD272, SD312, SD331, 79C4, 11E12, 83G3, 30B5, and 85H12 have the respective light and heavy chain variable regions as listed in Tables 2, 3, 34 and 35 below.

Hybridoma line 11E12 expressing an anti-CLDN18.2 antibody has been deposited with the American Type Culture Collection [ATCC; 10801 University Blvd., Manassas, Va. 20110-2209 (USA)] on Jun. 12, 2019, under Patent Deposit Number PTA-125950.

In certain other embodiments, the subject is selected as suitable for therapy in a method comprising measuring the surface expression of CLDN18.2 in a test tissue sample obtained from a patient with cancer, for example, determining the proportion of cells in the test tissue sample that express CLDN18.2 on the cell surface, and selecting the patient for therapy based on an assessment that CLDN18.2 is expressed on the surface of cells in the test tissue sample.

The claudin 18 (CLD18) molecule (Genbank accession number: splice variant 1 (CLD18A1): NP_057453, NM_016369, and splice variant 2 (CLD18A2): NM_001002026, NP_001002026) is an integral transmembrane protein with a molecular weight of approximately 27.9/27.7 KD. Claudins are integral membrane proteins located within the tight junctions of epithelia and endothelia.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The present composition encompasses amino acid substitutions in proteins and peptides, which do not generally alter the activity of the proteins or peptides (H. Neurath, R. L. Hill, The Proteins, Academic Press, New York, 1979). In one embodiment, these substitutions are "conservative" amino acid substitutions. The most commonly occurring substitutions are Ala/Ser, Val/Ile, Asp/Glu, Thr/Ser, Ala/Gly, Ala/Thr, Ser/Asn, Ala/Val, Ser/Gly, Ala/Pro, Lys/Arg, Asp/Asn, Leu/Ile, Leu/Val, Ala/Glu and Asp/Gly, in both directions.

As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Analogue as used herein denotes a peptide, polypeptide, or protein sequence which differs from a reference peptide, polypeptide, or protein sequence. Such differences may be the addition, deletion, or substitution of amino acids, phosphorylation, sulfation, acrylation, glycosylation, methylation, farnesylation, acetylation, amidation, and the like, the use of non-natural amino acid structures, or other such modifications as known in the art.

In one embodiment, an anti-CLDN18.2 antibody of the invention is designated as either 49E05, 49E12, 50H08, 52E07, 54B08, 54C02, 59A08, 59E07, 59F10, 59G03, 77B06, 80D08, 80G08, 81E11, 82C08, 82F02, 99A09, SD215, SD232, SD272, SD312, SD331, 79C4, 11E12, 83G3, 30B5, or 85H12 and each comprises a heavy chain CDR and a light chain CDR, wherein the heavy chain CDR comprises a sequence having at least 70%, at least 75%, at least 80%, at least 85%, at least 90%, at least 95%, at least 96%, at least 97%, at least 98%, at least 99% or 100% sequence identity to the respective CDRs listed in Tables 4-26 below, and wherein the light chain CDR comprises a sequence having at least 70%, at least 75%, at least 80%, at least 85%, at least 90%, at least 95%, at least 96%, at least 97%, at least 98%, at least 99% or 100% sequence identity to the respective CDRs listed in Tables 4-26 below.

In another embodiment, an anti-CLDN18.2 antibody of the invention designated as either 49E05, 49E12, 50H08, 52E07, 54B08, 54C02, 59A08, 59E07, 59F10, 59G03, 77B06, 80D08, 80G08, 81E11, 82C08, 82F02, 99A09, SD215, SD232, SD272, SD312, SD331, 79C4, 11E12, 83G3, 30B5, or 85H12 and each comprises a heavy chain variable region and a light chain variable region, wherein the heavy chain variable region comprises a sequence having at least 70%, at least 75%, at least 80%, at least 85%, at least 90%, at least 95%, at least 96%, at least 97%, at least 98%, at least 99% or 100% sequence identity to the respective heavy chain variable regions listed in Table 2 below, and wherein the light chain variable region comprises a sequence having at least 70%, at least 75%, at least 80%, at least 85%, at least 90%, at least 95%, at least 96%, at least 97%, at least 98%, at least 99% or 100% sequence identity to the respective light chain variable region selected from the ones listed in Table 3 below.

In a further embodiment an humanized anti-CLDN 18.2 antibody comprises a heavy chain and a light chain, wherein the heavy chain comprises a sequence having at least 95%, at least 96%, at least 97%, at least 98%, at least 99% or 100% sequence identity to the respective heavy chain variable region selected from SEQID NO: 187-191, 199-203, 204, 249, 250 and 251 listed in Table 27 below, and wherein the light chain comprises a sequence having at least 90%, at least 95%, at least 96%, at least 97%, at least 98%, at least 99% or 100% sequence identity to the respective light chain variable regions with SEQ ID NO: 193-197, 205, 206, 252 and 253 listed in Table 28 below.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology, Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

Accordingly, in either aspect of the invention, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., J Nucl Med 44:1962-9 (2003). In addition, these antibodies are advantageous because they can be engineered if necessary as different types of antibody fragments ranging from a small single chain Fv to an intact IgG with varying isoforms (Wu & Senter, Nat. Biotechnol. 23:1137-1146 (2005)). In some embodiments, the antibody fragment is part of a diabody. In some embodiments, in either aspect, the invention provides high avidity antibodies for use according to the invention.

The CDR regions provided by the invention may be used to construct an anti-CLDN18.2 binding protein, including without limitation, an antibody, a scFv, a triabody, a diabody, a minibody, and the like. In a certain embodiment, an anti-CLDN18.2 protein of the invention will comprise at least one CDR region from Tables 4-26 listed below or a sequence having at least 70%, at least 75%, at least 80%, at least 85%, at least 90%, at least 95%, at least 96%, at least 97%, at least 98%, at least 99% or 100% sequence identity to the CDR regions listed in Tables 4-26. Anti-CLDN18.2 binding proteins may comprise, for example, a CDR-H1, a CDR-H2, a CDR-H3, a CDR-L1, a CDR-L2, a CDR-L3, or combinations thereof, from an antibody provided herein. In particular embodiments of the invention, an anti-CLDN18.2 binding protein may comprise all three CDR-H sequences of an antibody provided herein, all three CDR-L sequences of an antibody provided herein, or both. Anti-CLDN18.2 CDR sequences may be used on an antibody backbone, or fragment thereof, and likewise may include humanized antibodies, or antibodies containing humanized sequences. In some embodiments, the CDR regions may be defined using the Kabat definition, the Chothia definition, the AbM definition, the contact definition, or any other suitable CDR numbering system.

In some embodiments, the invention provides antibodies (e.g., diabodies, minibodies, triabodies) or fragments thereof having the CDRs of Tables 4-26 or a sequence having at least 70%, at least 75%, at least 80%, at least 85%, at least 90%, at least 95%, at least 96%, at least 97%, at least 98%, at least 99% or 100% sequence identity to the CDRs of Tables 4-26. In other embodiments, the diabodies possess the light and heavy chain of Tables 2 and 3 or a sequence having at least 70%, at least 75%, at least 80%, at least 85%, at least 90%, at least 95%, at least 96%, at least 97%, at least 98%, at least 99% or 100% sequence identity to the sequences of Tables 2 and 3.

Diabodies, first described by Hollinger et al., PNAS (USA) 90(14): 6444-6448 (1993), may be constructed using heavy and light chains disclosed herein, as well as by using individual CDR regions disclosed herein. Typically, diabody fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VH and VL domains of another fragment, thereby forming two antigen-binding sites. Triabodies can be similarly constructed with three antigen-binding sites. An Fv fragment contains a complete antigen-binding site which includes a VL domain and a VH domain held together by non-covalent interactions. Fv fragments embraced by the present invention also include constructs in which the VH and VL domains are crosslinked through glutaraldehyde, intermolecular disulfides, or other linkers. The variable domains of the heavy and light chains can be fused together to form a single chain variable fragment (scFv), which retains the original specificity of the parent immunoglobulin. Single chain Fv (scFv) dimers, first described by Gruber et al., J. Immunol. 152(12):5368-74 (1994), may be constructed using heavy and light chains disclosed herein, as well as by using individual CDR regions disclosed herein. Many techniques known in the art can be used to prepare the specific binding constructs of the present invention (see, U.S. Patent Application Publication No. 20070196274 and U.S. Patent Application Publication No. 20050163782, which are each herein incorporated by reference in their entireties for all purposes, particularly with respect to minibody and diabody design).

Bispecific antibodies can be generated by chemical cross-linking or by the hybrid hybridoma technology. Alternatively, bispecific antibody molecules can be produced by recombinant techniques. Dimerization can be promoted by reducing the length of the linker joining the VH and the VL domain from about 15 amino acids, routinely used to produce scFv fragments, to about 5 amino acids. These linkers favor intrachain assembly of the VH and VL domains. Any suitable short linker can be used. Thus, two fragments assemble into a dimeric molecule. Further reduction of the linker length to 0-2 amino acids can generate trimeric (triabodies) or tetrameric (tetrabodies) molecules.

For preparation of antibodies, e.g., recombinant, monoclonal, or polyclonal antibodies, many techniques known in the art can be used (see, e.g., Kohler & Milstein, Nature 256:495-497 (1975); Kozbor et al., Immunology Today 4:72 (1983); Cole et al., in Monoclonal Antibodies and Cancer Therapy, Alan R. Liss, Inc., pp. 77-96 (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; and WO 92/200373).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332:323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity, neurodegeneration or pathological inflammation, normal human cells or tissues.

An "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer, infectious disease or neurodegenerative microenvironment.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

A "predetermined threshold value," relating to cell surface CLDN18.2 expression, refers to the proportion of cells in a test tissue sample comprising tumor cells and tumor-infiltrating inflammatory cells above which the sample is scored as being positive for cell surface CLDN18.2 expression. For cell surface expression, the predetermined threshold value for cells expressing CLDN18.2 on the cell surface ranges from at least about 0.01% to at least about 20% of the total number of cells. In preferred embodiments, the predetermined threshold value for cells expressing CLDN18.2 on the cell surface ranges from at least about 0.1% to at least about 10% of the total number of cells. More preferably, the predetermined threshold value is at least about 5%. Even more preferably, the predetermined threshold value is at least about 1%.

Construction of suitable vectors containing the desired sequences and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

Nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by readthrough transcription are also encompassed by this definition. Any products of a splicing reaction, including recombinant forms of the splice products, are included in this definition. An example of potassium channel splice variants is discussed in Leicher et al., J. Biol. Chem. 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Cancer" refers to human cancers and carcinomas, sarcomas, adenocarcinomas, etc., including but not limited to solid tumors, anal, kidney, breast, cardiac, cervical, ovarian, primary peritoneal, colorectal, lung, uterine, endometrial, esophageal, eye, fallopian tube, gall bladder, gastric, testicular, kidney, bladder, bile duct, bone, melanoma, karposi sarcoma, urinary tract, urethra, penis, vulva, vagina, cervical, parathyroid, penile, pituitary, colon, throat, thyroid, ovarian, prostate, mesothelioma, pancreas, rectal, stomach, brain, head and neck, small intestine, skin, uterine, testicular, esophagus, and liver cancer. Cancer can also include lymphomas and leukemias, including Burkitt lumphoma, Hodgkin lymphoma, non-Hodgkin lymphoma, cutaneious T-cell lymphoma, acute myeloid leukemia, acute lymphoblastic leukemia, hariy cell leukemia and acute myeloid leukemia. Lung cancer can include small cell lung cancer and non-small cell lung cancer.

In any of the embodiments above, one or more cancer therapies, e.g., chemotherapy, radiation therapy, immunotherapy, surgery, or hormone therapy can be co-administered further with the antibody of the invention.

In one embodiment, the chemotherapeutic reagent is an alkylating agent: nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin. In one embodiment the chemotherapeutic reagent is an anti-metabolites: the anti-folates (e.g., methotrexate), fluoropyrimidines (e.g., fluorouracil and capecitabine), deoxynucleoside analogues and thiopurines. In another embodiment the chemoptheraputic reagent is an anti-microtubule agent such as vinca alkaloids (e.g., vincristine and vinblastine) and taxanes (e.g., paclitaxel and docetaxel). In another embodiment the chemotherapeutic reagent is a topoisomerase inhibitor or a cytotoxic antibiotic such as doxorubicin, mitoxantrone, bleomycin, actinomycin, and mitomycin.

The contacting of the patient with the antibody or antibody fragment, can be by administering the antibody to the patient intravenously, intraperitoneally, intramuscularly, intratumorally, or intradermally. In some embodiments the antibody is co-administered with a cancer therapy agent.

The term "refolding" as used herein refers to the process by which a protein structure assumes its functional shape or conformation. It is the physical process by which a polypeptide folds into its characteristic and functional three-dimensional structure from random coil. It takes place at a basic pH (typically pH 8.0-10.0, pH 8.5-10, or pH 8.5-9.6), a low temperature (typically 0.0° C. to 10.0° C. or 2.0° C. to 8.0° C.), preferably with the presence of a redox pair at suitable concentrations, and/or at the presence of oxygen, and/or at the presence of catalyst(s) such as copper ions at suitable concentration.

The term "recombinant" as used herein refers to a polypeptide produced through a biological host, selected from a mammalian expression system, an insect cell expression system, a yeast expression system, and a bacterial expression system.

The term "formulation" as used herein refers to the antibodies disclosed herein and excipients combined together which can be administered and has the ability to bind to the corresponding receptors and initiate a signal transduction pathway resulting in the desired activity. The formulation can optionally comprise other agents.

The present specification also provides a pharmaceutical composition for the administration to a subject. The pharmaceutical composition disclosed herein may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition disclosed herein, and other factors known in medicine.

The pharmaceutical composition including the antibody disclosed herein may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

The composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the peptide disclosed herein may be approximately 0.0001 jig to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

Moreover, the pharmaceutical composition may be administered alone or in combination or coincident with other pharmaceutical formulations showing prophylactic or therapeutic efficacy.

In still another aspect, the present specification provides a method for preventing or treating of cancer, infectious diseases or neurodegenerative diseases comprising the step of administering to a subject the chimeric protein or the pharmaceutical composition including the same.

As used herein, the term "prevention" means all of the actions by which the occurrence of the disease is restrained or retarded.

As used herein, the term "treatment" means all of the actions by which the symptoms of the disease have been alleviated, improved or ameliorated. In the present specification, "treatment" means that the symptoms of cancer, neurodegeneration, or infectious disease are alleviated, improved or ameliorated by administration of the antibodies disclosed herein.

As used herein, the term "administration" means introduction of an amount of a predetermined substance into a patient by a certain suitable method. The composition disclosed herein may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

In the present specification, the term "subject" is those suspected of having or diagnosed with cancer, a neurodegenerative or an infectious disease. However, any subject to be treated with the pharmaceutical composition disclosed herein is included without limitation. The pharmaceutical composition including the anti-CLDN18.2 antibody disclosed herein is administered to a subject suspected of having cancer, a neurodegenerative or an infectious disease.

The therapeutic method of the present specification may include the step of administering the composition including the antibody at a pharmaceutically effective amount. The total daily dose should be determined through appropriate medical judgment by a physician, and administered once or several times. The specific therapeutically effective dose level for any particular patient may vary depending on various factors well known in the medical art, including the kind and degree of the response to be achieved, concrete compositions according to whether other agents are used therewith or not, the patient's age, body weight, health condition, gender, and diet, the time and route of administration, the secretion rate of the composition, the time period of therapy, other drugs used in combination or coincident with the composition disclosed herein, and like factors well known in the medical arts.

In still another aspect, the present specification provides a use of the therapeutic protein or the pharmaceutical composition including the same in the preparation of drugs for the prevention or treatment of cancer, a neurodegenerative or an infectious disease.

In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.01 mg, at least 0.25 mg, at least 0.3 mg, at least 0.5 mg, at least 0.75 mg, at least 1 mg, at least 1.25 mg, at least 1.5 mg, at least 2 mg, at least 2.5 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 50 mg, at least 55 mg, at least 60 mg, at least 65 mg, or at least 70 mg. In one embodiment, a weekly dose may be at most 0.5 mg, at most 0.75 mg, at most 1 mg, at most 1.25 mg, at most 1.5 mg, at most 2 mg, at most 2.5 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 50 mg, at most 55 mg, at most 60 mg, at most 65 mg, or at most 70 mg. In a particular aspect, the weekly dose may range from 0.25 mg to 2.0 mg, from 0.5 mg to 1.75 mg. In an alternative aspect, the weekly dose may range from 10 mg to 70 mg.

In other aspects of this embodiment, an antibody herein reduces the severity of a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, an antibody herein reduces the severity of a cancer from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

An antibody disclosed herein may comprise a therapeutic compound in an amount sufficient to allow customary administration to a human or nonhuman mammal, including a human, a cat, a dog, a horse, a sheep, a cow, a goat, a pig or other animal.

Aspects of the present specification disclose, in part, treating a human or nonhuman mammalian individual suffering from a disease, including cancer. As used herein, the term "treating," refers to reducing or eliminating in a human or nonhuman, mammalian a clinical symptom of cancer; or delaying or preventing in a human or nonhuman, mammalian the onset of a clinical symptom of cancer. For example, the term "treating" can mean reducing a symptom of a condition characterized by cancer, including, but not limited to, reduction of the severity of the disease, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with cancer are well known and can be determined by a person of ordinary skill in the art by taking into account factors, including, without limitation, the location of the disease, the cause of the disease, the severity of the disease, and/or the tissue or organ affected by the disease. Those of skill in the art will know the appropriate symptoms or indicators associated with a specific type of disease, and will know how to determine if an individual is a candidate for treatment as disclosed herein.

In aspects of this embodiment, a therapeutically effective amount of an antibody of the present invention herein reduces the severity of a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of an antibody of the present invention herein reduces the severity of a cancer by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of an antibody of the present invention herein reduces the severity of a cancer by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, an antibody disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of an antibody disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an antibody disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of an antibody disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of an antibody disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of an antibody disclosed herein typically may be between about 50 mg/mL to about 1,000 mg/mL. In aspects of this embodiment, a therapeutically effective amount of an antibody disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

Dosing can be single dosage or cumulative (serial dosing), and can be readily determined by one skilled in the art. For instance, treatment of a cancer may comprise a one-time administration of an effective dose of a therapeutic compound or a pharmaceutical composition disclosed herein. Alternatively, treatment of a cancer may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of an antibody disclosed herein can be administered to an individual once daily for an indefinite period of time, or until the individual no longer requires therapy. A person of ordinary skill in the art will recognize that the condition of the individual can be monitored throughout the course of treatment and that the effective amount of an antibody disclosed herein that is administered can be adjusted accordingly.

In one embodiment, an antibody disclosed herein is capable of reducing the number of cancer cells or tumor size in an individual suffering from a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, an antibody is capable of reducing the number of cancer cells or tumor size in an individual suffering from a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In a further embodiment, an antibody and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of an antibody is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, an antibody disclosed herein reduces or maintains a cancer cell population and/or tumor cell size in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, an antibody disclosed herein reduces or maintains a disease or a cancer cell population and/or tumor cell size in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, an antibody disclosed herein reduces or maintains a cancer cell population and/or tumor cell size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

Typically, any individual who is a candidate for treatment is a candidate with some form of cancer, whether the cancer is benign or malignant, a tumor, solid or otherwise, a cancer call not located in a tumor or some other form of cancer. Pre-operative evaluation typically includes routine history and physical examination in addition to thorough informed consent disclosing all relevant risks and benefits of the procedure.

EXAMPLES

The following non-limiting examples are provided for illustrative purposes only in order to facilitate a more complete understanding of representative embodiments now contemplated. These examples are intended to be a mere illustration only and not to constitute a limitation on the scope of the invention.

Thus, these examples should not be construed to limit any of the embodiments described in the present specification. Generation of Rabbit Antibodies Against CLD18.2

Example 1. Expression and Purification of CLDN 18.1 and CLDN18.2

CLDN 18.2 and 18.1 were overexpressed in *E. coli* BL21 DE3 using Pet 28 vector (MilliporeSigma). Cell lysate in 25 mM Tris, 100 mM NaCl, pH7.5 was centrifuged under 2000×g for 20 min. The supernatant was further separated by ultracentrifugation 100,000×g for 1 hour to get membrane particles. 1% n-dodecyl-β-D-maltopyranoside (DDM) in lysate buffer was used to solubilize membrane at 4° C. overnight. Insolubilized membrane was removed by ultracentrifugation 100,000×g for 1 hour. Supernatant was loaded to HisPur Cobalt resin (Thermo Scientific) column in the presence of 15 mM imidazole. Washed the column with 0.1% DDM, 15 mM imidazole in PBS. The claudin protein was eluted using PBS with 0.05% DDM. 0.002% cholesteryl hemisuccinate tris salt (CHS), 200 mM imidazole. The purified proteins were stored at 2-8° C. for short term use or at −80° C. for longer term storage.

Example 2. Immunizations

New Zealand White rabbits were immunized with eukaryotic expression vectors, encoding human CLD18.2 or its fragments. The presence of antibodies directed against human CLD18.2 in sera of rabbit was monitored by FACS analysis. The immune fluorescence was determined using HEK293 cells transiently transfected with a nucleic acid encoding a construct comprising human CLD18.2. Rabbits with detectable immune responses were boosted by intraperitoneal injection of the purified CLDN18.2 protein and/or alternatively $1 \times 10^8$ HEK293 cells transiently transfected with a nucleic acid encoding human CLD18.2.

Example 3. B-Cell Cloning

Complete medium includes RPMI 1640 (Life Technologies, cat. #11875-119), 10% fetal bovine serum (Sciencell, cat. #0500), non-essential amino acids (Life Technologies, cat. #11140-050), sodium pyruvate (Life Technologies, cat. #11360-070), 2-mercaptoethanol (Life Technologies, cat. #21-985-023), and gentamicin (Life Technologies, cat. #15710-072). Rabbit thymocytes (Spring Valley Labs, Woodbine, MD) at $2 \times 10^6$/mL were cultured with $2 \times 10^6$/mL rabbit splenocytes (Spring Valley Labs, Woodbine, MD) in complete medium containing 10 ng/mL PMA (Sigma-Aldrich, cat. #P1585) and 0.5% PHA-m (ThermoFisher, cat. #10576-015) for 48 hours. Supernatant was 0.2 uM filtered and stored at −20° C.

A 60 mm petri dish was coated with 3 mL human CLDN18.2-his at 2 ug/mL in PBS and incubated overnight at 4° C. Coating solution was removed and 3 mL PBS/5% BSA was added to block at room temperature for 1-2 hours. The blocking solution was removed and the plate was washed 4 times with PBS. Single cell suspensions of splenic lymphocytes from immunized rabbit were added to the plate in 3 mL PBS/2.5% BSA, and incubated for 45 minutes at 4° C. The dish was then washed 5 times with PBS/BSA to remove non-adherent cells, and then the adherent cells were harvested into complete medium by scraping with a cell scraper.

Alternatively, splenic lymphocytes were panned using CLDN 18.1 and CLDN 18.2 proteins. The claudin proteins were biotinylated using EZ-Link™ NHS-PEG4 Biotinylation Kit from Thermo Asher Scientific, For the negative panning, single cell suspensions of splenic lymphocytes from immunized rabbit were resuspended in MACS buffer (PBS/0.5% BSA/2 mM EDTA) containing the biotinylated CLDN18.1 and incubated for 15 minutes at 4° C. Cells were washed 2× with MACS buffer and resuspended in MACS buffer+Miltenyi Biotec streptavidin microbeads. After a 15-minute incubation cells were washed and passed over a magnetic column (LS column, Miltenyi Biotec). Unbound cells were collected to be used in positive selection. Cells were resuspended in MACS buffer containing biotinylated CLDN18.2 and incubated for 15 minutes. Cells were washed 2× with MACS buffer, resuspended in MACS buffer+streptavidin microbeads and incubated for 15 minutes. Cells were washed once, then passed over a magnetic column (MS column, Miltenyi Biotec), Positively selected, bound cells were eluted and used for B cell cloning.

Figure 2:
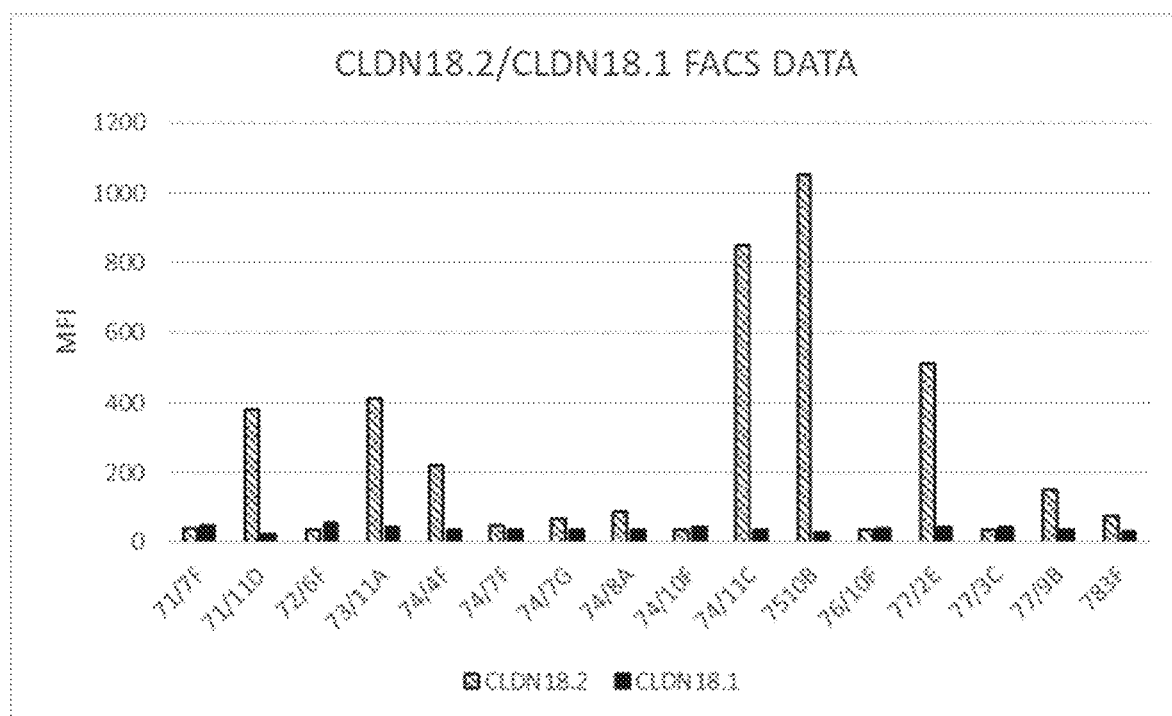
FIG. 2: FACS-based screening of B cell clones. Supernant from each clone was tested for their ability to bind to stable cell lines expressing CLDN18.2 (left) and CLDN18.1 (right) using FACS.

Cells were then plated into 96 well round-bottom plates at 10-50 cells/well in complete medium containing 2% rabbit spleen/thymus conditioned medium, human IL-2 (Prospec, cat. #cyt-095) at 5-10 ng/mL, Pansorbin (EMD Millipore, cat. #507858) at 1:20,000, and $5 \times 10^4$ mitomycin-c (Sigma-Aldrich, cat. #M4284) treated (50 ug/mL for 45 minutes) EL4-B5 cells/well. Plates were incubated for 7 days at 37° C. in CO2 incubator, supernatants were removed for ELISA and FACS analysis, and plates containing the cells were frozen at −80° C. for subsequent antibody v-region rescue. An example of the ELISA-based screening is given in FIG. 1. An example of the FACS-based screening is given in FIG. 2.

Example 4. Transient Transfection

Confirmation of successful v-region rescue was done by transfecting the heavy and light chains of the chimeric antibodies into HEK293 cells and testing the supernatant for recovery of CLDN18.2 binding activity. HEK293 cells were plated at $1.5 \times 10^5$ cells/well in 1 mL complete medium in a 24 well tissue culture plate, and cultured overnight. Transfection was performed using 500 ng heavy chain DNA and 500 ng light chain DNA with Lipofectamine 3000 (Life Technologies, cat. #L3000015) per manufacturer's instructions. Supernatants were harvested after 3-5 days and assayed for binding activity by ELISA.

Larger scale transfections to generate material for purification were performed with HEK293 cells cultured in 5% ultra-low IgG fetal bovine serum (Life technologies, cat. #16250-078) using Lipofectamine 3000 per manufacturer's instructions.

Example 5. CLDN18.2 Binding ELISA

B cell cloning supernatants were tested for binding to CLDN18.2 by ELISA. ELISA plates were coated with 100 uL antigen at 0.5 or 1 ug/mL in PBS (Life Technologies, cat. #14190-250) overnight at 4° C. or for 1 hour at 37° C. Both CLDN18.2 and 18.1 were expressed in *E. coli* and SF9 cells and partially purified using similar methods as described by Suzuki et al (Science 344, 304 (2014)). Plates were then blocked with PBS+10% goat serum for 1 hour. After washing with deionized water, samples were added in PBS/10% goat serum and incubated for 1 hour. Plates were washed, and 100 uL goat anti-rabbit IgG Fc-HRP (Jackson ImmunoResearch, cat. #111-035-046) was added at a 1:5000 dilution in PBS/10% goat serum for 1 hour. Plates were then washed with deionized water and 100 uL TMB substrate (Thermo Scientific, cat. #P1134021) was added to each well. Development was stopped with 100 uL 1N H2SO4, and OD450 was measured using a microplate spectrophotometer.

Purified chimeric and humanized antibodies were tested for binding to CLDN18.2 by ELISA. Protocols were the same as for testing B cell cloning supernatants.

Example 6. CLDN18.2 Binding as Tested by FACS

Stable HEK 293 cell lines expressing CLDN18.1 or CLDN 18.2 were cultured. The cells were detached with non-enzymatic cell dissociation solutions. Cells were counted and the cell density was adjusted to approximately 3 million cells/ml with FACS washing buffer, which comprised 3% FBS in PBS. 50 uL cells (150000 cells/well) were added into each well of a 96 well plate. Primary antibody or supernatant expressing the antibody of interest was added to the cells at prespecified concentration. The plate was incubated on ice for 1 hr. The plate was washed 3 times with the FACS washing buffer. Fluorescence conjugated secondary antibody was added to the cells (concentration depending on manufacture instruction). The plate was incubated on ice for 1 hr. The plate was washed again. PI staining solution was added at 0.1 ug/mL and the plate was incubated for 10 min on ice. The cell fluorescence was measured with Flow Cytometry instrument.

Example 7. Affinity Measurement

Figure 3:
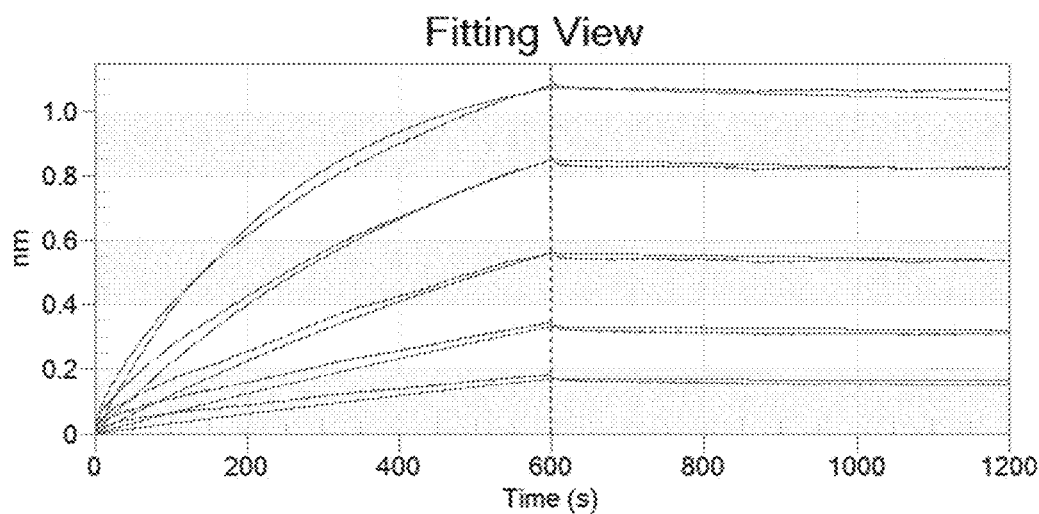
FIG. 3: Measurement of binding affinity between the antibodies and antigen CLDN 18.2. The binding kinetics for one particular clone (5) are shown in FIG. 3A and a Table illustrating the binding kinetics of selected clones is presented in FIG. 3B.

The affinity measurement was conducted with Octet RED 96 (ForteBio) instrument at 30° C. Briefly, anti-human IgG capture sensor (AHC from ForteBio cat #18-5060) was equilibrated with assay buffer (1× dilution of 10× Kinetics Buffer (ForteBio, Cat #18-5032). Test antibody samples were diluted to 2 microg/mL and allowed to bind to the sensors for 5 min. The sensors were then washed in assay buffer for 3 minutes, and CLDN18.2 ligand diluted at different concentrations were allowed to bind to the mAb coated on the sensors for 5 minutes. Afterwards, dissociation was followed for 10 minutes in the assay buffer. The sensors could be regenerated by washing in glycine buffer and assay buffer 3 times. The data were fitted with 1:1 binding model using the ForteBio software. An example of the affinity measurement is given in FIG. 3. Measurement of binding affinity between the antibodies and antigen CLDN 18.2. The example binding kinetics of Clone 5 is shown here. The parameters of the binding kinetics of the selected clones are shown in a table in FIG. 3.

Example 8. Antibody-Dependent Cellular Cytotoxicity (ADCC)

The ADCC Reporter assay was carried out following the protocol described below:
Material:
1. Culture medium—RPMI 1640, 10% fetal bovine serum, non-essential amino acids, sodium pyruvate, 50 uM beta-mercaptoethanol, penicillin/streptomycin;
2. Assay medium—Same as culture medium except use low IgG Fetal bovine serum
3. Effector Cell line—ADCC Bioassay effector cell line V variant (BPS Biosciences #60541)
4. Target cell line—HEK 293/18.2 (HEK 293 cells transfected with target antigen)
5. Target cell line—NUGC4 (gastric cancer cell line that expresses target antigen)
6. Pierce Firefly One-Step Glow assay kit #16196.
Assay Protocol:
1. Harvest target cell line. Plate 15,000 cells/well in 50 uL assay medium in white 96 well assay plates. Spin down effector cells and resuspend in assay medium. Culture overnight.
2. Prepare serial dilutions of test articles at 4× concentration in assay medium (typically dilution series starts at 16 ug/mL (4×), titer 3× dilutions 9 wells).
3. Transfer 25 uL of 4× sample to assay plate containing target cells. Incubate 15 minutes.
4. Harvest and count effector cells. Dispense 70,000 effector cells/well/25 uL. Incubate 5.5-6 hours.
5. Allow plate to cool to room temperature for 5 minutes.
6. Add 100 uL/well One-Step firefly luciferase reagent. Measure luminescence.

Figure 4A:
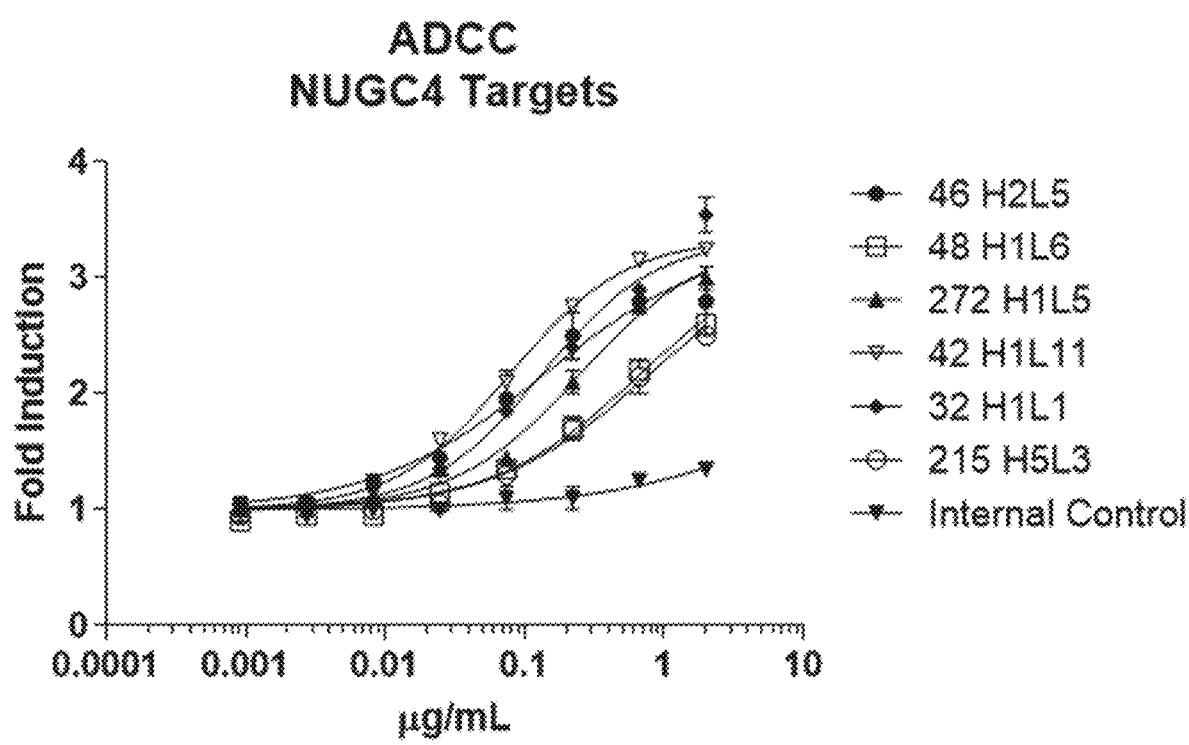
FIG. 4A: ADCC analysis of antibodies with tumor cell line NUGC4. Fold induction of cytotoxicity is shown on the Y-axis and the amount of different monoclonal antibodies tested plotted on the X-axis with the clones tested being 46H2L5 (full circle), 48H1L6 (full square), 272H1L5 (full triangle), 42H1L11 (full inverted triangle), 32H1L1 (full diamond), 215H5L3 (open circle), and control (full inverted triangle). In the experiment shown in this Figure, HEK293 cells were transfected with Human and mouse claudin18.2 and claudin18.1 for 72 hr before FACS analysis.
Figure 4B:
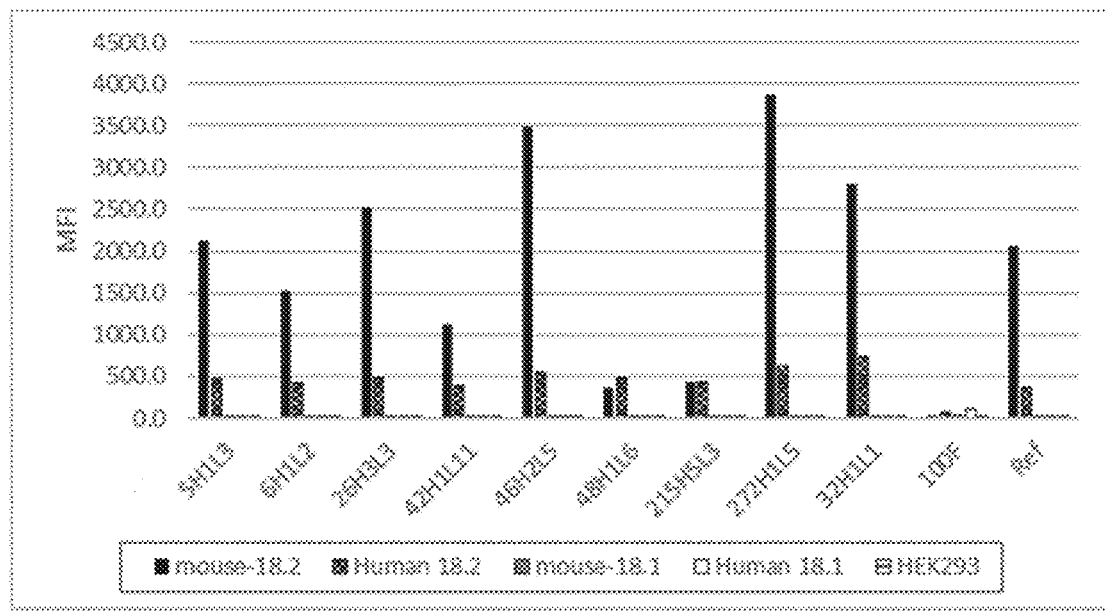
FIG. 4B shows the MFI for individual clones designated 5H1L3, 6H1L2, 26H3L3, 42H1L11, 46H2L5, 48H1L6, 215H5L3, 272H1L5, 32H1L1, and 100F are also shown for mouse −18.2, human 18.2, mouse 18.1, human 18.1, and HEK293. The quantified results are also presented in the table.

An example of the ADCC result is given in FIG. 4A, wherein ADCC analysis with tumor cell line NUGC4 had been carried out. FIG. 4B shows the MFI for individual clones designated 5H1L3, 6H1L2, 26H3L3, 42H1L11, 46H2L5, 48H1L6, 215H5L3, 272H1L5, 32H1L1, and 100F are also shown for mouse –18.2, human 18.2 mouse 18.1, human 18.1, and HEK293. The quantified results are also presented in the table presented in FIG. 4B.

Example 9. V-Region Rescue from Rabbit B-Cells and Screening of Chimeric Antibodies To rescue rabbit B-cells that were tested positive for CLDN18.2 binding, the IgG variable domain for both the heavy and light chains were captured by amplification using reverse transcriptase coupled polymerase chain reaction (RT-PCR) from mRNA isolated from positive B-cells. The VH and VL cDNAs thus obtained, were cloned and ligated onto human constant region constructs, such that the final cDNA construct encoded a chimeric rabbit human IgG.

Selected positive B-cells were lysed and mRNA prepared using the Dynabeads mRNA DIRECT Micro Kit, from Life Technologies according to the manufacturer's instructions. To recover the v-regions, mRNA generated from a single antigen positive well is used in a OneStep RT-PCR Kit (Invitrogen) reaction for both the heavy and light chains according to the manufacturer's instructions. For the reactions, gene specific primers located in the constant regions of the heavy and light chains of the rabbit IgG molecule are used to generate a single strand cDNA, followed PCR and nested PCR to amply the variable domains with specific restriction sites added to the ends of PCR products. In-house vectors containing human gamma-1 heavy chain constant region and human kappa light chain constant regions with specific restriction sites were used for sub-cloning. After addition of the restriction sites, the PCR products were subjected to the relevant Restriction enzymes digestion, gel purified and ligated into the appropriate vector.

Following sub-cloning, the ligated DNA was transformed into competent *E. coli* DH5-alpha (Invitrogen). The entire transformation pool was cultured over-night in medium containing the appropriate antibiotic resistance. The cultured bacteria were split into two parts: one part for making plasmid DNA prep (Qiagen Miniprep Kit) for use in transient HEK293 expression of chimeric antibodies, and the other part saved for plating single colonies for DNA sequencing.

To generate the chimeric antibodies, HEK293 cells were co-transfected with the DNA of both heavy and light chain from a selected well. Supernatant was harvested after three to five days of cell culture and assayed for IgG and antigen binding by ELISA. To detect the presence of IgG in the transfection supernatant, an ELISA immunoassay is done which utilizes an anti-human IgG Fc capture antibody coated to an ELISA plate, followed by the supernatants and human IgG standard. Detection of Fc-captured antibody is obtained using an anti-human IgG (H&L)-HRP reagent and TMB substrate.

The isolated DNA preps that gave positive chimeric antibody expression and antigen binding functions were processed for DNA sequencing. It should be note that the isolated DNA plasmids at this stage may or may not be homogenous for one specific V-region, as selected wells may contain one or more different B-cell clones. To break the pool into single clones, *E. coli* DH5 alpha culture pool from which the DNA was isolated previously was plated to single colonies on agar plate containing the appropriate antibiotic. Multiple colonies were picked and processed for DNA production using a rolling circle DNA amplification kit (Templiphy, GE Healthcare) following manufacturer's instructions. The DNA generated from the Templiphy reactions was sequenced and subsequently analyzed to determine the complexity of V-regions for each well. In addition to making DNA, each clone of bacteria used for the Templiphy reaction was saved for future DNA isolation.

Based on the DNA sequence analysis, plasmid DNA preps were made from the corresponding single clone E. coli culture containing the unique IgG heavy chain or light chain sequences. These plasmids were then used to transform HEK293 again to screen for chimeric monoclonal antibody. In case that there were multiple heavy and light chain sequences obtained from the same B-cell well (wells not clonal), every possible combination of unique heavy and light chain pairs was transfected. Supernatants were harvested after three to five days, assayed for IgG and antigen binding by ELISA. After this deconvolution step, heavy and light chain combinations which retained the desired binding activity were selected for further functional analysis and then for humanization.

Properties and Sequence Information for Top Antibody Candidates

The top 13 antibodies with unique DNA sequences were characterized with the purified chimeric proteins. The results are summarized in Table 1.

The internal reference or the reference antibody used below comprises the same heavy chain and light chain sequences as that of Zolbetuximab. The reference antibody was transiently expressed in HEK 293 cells and purified using Protein A affinity chromatography column followed by ion exchange chromatography steps.

plasmids delivered by either Gene gun (Bio-rad) system or ID injection followed by Electroporation (BTX-Harvard Apparatus). Serum samples were taken prior to the first immunization and 2 weeks after the last immunization for the study of CLDN18.2-specific antibody responses. Mice with high specific titers were giving a final boost of HEK293 cells expressing CLDN 18.2 and euthanized 4 days later to isolate spleen aseptically. Single-cell suspension from the spleen were prepared, then fused with the SP2/0 myeloma cells by electrofusion (BTX-Harvard Apparatus). Two fusions were carried out with each with up to 10 mice. Culture supernatants were analyzed to screen hybridomas with binding to HEK 293 cells expressing CLDN18.2 but not CLDN18.1. Positive clones were expanded, single-cell cloned, and confirmed by multiple assays.

Figure 5A:
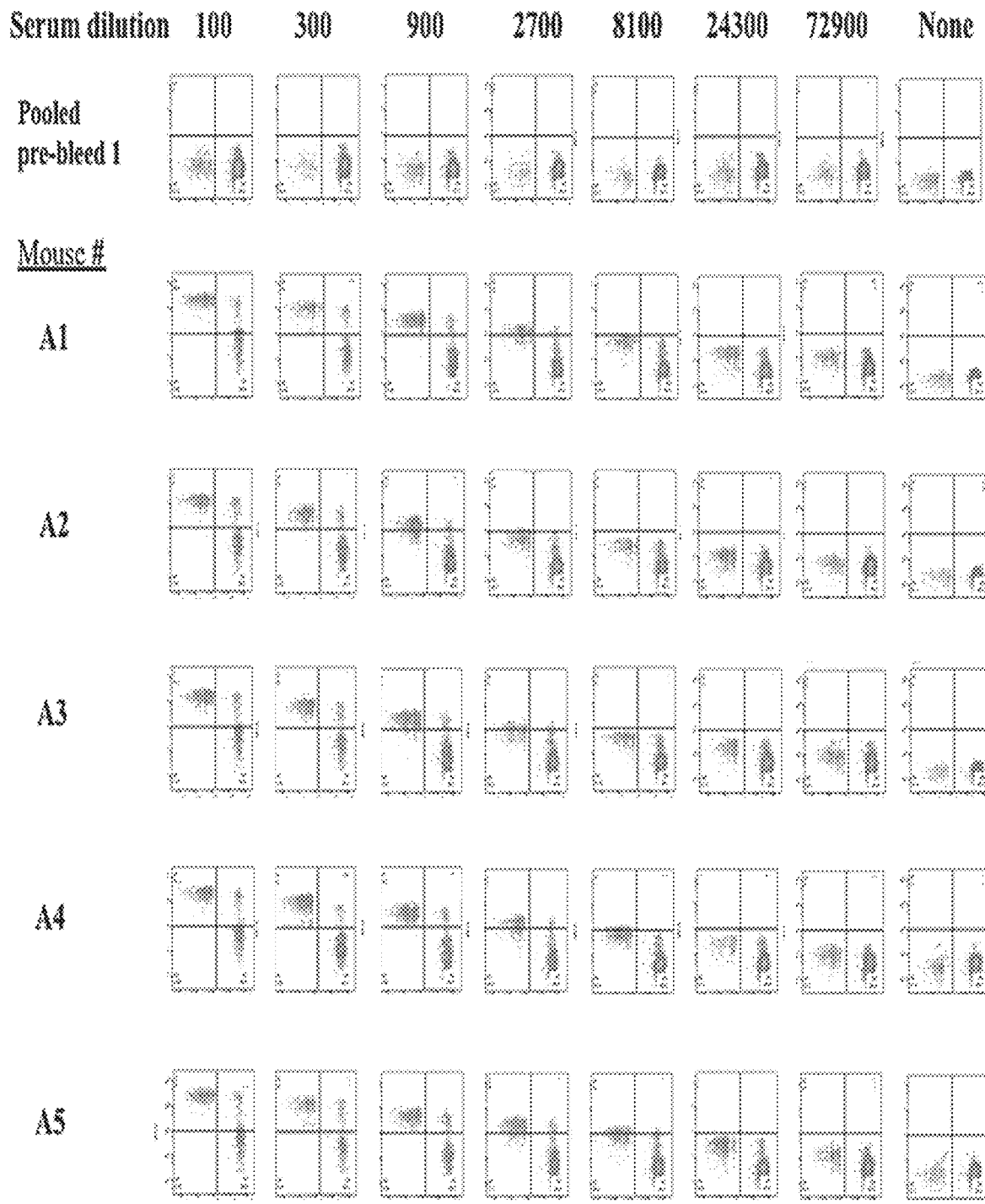
FIGS. 5A and 5B. Analysis of 20 Immunized Mice Serum Samples by FACS.
Figure 5A:
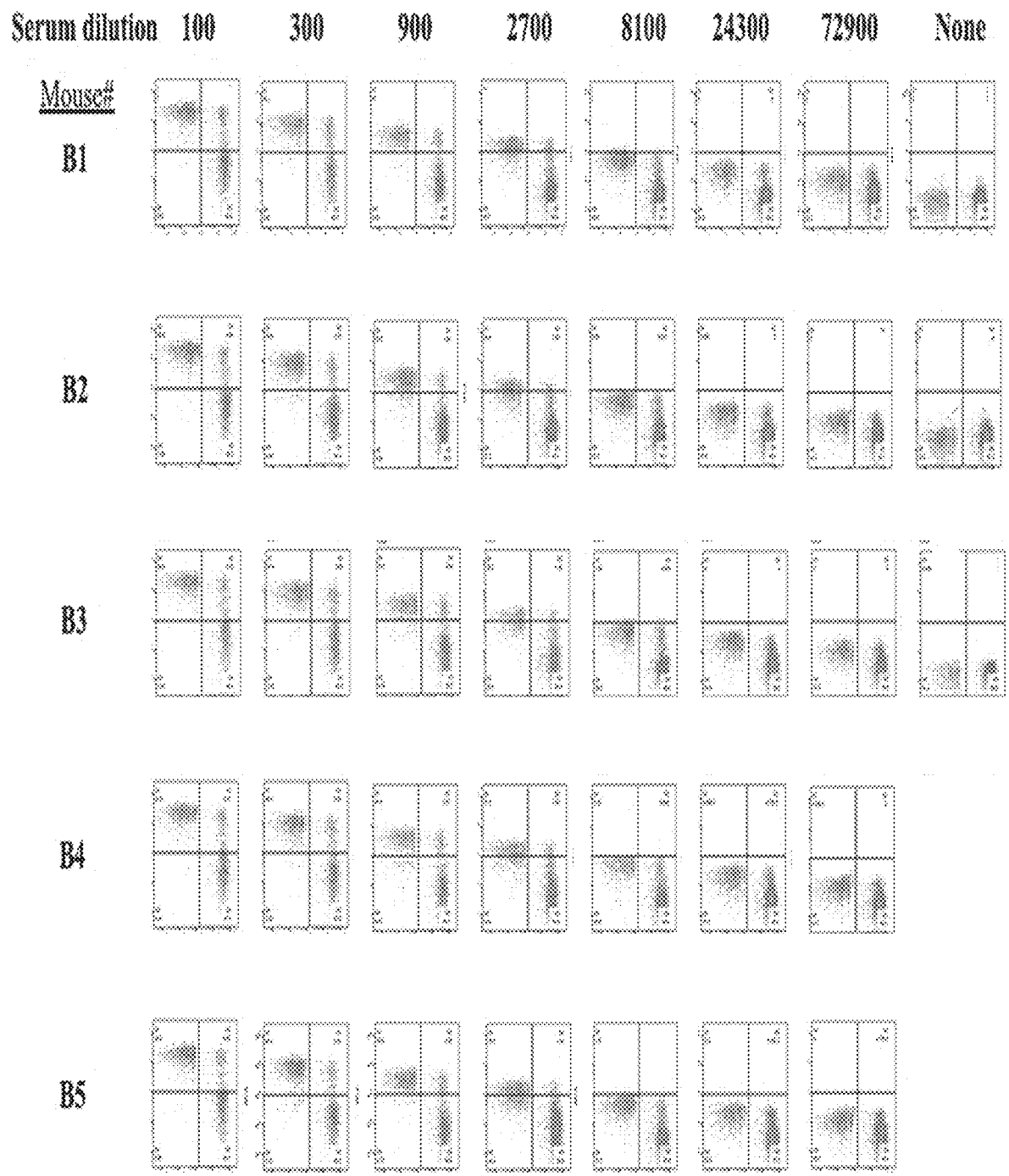
Figure 5B:
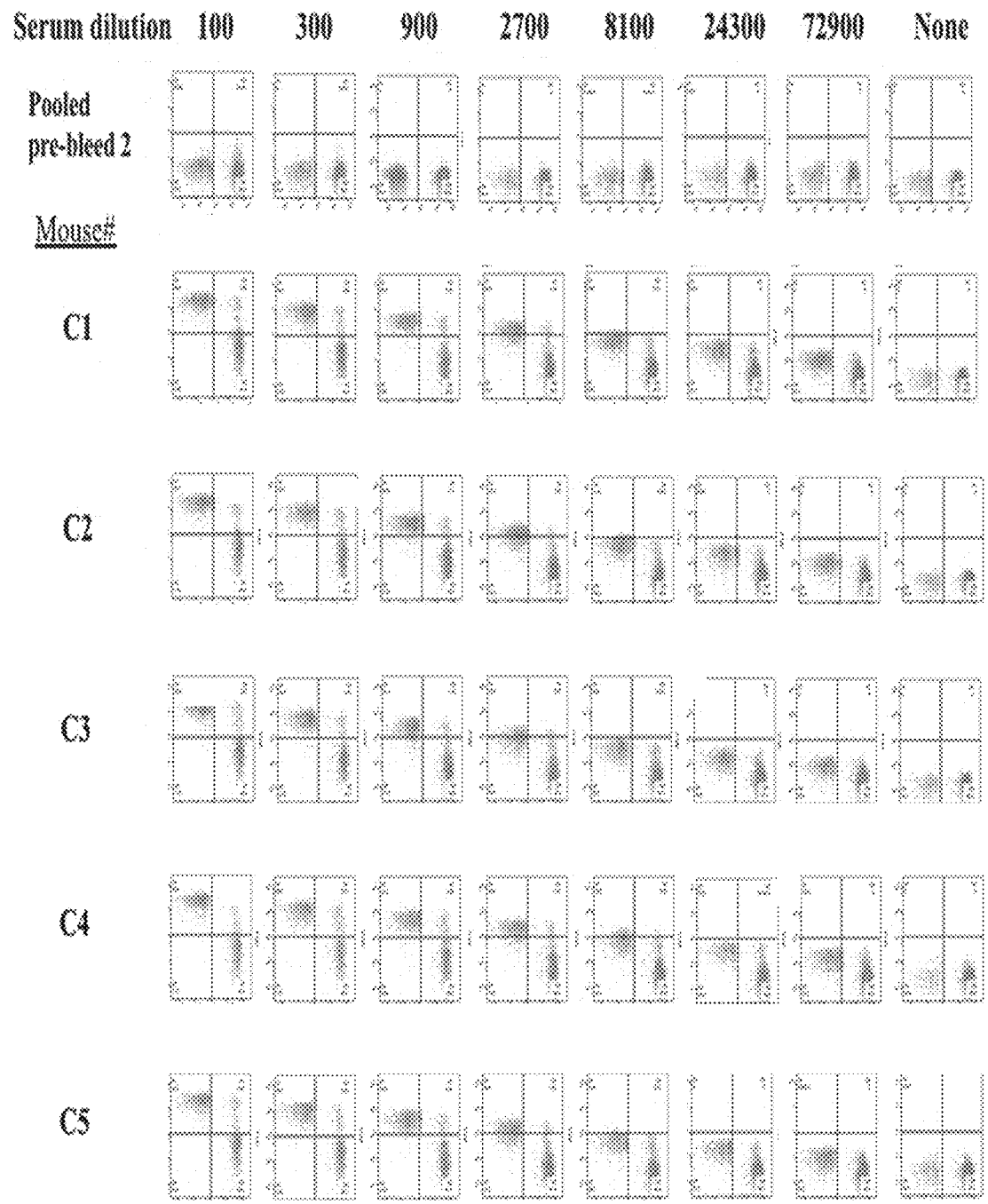
Figure 5B:
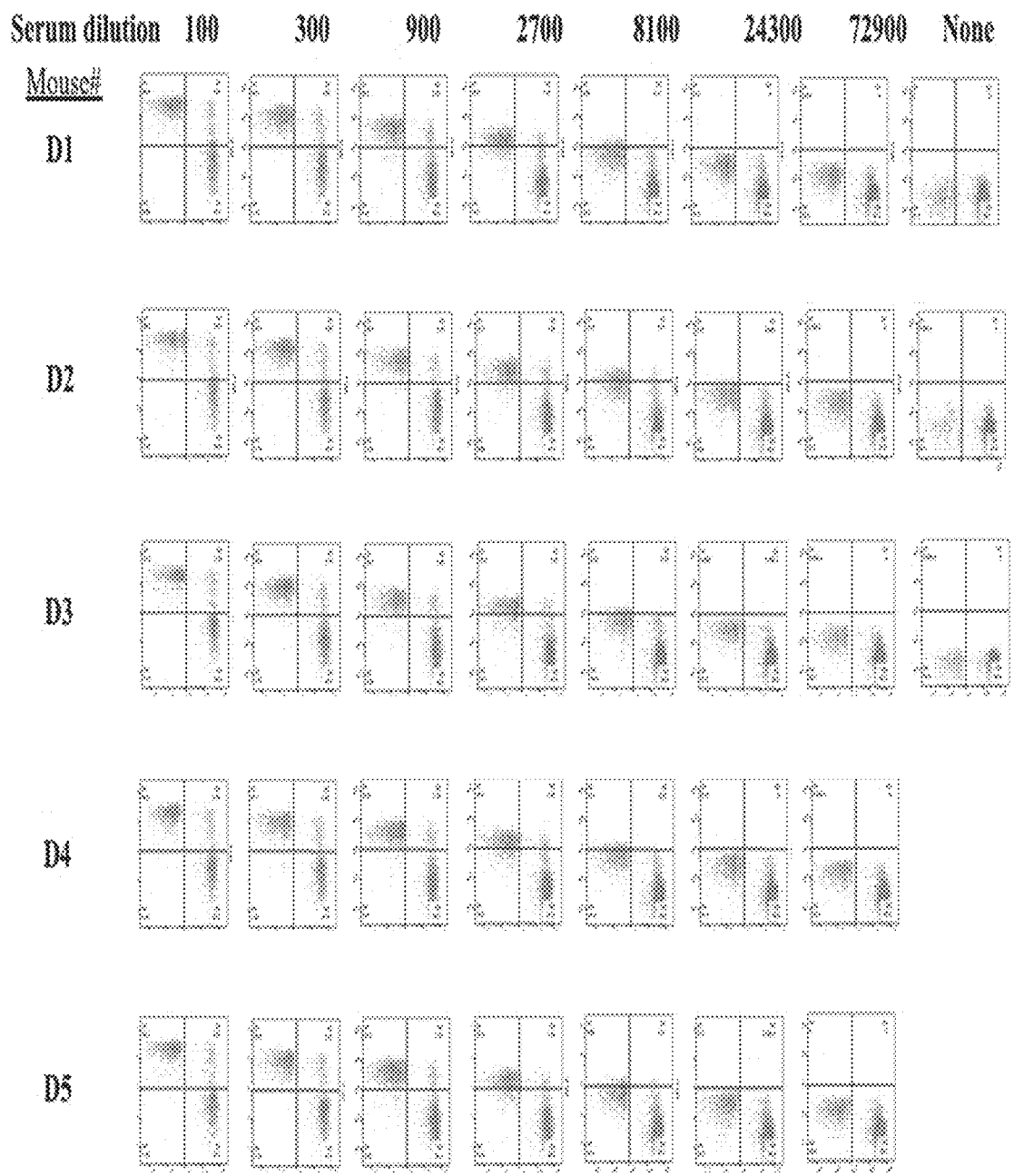

FIGS. 5A and 5B shows the results of CLDN18.2-specific antibody responses of the serum samples taken prior to the first immunization and 2 weeks after the last immunization as detected by FACS.

Figure 6:
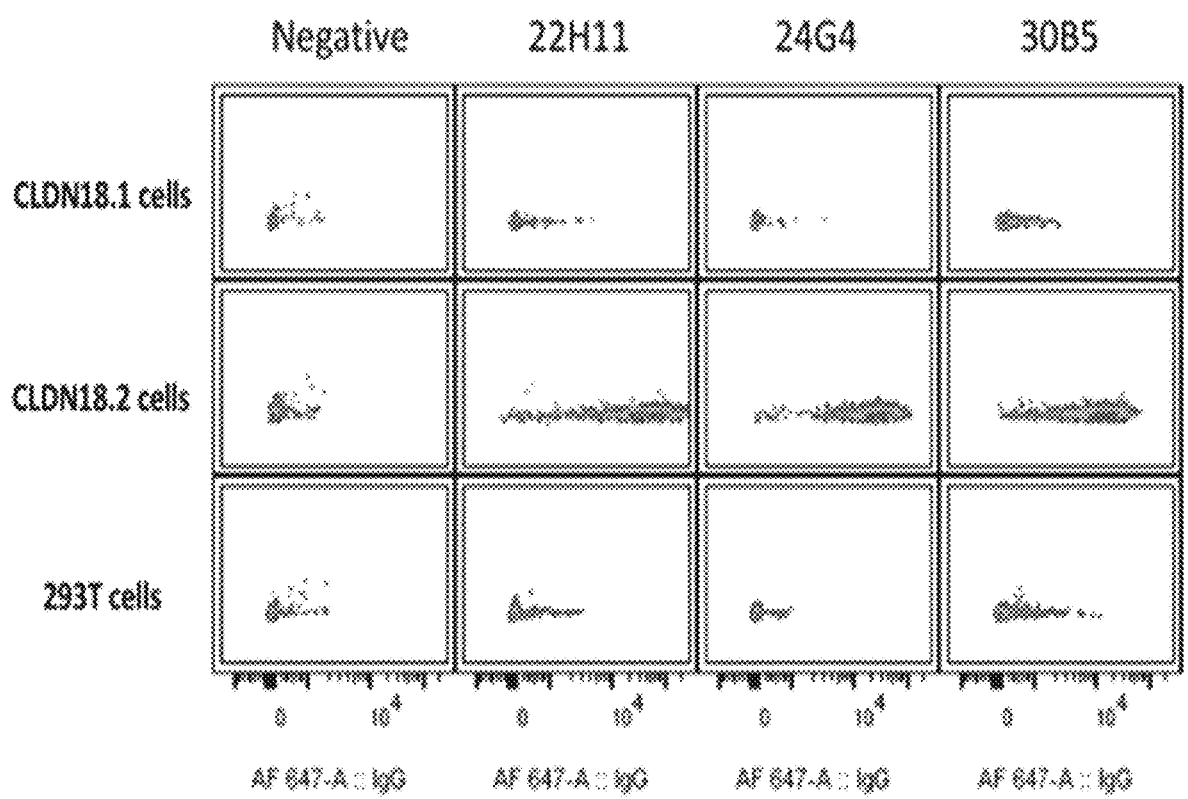
FIG. 6. FACS Screening of the First Fusion Identified Three Hybridomas Which Specifically Bound to CLDN 18.2 but Not CLDN 18.1.

FIG. 6 shows the results of the positive hybridomas from the first fusion identified by FACS analysis. A hybridoma was identified as positive when it showed binding to HEK293 cells expressing CLDN18.2 but with no or minimum binding to the HEK293 cells expressing CLDN18.1 or HEK293 cells.

Figure 7:
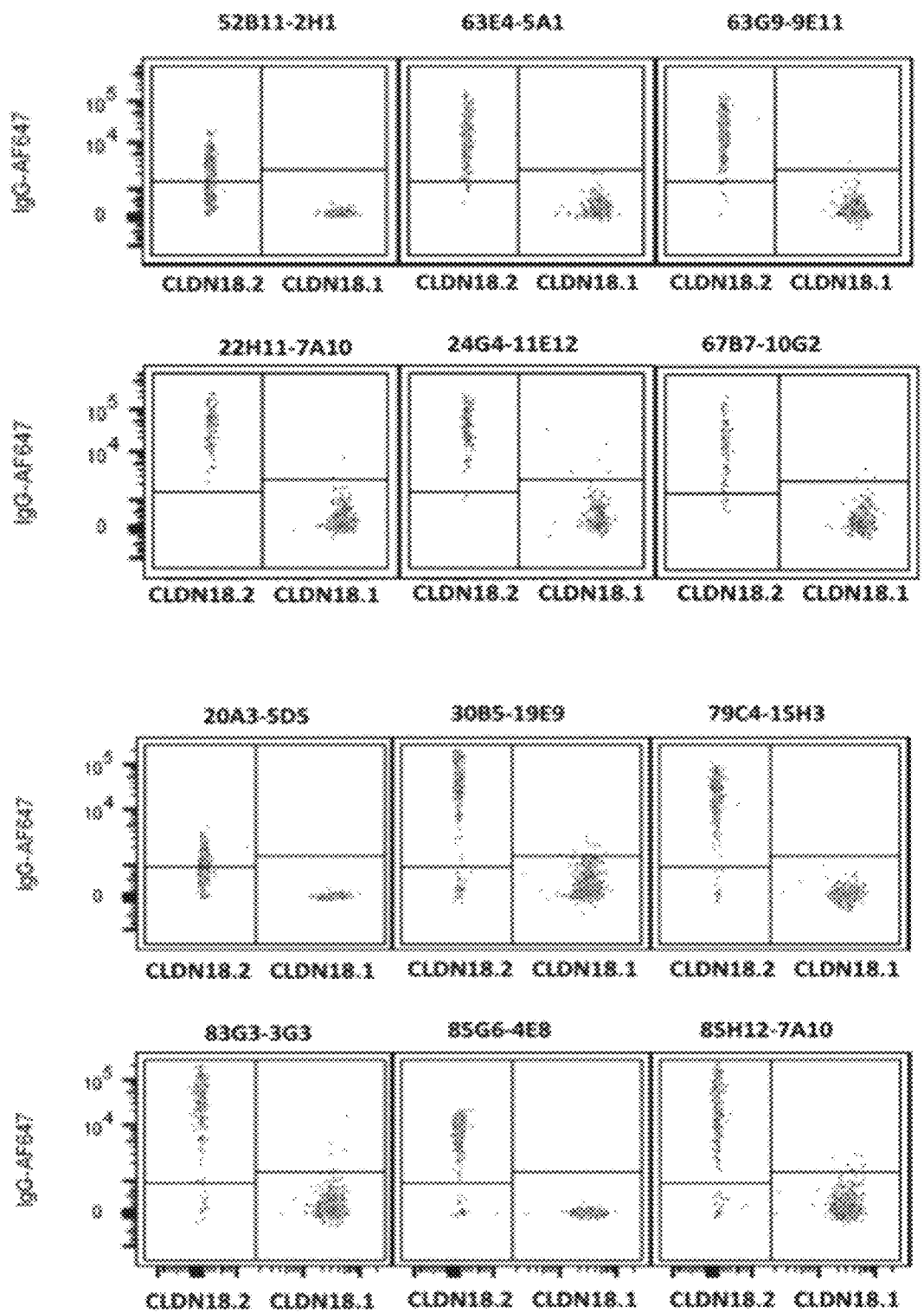
FIG. 7. FACS Analysis of Subclones of Positive Hybridomas Identified Clones Which Specifically Bound to CLDN 18.

The positive hybridomas from the two fusions were subcloned and the subclones were further screened for their selective binding to CLDN 18.2 vs CLDN 18.1. Twelve positive subclones were identified (FIG. 7). The hybridoma cells were expanded and vialed. The vials were frozen for further testing and subsequent cloning.

The hybridoma vials were thaw and cultured. And their supernants were further analyzed by FACS. FIG. 8A shows

TABLE 1

| Clone # | FACS EC50 (nM) | FACS Signal MFI (×1000) | ADCC with 293 cells expressing Claudin 18.2 (nM) | ADCC NUGC4 Cells (ng/ml) | KD (nM) (Binding Kinetics measured with ForteBio) |
|---|---|---|---|---|---|
| 6 | 0.46 | 43 | 0.014 | | 40 |
| 2 | 0.319 | 50 | 0.032 | | 123 (estimated) |
| 46 | 0.619 | 55 | 0.015 | 70 | 12 |
| 272 | 0.654 | 55 | 0.009 | 230 | 13 |
| 30 | 0.319 | 30 | 0.030 | | 30 |
| 42 | 0.417 | 35 | 0.012 | 80 | 30 |
| 5 | 1.055 | 44 | 0.044 | | 25 |
| 33 | 0.969 | 45 | 0.040 | | 16 |
| 9 | 4.22 | 18 | 0.017 | | 110 (estimated) |
| 26 | 1.08 | 40 | 0.035 | | 25 |
| 312 | | | 0.017 | | 10 |
| 31 | 1.06 | 20 | 0.044 | | 150 |
| 48 | 0.553 | 40 | 0.016 | 370 | 53 |
| Internal Reference | 1.17 | 25 | 0.014/.006 (results from two analysis) | 610 | 89/71 (results from two analysis) |

Generation of Mouse Antibodies Against CLD18.2

Example 10. Generation of Mouse Antibodies Against Human Claudin 18.2 (CLDN 18.2)

CLDN18.2-specific monoclonal antibodies (MAbs) were generated using the DNA immunization approach. Briefly, the CLDN18.2 gene insert was cloned into the modified DNA vaccine vector pJW4303. The DNA plasmid was then produced from Escherichia coli (HB101 strain) with a Mega purification kit (Qiagen, Valencia, CA). Twenty female 6-8 weeks old C57/B6 mice (Taconic Farms) each received multiple rounds of immunizations with CLDn18.2 encoding titration curves of the bindings of the supernants of the hybridomas to CLDN 18.2 expressed on HEK 293 cells, FIG. 8B shows the specificity of the bindings of the supernants to HEK 293 cells expressing CLDN 18.2 vs. 18.1, and FIG. 8C shows the FACS intensity of the binding of the supernants to CLDN 18.2 vs CLDN 18.1 expressed on the HEK 293 cells.

Example 11. Cloning of the Selected Clones

Positive subclones including 79C4, 11E12, 83G3, 30B5 and 85H12 were selected to be cloned. Antibody variable regions of the selected clones were cloned. The heavy chain variable domain sequences of the selected clones are shown in Table 34, the light chain variable domains in Table 35, and the CDR for each top candidate are provided Tables 29-33.

V-gene cloning was carried out using the procedure described below.

RNA extraction: 1×10E6 mouse hybridoma cells were collected by centrifuge at 900 g for 5 min. Total RNA was extracted by using RNeasy Mini Kit (Qiagen, Germany) following manufacture's protocol. RNA was quantified by NanoDrop 1000 (Thermo Fisher).

cDNA synthesis: iScript cDNA Synthesis Kit (Catalog 1708891, Bio-Rad) was used for cDNA synthesis. Briefly, in 20 uL reaction volume, 1 ug total RNA, 4 uL reaction buffer with random primers, 1 uL iScript reverse transcriptase and nuclease-free water (variable) were mixed. The reaction mix was incubated at 25° C. for 10 min, 46° C. for 30 min, and 95° C. for 1 min in a thermal cycler (Bio-Rad) as described in manufacture's protocol. Alternatively, SMARTer RACE 5'/3' Kit (Catalog 634858, Takara) was used to synthesis cDNA as described in manufacture's manual.

V-gene amplification: EMD Millipore Novagen Mouse Ig-Primer Set (Catalog 698313, EMD Millipore) and High Fidelity Platinum Taq DNA Polymerase (Catalog 11304011, Invitrogen) are used to amplify heavy chain and light chain variable regions. Briefly, in 50 uL reaction volume, 5 uL 10× reaction buffer, 1 uL 10 mM dNTP mix, 1 uL forward/reverse primers, 1 uL cDNA product, 0.2 uL DNA polymerase and nuclease-free water (fill to 50 uL) were mixed. The reaction mix was incubated in a thermal cycler (Bio-Rad) at 95° C. for 15 seconds, 55° C. for 15 seconds and 72° C. for 30 seconds for 30 cycles, then extended at 72° C. for another 5 min. PCR products were cloned into TOPO TA cloning vector (Catalog K457501, Invitrogen) and transformed in to *E. coli* Top10 competent cells as described in manufacture's manual. Single colonies were picked for sequencing by GeneWiz (South Plainfield, NJ 07080).

Figure 9A:
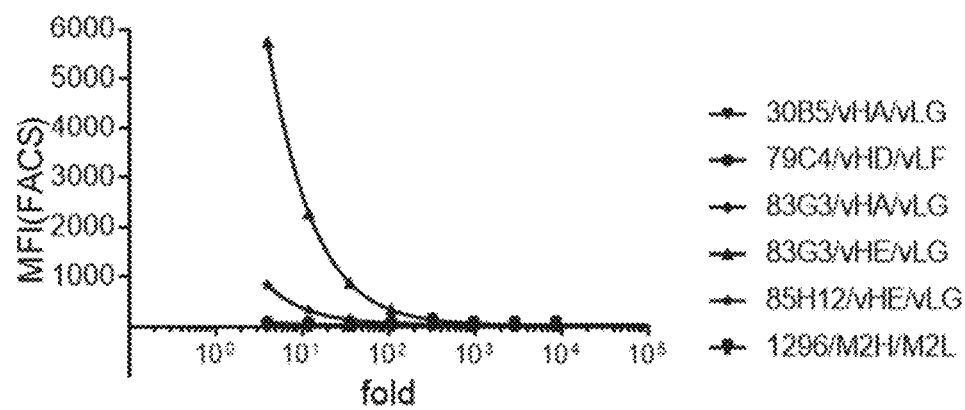
FIG. 9A shows titration curves of the bindings of the supernants of the clones to CLDN 18.2 expressed on HEK 293 cells.
Figure 9B:
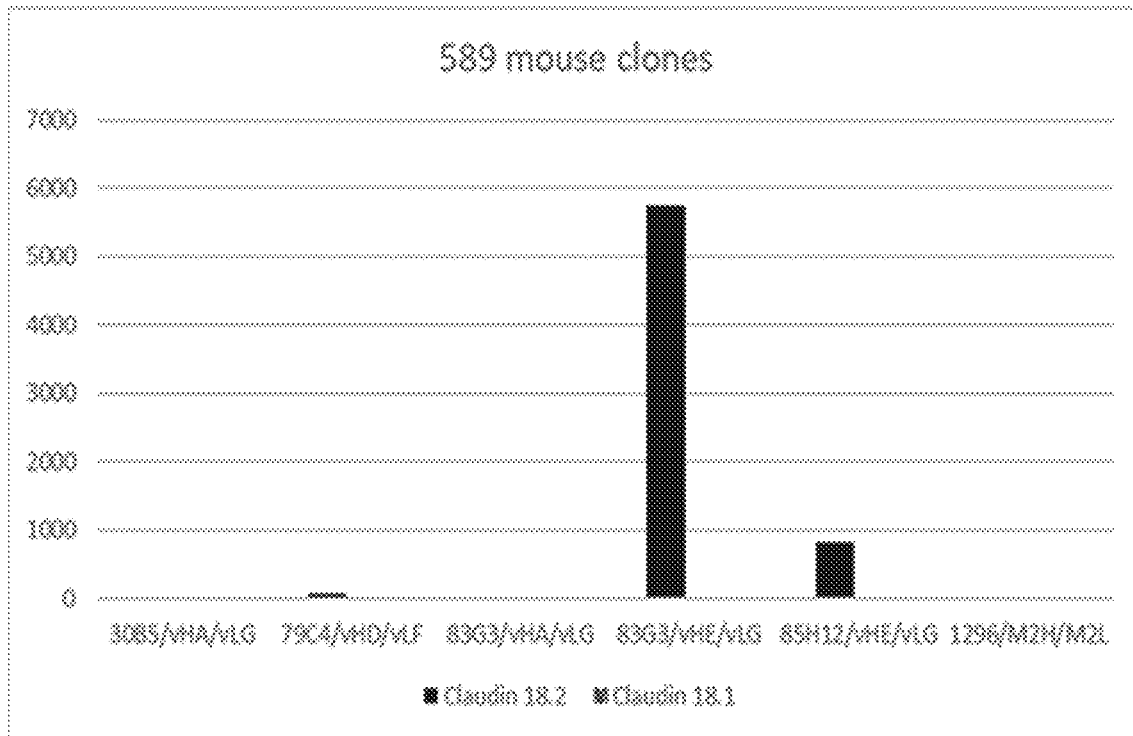
FIG. 9B shows the specificity of the bindings of the supernants to HEK 293 cells expressing CLDN 18.2 vs. 18.1.
Figures 9C, 10:
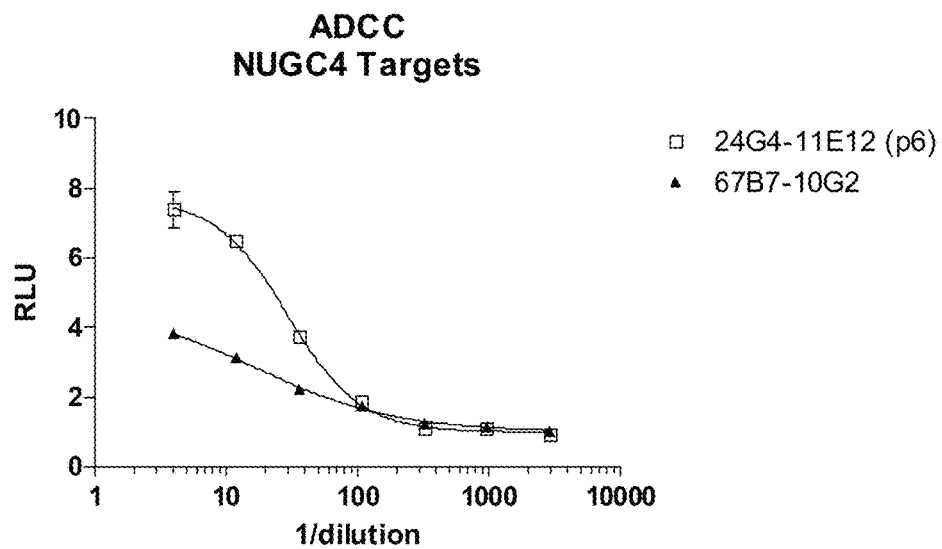
FIG. 9C shows the FACS intensity of the binding of the supernants to CLDN 18.2 vs CLDN 18.1 expressed on the HEK 293 cells.
FIG. 10. ADCC Reporter Assay of the Chimeric Molecules.

To confirm the sequences of the subclones, chimeric antibodies were generated. The heavy chain and light chain variable genes were cloned into pFUSEhIG1 and pFUSE-hIGK (InvivoGen, San Diego), respectively, for full antibody expression. HEK293 cells were co-transfected with the DNA of both heavy and light chain from each of the selected subclones. The supernants were test by FACS binding to HEK293 cells expressing CLDN18.2 vs HEK293 cells expressing CLDN 18.1. An example of the FACS analysis is shown in FIG. 9. FIG. 9A shows titration curves of the bindings of the supernants of the clones to CLDN 18.2 expressed on HEK 293 cells. FIG. 9B shows the specificity of the bindings of the supernants to HEK 293 cells expressing CLDN 18.2 vs. 18.1. FIG. 9C shows the FACS intensity of the binding of the supernants to CLDN 18.2 vs CLDN 18.1 expressed on the HEK 293 cells.

In addition, function analysis with ADCC reporter assay was also carried out following the protocol described in Example 8. An example of the ADCC reporter assay result is shown in FIG. 10.

Humanization of Selected Antibodies Against CLD18.2

Example 12. Humanization of the Rabbit Antibody Clone 46

Clone 46 was selected for humanization. Humanization was carried out using the standard CDR-grafting technologies coupled with the latest research on antibody structure and up-to-date database of mature human IgG sequences. A number of human framework sequences were identified that had been used as "acceptor" frameworks for the CDR sequences of Clone 46. These acceptor sequences had all come from mature Human IgG from a human source and not from phage display or other technologies. As a result, the humanized sequences were expected to be non-immunogenic and retained the canonical structure of the CDR-loops. Key residues important for the VH/VL interface and canonical loop structure have been maintained as much as possible in the humanized variants using the CDRx platform.

Five pairs of the humanized heavy chains (SEQ ID NO: 187-191, Table 27) and light chains (SEQ ID NO: 193-197, Table 28) were generated. All the possible pairs were expressed transiently with HEK293 cells and the supernatants of the transient expression were tested for binding and ADCC activity. Based on the initial results (data not shown), pairs of HC5/LC5, HC4/LC5, HC3/LC1, HC5/LC1, HC4/LC1 had the highest binding affinities and the ADCC activities. HC4 (SEQ ID NO: 190) and HC5 (SEQ ID NO: 191) were further optimized to generate SEQ ID NO: 199-201 for optimized HC4 and 202-204 for optimized HC5. LC chains LC1 (SEQ ID NO: 193) and LC5 (SEQ ID NO: 197) were also optimized to generate SEQ ID NO: 205 for optimized LC1 and SEQ ID NO: 206 for optimized LC5. After further screening, two lead molecules ASK589-B (or B) and ASK589-C (or C) were identified as the lead molecules from the humanized rabbit antibody. Molecule B comprises the heavy chain with an amino acid sequence as shown in SEQ ID NO: 202, and the light chain with an amino acid sequence as shown in SEQ ID NO: 205. Molecule C comprises the heavy chain with an amino acid sequence as shown in SEQ ID NO: 204, and the light chain with an amino acid sequence as shown in SEQ ID NO: 205.

Example 13. Humanization of the Mouse Antibody Clones 11E12 and 83G3

Mouse hybridoma clones 11E12 and 83G3 were selected for humanization. 11E12 Fv homology model was built up by using pdb 4OZ4 as model structure and humanization design was double checked with another hereo model built up on pdb 1HIL and pdb 3TT1. 83G3 Fv homology model was built up by using pdb 219L as model structure and humanization design was double checked with another hereo model built up on pdb 1MCP and pdb 219L. During the humanization process, mouse CDRs were grafted into the human framework acceptor, residues in human framework which are different from those in mouse framework were studied. Backmutations from human residue to mouse residue were designed based on the following rule: a. If new contact (ironical interaction, hydrogen bond, hydrophobic interaction) will be created between this human residue to mouse Fv CDR residue, canonical residue, interface residue or vernier residue, this human residue needs to be back-mutated to mouse residue; b. If an old contact (ironical interaction, hydrogen bond, hydrophobic interaction) between a mouse residue and canonical residue, interface residue or vernier residue will be lost when a human residue replacing a mouse residue, this human residue needs to be back mutated to mouse residue; and c. Replacement of mouse canonical residue, interface residue or vernier residue with human residue needs to be carefully studied and usually avoided.

Schrodinger surface analysis and Schrodinger post-translational modification of each antibody and huVHv1VLv1 (data from the humanized version with the highest humanization percentage) were also carried out. In addition, all potential cell epitope, B cell epitope, MHC II epitope and antigenicity epitope predicted by Protean 3D in the framework of the highest humanized version VHv1VLv1, which contained backmutations, were called out.

The variable domain sequences of the humanized 11E12 are listed in Table 36. The variable domain sequences of the humanized 83G3 are listed in Table 37.

The humanized antibodies were transient expressed in HEK 293 cells and purified as described above. The antibodies were further tested for their functionalities and specificity toward CLDN18.2. ASK589-M1 (or M1) was selected for further characterization. Molecule M1 comprises the heavy chain variable domain with an amino acid sequence as shown in SEQ ID NO: 254, and the light chain variable domain with an amino acid sequence as shown in SEQ ID NO: 260. M5 is the mutated version of M1, which comprises the heavy chain variable domain with an amino acid sequence as shown in SEQ ID NO: 257, and the light chain variable domain with an amino acid sequence as shown in SEQ ID NO: 260.

Functionality Analysis of the Humanized Antibodies Against CLD18.2

Example 14. Binding Assay

Binding of the humanized antibodies to the targets CLDN 18.2 proteins expressed on HEK293 cells and NUGC4 cells was analyzed by FACS. The results are shown in FIG. 11. FIG. 11A shows the binding to HEK293 cells transfected with CLDN18.2. The results showed that M5 had higher binding and higher binding affinity comparing to the reference molecule. FIG. 11B shows the binding to NUGC4 cells which naturally express CLDN18.2. The results showed that M5 and B had significantly higher binding and much higher binding affinity comparing to the reference molecule.

Example 15. ADCC Reporter Assay

The humanized antibodies were tested using the ADCC Reporter assay as described in Example 11. The results are shown in FIG. 12. FIG. 12A shows the results of ADCC Reporter Assay for the humanized antibodies M5 and B with target cells HEK 293 stably transfected with CLDN 18.2. The results indicated that M5 and B had slightly better or similar activities as that of the reference antibody on the HEK293 cells which had high levels of CLDN18.2 expressed on their surfaces. FIGS. 12B and C showed the results with gastric cancer cells NUGC4 (FIG. 12B) and DAN-G (FIG. 12C), which naturally express CLDN18.2 but at significantly lower levels comparing to HEK293 cells stably transfected with CLDN 18.2. The results showed that Molecules M5 and B had significantly higher ADCC activities than the reference antibody in killing the gastric cancer cells.

Example 16. CDC Assay

The CDC assay was carried out following using RPMI 1640+1% low-IgG fetal bovine serum as the assay medium. Titrate the test antibodies at 2× concentration in 50 uL/well assay medium. Add target cells at 20,000 cells/well in 25 uL. Incubate 15 minutes at 37° C. Add 25 uL/well 40% human complement (10% final concentration). For spontaneous cell death use targets with medium only. For maximum cell death use targets+1% Triton X-100. Incubate 1 hour at 37° C. Add 100 uL/well CellTiter-Glo (Promega cat. #G7571). Measure luminescence. The CDC activity is calculated using the following equation: Specific release=(experimental−spontaneous)/(maximum−spontaneous)*100.

FIG. 13 shows the CDC Results of the Humanized Molecules B, M1 and M5, as comparing to the reference antibody. FIG. 13A shows the results with B and M1 versus Reference against HEK293 cells expressing CLDN 18.2; FIG. 13B shows the results with M5 versus Reference against target HEK293 Cells Expressing CLDN 18.2; FIG. 13C shows the results with B and M1 versus Reference against target NUGC4 cells. All the results showed that antibodies M1, M5 and B had higher CDC activities than the reference antibody.

Specificity of the Humanized Antibodies M1, B and M5

Example 17. Binding to Other Claudin Family Members

Figure 14B:
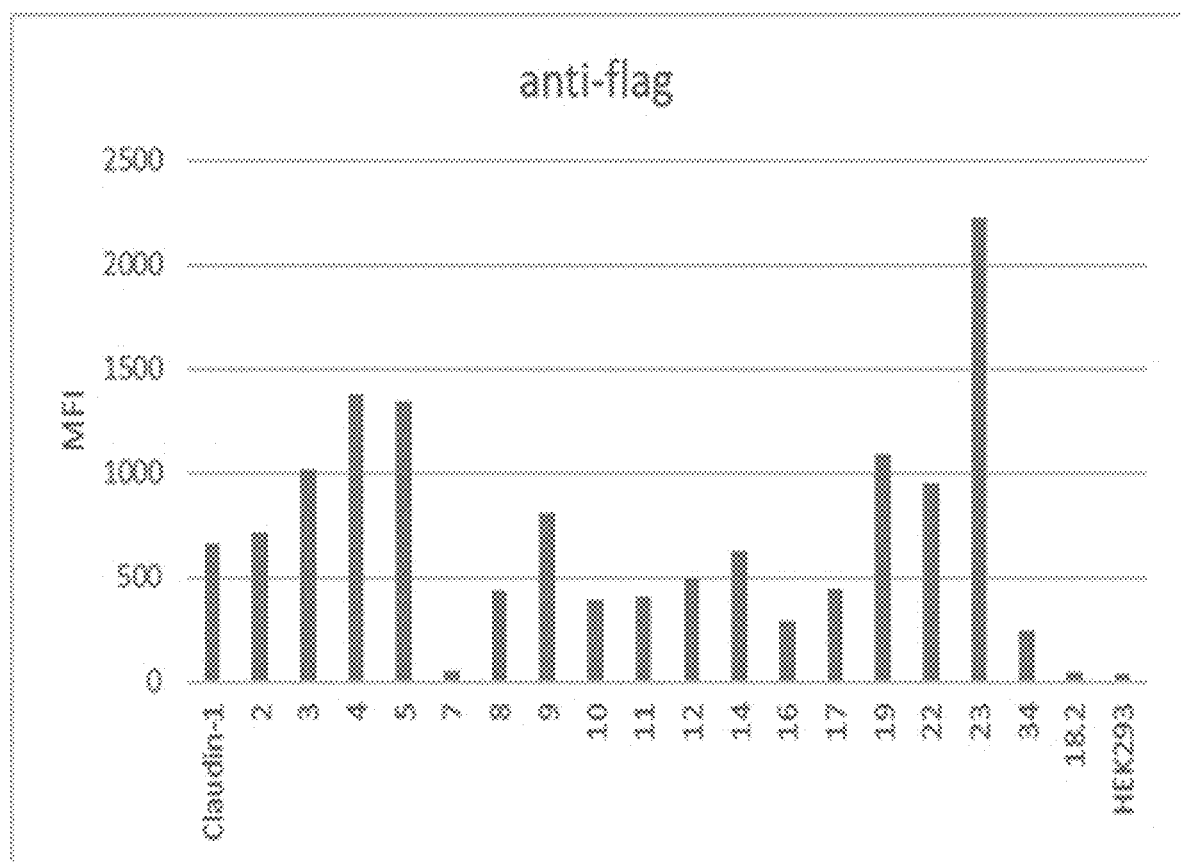
FIG. 14B shows the FACS binding of anti-FLAG antibody (Note that CLDN7 and CLDN18.2 molecules were not fused with FLAG).

The genes expressing a number of claudin family members were transiently transfected into the HEK 293 cells. All of the claudins except CLDN 7 and CLDN18.2 were also fused with a FLAG on the C-terminals. The binding of the antibodies M1, M5 and B as well as the reference antibody to the claudins expressed on the HEK 293 cells were tested using FACS as described above. The results showed that all the antibodies tested here selectively bound to CLDN18.2 but none of the other claudin family members shown here (FIG. 14A). The results also showed that all the claudins with FLAG were expressed as demonstrated by the binning of the FLAG antibody (FIG. 14B).

Example 18. Specificity Analysis Using Protein Chip

In order to test whether the humanized antibodies were specific for CLDN 18.2, the Membrane Proteome Array (MPA) assay was carried out for profiling the specificity of the antibodies which target human membrane protein CLDN 18.2. The MPA can be used to determine antibody target specificity, deconvolute orphan antibody targets, and characterize the target profile of biosimilar candidates. Membrane Proteome Array (MPA) assay was carried out similarly as described previously (Tucker et al PNAS May 29, 2018 115 (22) E4990-E4999). Flow cytometry was used to directly detect antibody binding to membrane proteins expressed in human HEK-293T cells. All MPA targets were designed to have native conformations and the appropriate post-translational modifications. The antibodies were tested for reactivity against the MPA library of over 5,300 human membrane proteins, including GPCRs, ion channels, and transporters. Identified targets were validated in secondary screens to confirm reactivity. The data (not shown) showed that M5 was specific binding to CLDN18.2 and did not unexpectedly bind to any of the membrane proteins in the test at a level above background.

PK Study

Example 19. Pharmacokinetics Study in Cyno Monkeys

The humanized antibodies M1, M5, B and C were tested in the Cyno PK study following the relevant government regulations using experimental animals. 10 male and 10 female animals with the body weights of 3-4 kg. The dosage was 5 mg/kg every week for a total of four doses. The study was designed to five groups as shown in the table below.

| Group | Dosage (mg/kg) | #of doses | #of animals | Sex | Testing Article | Conc. (mg/ml) | Dosing Duration (min) | Dosing flow rate (ml/kg/min) |
|---|---|---|---|---|---|---|---|---|
| A | 5 | 4 | 5 | 3M, 2F | ASKB589B_DS | 1 | 20 | 0.25 |
| B | 5 | 4 | 5 | 2M, 3F | ASKB589C_DS | 1 | 20 | 0.25 |
| C | 5 | 4 | 4 | 2M, 2F | ASK-M5_DS | 1 | 20 | 0.25 |
| D | 5 | 4 | 2 | 1M, 1F | M1_DS | 1 | 20 | 0.25 |
| E | 5 | 4 | 4 | 2M, 2F | 589R_DS | 1 | 20 | 0.25 |

Samples were taken as described in the table below.

| | |
|---|---|
| Sample | serum |
| Sample Handling | Whole blood (for PK, ~1 mL) samples were taken from the vein. The samples were labeled and put on ice. After the clotting, the samples were centrifuged at 2-8, 1200-1500 × g for 10-15 minute, |
| Sample Time Window | 2 h samples allow +5 min; 24 h~2 d samples allow +10 min; 4 d~7 d samples allow +30 min |
| # of PK samples | 300 |

PK samples were taken per schedule shown in the table below.

| | Time | Groups 1, 2, 3, 4, 5 |
|---|---|---|
| 1 | 0 min (prior to dosing) | ✓ |
| 2 | Right after dosing | ✓ |
| 3 | 2 h | ✓ |
| 4 | 24 h | ✓ |
| 5 | 2 d | ✓ |
| 6 | 4 d | ✓ |
| 7 | 7 d (prior to 2$^{nd}$ dosing) | ✓ |
| 8 | 14 d (prior to 3$^{rd}$ dosing) | ✓ |
| 9 | 21 d (prior to 4$^{th}$ doing) | ✓ |
| 10 | Right after 4$^{th}$ dosing | ✓ |
| 11 | 21 d-2 h | ✓ |
| 12 | 22 d | ✓ |
| 13 | 24 d | ✓ |
| 14 | 27 d | ✓ |
| 15 | 34 d | ✓ |

Note:
✓, indicates that the sample was taken

Figure 15:
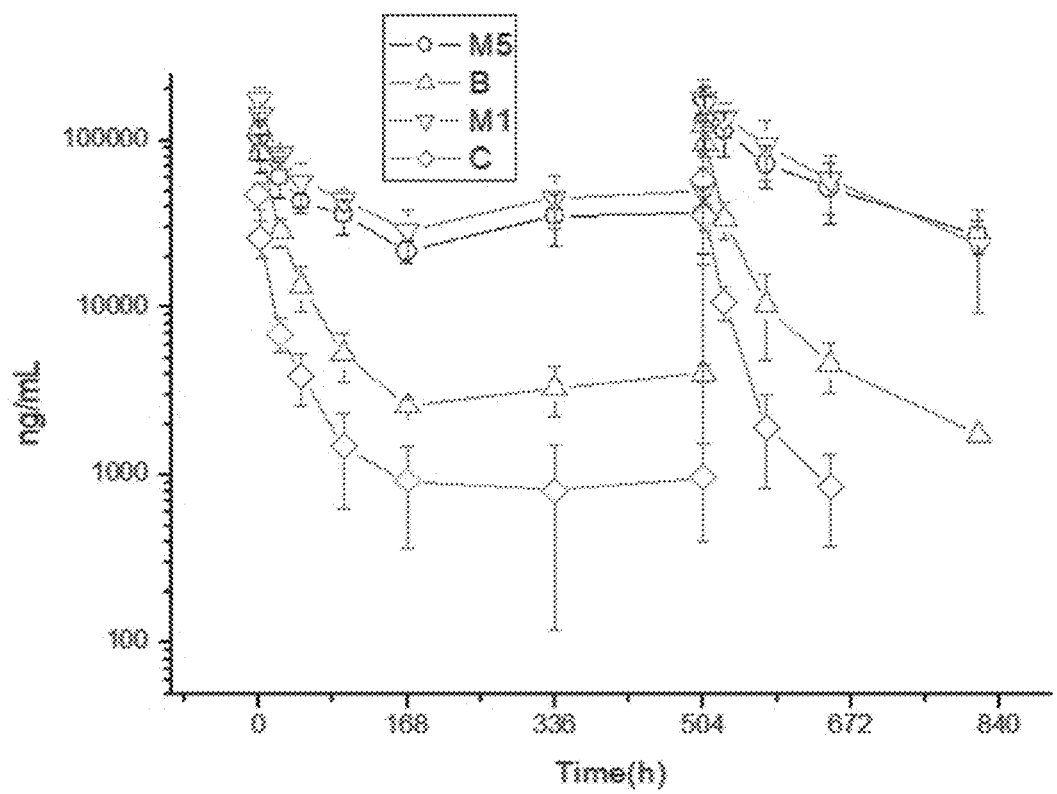
FIG. 15. Results from Cyno PK Study.

ELISA assay using the purified antigen was used to test the drug concentration in the serum. The PK data is shown in FIG. 15. The results showed that antibodies M1 and M5 had linear PK with no obvious immunogenicity at 5 mg/kg.

Animal Model Efficacy study

Example 20. Animal Model Efficacy Study

Mice used for the experiment were Balb/C female mice 6 weeks old. Mice were allowed to recover from shipping for 1 week prior to initiation of experiment. CT26/18.2 cells were implanted subcutaneously at 1×10$^6$ cells in 100 uL PBS. After 7 days tumors averaged ~70 mm$^3$. Mice were randomized into 6 groups of 10 mice such that each group had the same mean tumor size. Treatments were initiated at day 7.

The study groups are listed below:
1. Placebo
2. Mouse Antibody Reference (10 mg/Kg)
3. Mouse antibody M5 (10 mg/Kg)
4. Mouse antibody M5 (1 mg/Kg)
5. 5-Fluorouracil (40 mg/Kg)
6. 5-Fluorouracil+M5 (3 mg/Kg)

The antibodies in the forms of mouse IgG2a were expressed and purified. They were dosed every 3 days I.P. 5-FU was dosed every 2 days I.P. for a total of 3 treatments. The tumor sizes were measured every 3 days.

Figure 16:
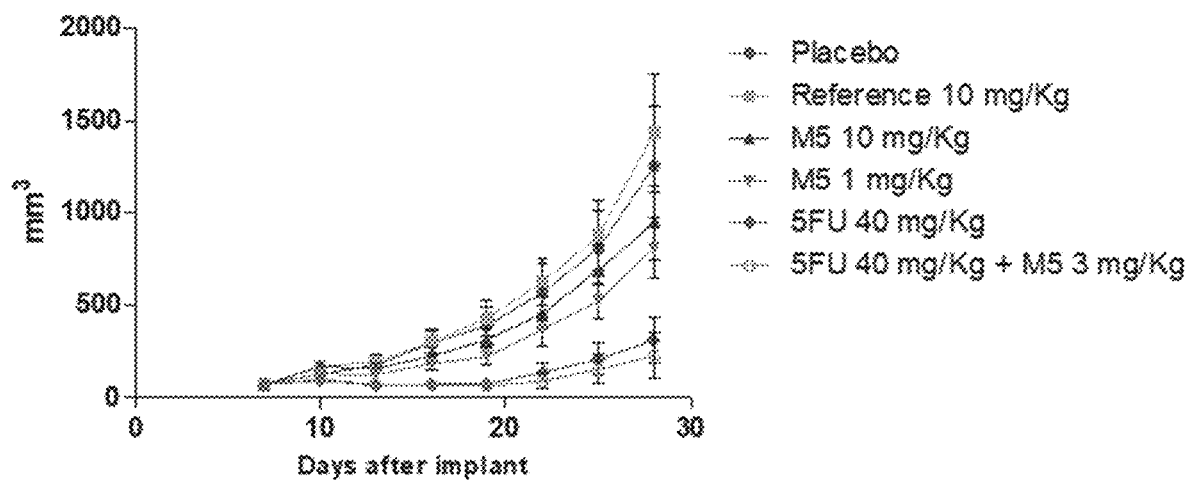
FIG. 16. Results from Animal Model Efficacy Study.

The in vivo efficacy data is shown in FIG. 16. The data showed that mouse antibody M5 was effective in suppressing tumor growth at 1 mg/kg and 10 mg/kg. The reference antibody did show any activities in this study.

TABLE 2

| SEQ ID NO: | Clone | Heavy chain variable domain Protein Sequence |
|---|---|---|
| 1 | 49E05 | CQSLEESGGGLVKPGGTLTLTCKASGIDFSSYYYMCWVRQAPGKGLEWIACIFNGDASTYYASWAHGRFTISKTSSTTVTLQMTGLTAADTATYFCARSDYSVAFAAFLYPTYFTLWGPGTLVTVSS |
| 2 | 49E12 | CQSLEESGGDLVKPGASLTLTCTASGFDLSSFVYICWVRQAPGKGLEWIGCIAINGGVTYYASWAKGRFTISKTSSTTVTLQMTSLTGADTATYFCARDDTSSNSYYNDLWGPGTLVTVSS |
| 3 | 50H08 | CQSLEESGGGLVQPGASLTLTCKASGFSFSSSYWICWVRQAPGKGLEWIACIYTTTSNIGYASWAKGRFTISKTSSTTVTLQMTSLTAADTATYFCAREDYDYYSFHPWGPGTLVTVSS |
| 4 | 52E07 | CQSLEESGGGLVQPEGSLTLTCTASGFSFSSSYWICWVRQAPGKGLEWIACVYTTTGNIGYASWAKGRFTISVPSSTTVTLQLTSLTAADTATYFCAREGSDIYAFHPWGPGTLVTVSS |
| 5 | 52G02 | QSLEESGGDLVKPGASLTLTCKASGFSFSSGYYISWIRQAPGKGLEWIACIYAGGSGTTYYATWAKGRFTVSETSSTTVTLQMSLTAADTATYFCARDYIGTRTYYFDFWGPGTLVTVST |
| 6 | 54B08 | QEQLVESGGGLVQPEGSLTLTCTASGFSFSGNYYMWWVRQAPGKGLEWIACIHIDSGRPWYASWAKGRFTISKTSSTTVTLQMTSLTVADTATYFCARGVSSVYWRTYFNLWGPGTLVTVSS |

TABLE 2-continued

| SEQ ID NO: | Clone | Heavy chain variable domain Protein Sequence |
|---|---|---|
| 7 | 54C02 | QQQLVESGGGLVKPGGTLTLTCTVSGFYFNRGYWICWVRQAPGKGLEWIGCIDTGSG VPYYANWAKGRFTISKTSSTAVTLQMTSLTAADTATYFCARNSDSIYFNLWGPGTLVT VSS |
| 8 | 59A08 | QEQLVESGGGLVKPGGTLTLTCTASGFSFSSGFYISWVRQAPGKGPELISHIYTTSTTT WYASWAKGRFTISKTSSTTVTLQMTSLTAADTATYFCARAGYVDYGYAPYDMDLWGP GTLVTVSS |
| 9 | 59E07 | QSLEESGGGLVQPEGSLTLTCKASGFSFSYNVYMCWVRQAPGKGLEWIGCIYAVSSN TIYYANWAKGRFTISKTSSTTVTLQLPSLTAADTATYFCATRDANAGYSFNLWGPGTLV TVSS |
| 10 | 59F10 | QSLEESGGDLVQPEGSLTLTCKASGFSFSSGYYMCWVRQAPGKGLGLIACIDAGGRG DTVYASWAKGRFTISKTSSTTVTLQLNSLTAADTAIYFCARRGYSSISSNFGAFNPWGP GTLVTVSS |
| 11 | 59G03 | QELKESGGRLVTPGGSLTLTCTASGFSFNSNYYMCWVRQAPGKGLEWIACIYGGTTV NTYYATWAKGRFAISKTSSTTVTLQMTSLTAADTATYFCAREDLTAYSSYVITLWGPGT LVTVSS |
| 12 | 77B06 | QEQLEESGGDLVKPEGSLTLTCTVSGFSFNRGYWICWVRQAPGKGLEWIGCVDTGS GSSYYANWAKGRFTISKTSSTAVTLQMTSLTAADTATYFCARNSDSIYFNLWGPGTLV TVSS |
| 13 | 80D08 | CQSLEESGGALVKPGASLTLTCTASGFSFTSRDYICWVRQAPGKGLEWTGCIAIDGGV IYYATWAKGRFTISKTSSTTVTLQMTSLTAADTATYFCARDDIGSNSYYNDLWGPGTLV TVSS |
| 14 | 80G08 | QEQLEESGGGLVKPGASLTLTCTASGFSFSNNYYISWVRQAPGKGLEWIACIYTGYSW TYYASWAKGRFTISKTSSTTVTLQMTSLTVADTATYFCARADSGYSGFNLWGPGTLVT VSS |
| 15 | 81E11 | CQSLEESGGGLVQPGASLTLTCTASGFSFSSSYWICWVRQAPGKGLEWIACIYTTTNN IGYANWAKGRFTISKTSSTTVTLQMTSLTAADTATYFCAREDYDYYSFHPWGPGTLVT VSS |
| 16 | 82C08 | QQQLEESGGGLVKPGGTLTLTCTASGFTFSSYWISWVRQAPGKGLEWIAYIFTSSITFT AYASWAKGRFTVSKTSSTTVTLQLTSLTAADTATYFCARDLSSTSYYFNLWGPGTLVT VSS |
| 17 | 82F02 | QEQLVESGGGLVQPEGSLTLTCTASGFSFSGNYHMWWVRQAPGKGLEWIACIHTDS GRTWYASWAKGRFTISKTSSTTVTLQMTSLTVADTATYFCARGVSSVYWRTYFNLWG PGTLVTVSS |
| 18 | 99A09 | QEQLEESGGDLVKPEGSLTLTCTVSGFSFSNNYWICWVRQAPGKGLEWIACIYLGSS GYTYFASWARGRFTISKPSSTTVTLQMTSLTAADTATYFCARSYYTYGYAGYIYPTYFN LWGPGTLVTVSS |
| 19 | SD215 | QEQLVESGGGLVKPGGTLTLTCTASGFSFSSGFYISWVRQAPGKGPELISHIYTTSTTT WYASWAKGRFTISKTSSTTVTLQMTSLTAADTATYFCARAGYVDYGYAPYDMDLWGP GTLVTVSS |
| 20 | SD232 | EQLVESGGGLVQPEGSLTLTCTASGFSFSSYYMCWVRQAPGKGLEWIGCIHTDSGRT WYASWAKGRFTISKTSSTTVTLQMTSLTVADTATYFCARGISSVYWRTYFNLWGPGTL VTVSS |
| 21 | SD272 | QQQLEESGGGLVKPGGTLTLTCTVSGFSFNAGYWICWVRQAPGKGLEWIGCIDTGSG VSYYASWAKGRFTISKTSSTAVTLQMTGLTVADTATYFCARNTDSIYFNLWGPGTLVT VSS |
| 22 | SD312 | QSLEESGGDLVQPEGSLTLTCKASGFSFSSGYYMCWVRQAPGKGLGLIACIDAGGRG DTVYASWAKGRFTISKTSSTTVTLQLNSLTAADTAIYFCARRGYSSISSNFGAFNPWGP GTLVTVSS |
| 23 | SD331 | QQQLEESGGGLVKPEGSLTLTCKASGFDFTSYYYMCWVRQAPGKGLELIAYIESSSG RIWYASWAKGRFTISKTSSTTVTLQMTSLTGADTASYFCARDISSSGYHGFKWWGPG TLVTVSS |

TABLE 3

| SEQ ID NO: | Clone | Light chain variable domain Protein Sequence |
|---|---|---|
| 24 | 49E05 | DIVMTQTPVSVSEPVGGIVTIKCQASQSIGSNLAWYQQKPGQPPKLLIYLASTLASGVP SRFKGSGSGTEFTLTISDLECADAATYYCQGYYWSSSRSYGSAFGGGTEVVVV |
| 25 | 49E12 | AYDMTQTPASVSEPVGGAVTIKCQASQSIGSNLAWYQQKPGQPPKLLIYGASTLASGV SSRFKGSGSGTQFTLTISGVECADAATYYCQQGYTYSHADNAFGGGTEVVVV |
| 26 | 50H08 | AYDMTQTPSSVSAAVGGTVTIKCQASQSIGTYLAWYQQKPGQPPKRLIYKASSLPSGV SSRFKGGGSGTEFTLTISGVECADAATYYCQQAYTHTYLDNGFGGGTEVVVV |
| 27 | 52E07 | AYDMTQTPASVEVAVGGTVTIKCQASQSISSYLSWYQQKPGQPPKLLIYKASTLASGV SSRFKGSGSGTEFTLTISGVECADAATYYCQQAYTHTNLDNGFGGGTEVVVV |
| 28 | 52G02 | AQVLTQTPSSVSAAVGGTVTINCQASQSVYKNNYLSWYQQKPGQPPKLLIYEASKLAS GVPSRFSGSGSGTQFTLTISGVQCDDAATYYCAGEFTCISADCFAFGGGTEVVVV |
| 29 | 54B08 | DVVLTQTPSSASEPVGGTVTIKCQASQTIGSNLAWYQQKPGQPPKLLIYGASNLPSGV PSRFSGSASGTEFTLTISGVQCDDAATYYCQSAYWLDSGDNGFGGGTEVVVV |
| 30 | 54C02 | DIVMTQTPASVSEPVGGTVTIKCQASQSIGGYLSWYQQKPGQPPKLLIYKASTLASGVP SRFKGSGSGTDFTLTISDLECADAATYYCQNYAGVSIYGAVFGGGTKVVVV |
| 31 | 59A08 | ALVMTQTPSSVSAAVGGTVTIKCQASQSISGYLAWYQQKPGQPPKLLIYRASTLASGV SSRFKGSGSGTEYTLTISGVECADAATYYCQQGYSMYYIETSFGGGTKVVVV |
| 32 | 59E07 | GYDMTQTPASVSAAVGGTITIKCQASQSISNWLAWYQQKPGQPPKLLIYSASTLASGV PSRFKGSGSGTQFTLTISDMQCDDAATYYCEGGYSSGDRNVFGGGTKVVVV |
| 33 | 59F10 | AYDMTQTPASVEVAVGGTVTIKCQASQSISSYLAWYQQKPGQPPKQLIYGASTLASGV SSRFKGSGSGTQFTLTISGVECADSATYYCQQGYTSIYVDNAFGGGTKVVVV |
| 34 | 59G03 | AYDMTQTPASVSEPVGGTVTIKCQASETIYRNLAWYQQKPGQPPKLLIYAASTLASGV PSRFKGSGSGTQFTLTISDLECADAATYYCQQAYTRVNIDNAFGGGTKVVVV |
| 35 | 77B06 | DIVMTQTPVSVSEPVGGTVTIKCQASQSISSYLSWYQQKPGQPPKLLIYRASTLASGVP SRFKGSGSGTEYTLTISDLECADAAAYYCQNYAGVSLYGAVFGGGTEVVVV |
| 36 | 80D08 | AYDMTQTPASVSAAVGGTVTINCQASQNIYSNLAWYQQKPGQRPKLLIYRASTLASGV PSRFRGSGSGTQFTLTISDLECADAATYYCQQGYTYIHADNAFGGGTEVVVV |
| 37 | 80G08 | DVVMTQTPASVSEPVGGTVTIKCQASQSIDSRLAWYQQKPGQPPKLLIYGASTLASGV PSRFKGSGSGTEYTLTISGVQCADAATYYCQCSVTISTGVGGAFGGGTKVVVV |
| 38 | 81E11 | AYDMTQTPASVSAAVGGTVTIKCQASQSIGTYLAWYQQKPGQPPKRLLYKASSLASG VSSRFKGGGSGTEFSLTISGVECADAATYYCQQAYTHTYLDNGFGGGTKVVVV |
| 39 | 82C08 | AYDVTQTPASVEVAVGGTVTIKCQASETVSYRLAWYQQKPGQPPKLLIYDASTLASGV PSRFSGSGSETEFTLTISGVECADAAIYYCQQGYTRNNIDNTFGGGTKVVVV |
| 40 | 82F02 | DVVLTQTPSSASEPVGGTVTIKCQASQTIGSNLAWYHQKPGQPPKLLIYGASNLASGV PSRFSGSASGTQFTLTISGVQCDDAATYYCQSAYWLDSGDNGFGGGTKVVVV |
| 41 | 99A09 | NIVMTQTPSPVSAAVGGTVTIKCQASQSISSYLAWYQQKPGQPPKLLIYKASTLASGVS SRLKGSGSGTEFTLTISDLECADAATYYCQTYDYSSSNSYGSNAFGGGTKVVVV |
| 42 | SD215 | ALVMTQTPSSVSAAVGGTVTIKCQASQSISGYLAWYQQKPGQPPKLLIYRASTLASGV SSRFKGSGSGTEYTLTISGVECADAATYYCQQGYSMYYIETSFGGGTEVVVV |
| 43 | SD232 | DVVMTQTPSSVSEPVGGTVTIRCQASQSIGSNLAWYQQKPGQPPKLLIYGASNLASGV PSRFSGSASGTQFTLTISGVQCDDAATYYCQSAYWLDSGDNGFGGGTEVVVV |
| 44 | SD272 | DIVMTQTPASVEAAVGGTVTIKCQASQTIYSYLSWYQQKPGQPPKLLIYKASTLASGVS SRFKGSGSGTEFTLTISDLECADAAAYYCQTYAGVSIYGAAFGGGTKVVVV |
| 45 | SD312 | AYDMTQTPASVEVAVGGTVTIKCQASQSISSYLAWYQQKPGQPPKQLIYGASTLASGV SSRFKGSGSGTQFTLTISGVECADSATYYCQQGYTSIYVDNAFGGGTKVVVV |
| 46 | SD331 | AIKMTQTPASVEAAVGGTVTIKCQASQSISNYLAWYQQKPGQPPKLLIYRASTLESGVP SRFKGSGSGTDFTLTISDLECADAATYYCQQVYSITNIDNAFGGGTEVVVV |

TABLE 4

| SEQ ID NO: | Clone 49E05 | Protein Sequence |
|---|---|---|
| 47 | CDR1 VH | GIDFSSYYY |
| 48 | CDR2 VH | IFNGDAST |
| 49 | CDR3 VH | RSDYSVAFAAFLYPTYFTL |
| 50 | CDR1 VL | QSIGSN |
| 51 | CDR2 VL | LAS |
| 52 | CDR3 VL | QGYYWSSSRSYGSA |

TABLE 5

| SEQ ID NO: | Clone 49E12 | Protein Sequence |
|---|---|---|
| 53 | CDR1 VH | GFDLSSFVY |
| 54 | CDR2 VH | IAINGGV |
| 55 | CDR3 VH | ARDDTSSNSYYNDL |
| 56 | CDR1 VL | QSIGSN |
| 57 | CDR2 VL | GAS |
| 58 | CDR3 VL | QQGYTYSHADNA |

TABLE 6

| SEQ ID NO: | Clone 50H08 | Protein Sequence |
|---|---|---|
| 59 | CDR1 VH | GFSFSSSYW |
| 60 | CDR2 VH | IYTTTSN |
| 61 | CDR3 VH | AREDYDYYSFHP |
| 62 | CDR1 VL | QSIGTY |
| 63 | CDR2 VL | KAS |
| 64 | CDR3 VL | QQAYTHTYLDNG |

TABLE 7

| SEQ ID NO: | Clone 52E07 | Protein Sequence |
|---|---|---|
| 65 | CDR1 VH | GFSFSSSYW |
| 66 | CDR2 VH | VYTTTGN |
| 67 | CDR3 VH | AREGSDIYAFHP |
| 68 | CDR1 VL | QSISSY |
| 69 | CDR2 VL | KAS |
| 70 | CDR3 VL | QQAYTHTNLDNG |

TABLE 8

| SEQ ID NO: | Clone 52G02 | Protein Sequence |
|---|---|---|
| 71 | CDR1 VH | GFSFSSGYY |
| 72 | CDR2 VH | IYAGGSGTT |
| 73 | CDR3 VH | ARDYIGTRTYYFDF |
| 74 | CDR1 VL | QSVYKNNY |
| 75 | CDR2 VL | EAS |
| 76 | CDR3 VL | AGEFTCISADCFA |

TABLE 9

| SEQ ID NO: | Clone 54B08 | Protein Sequence |
|---|---|---|
| 77 | CDR1 VH | GFSFSGNYY |
| 78 | CDR2 VH | IHIDSGRP |
| 79 | CDR3 VH | RGVSSVYWRTYFNL |
| 80 | CDR1 VL | QTIGSN |
| 81 | CDR2 VL | GAS |
| 82 | CDR3 VL | QSAYWLDSGDNG |

TABLE 10

| SEQ ID NO: | Clone 54C02 | Protein Sequence |
|---|---|---|
| 83 | CDR1 VH | GFYFNRGYW |
| 84 | CDR2 VH | IDTGSGV |
| 85 | CDR3 VH | ARNSDSIYFNL |
| 86 | CDR1 VL | QSIGGY |
| 87 | CDR2 VL | KAS |
| 88 | CDR3 VL | QNYAGVSIYGAV |

TABLE 11

| SEQ ID NO: | Clone 59A08 | Protein Sequence |
|---|---|---|
| 89 | CDR1 VH | GFSFSSGFY |
| 90 | CDR2 VH | IYTTSTTT |
| 91 | CDR3 VH | RAGYVDYGYAPYDMDL |
| 92 | CDR1 VL | QSISGY |
| 93 | CDR2 VL | RAS |
| 94 | CDR3 VL | QQGYSMYYIETS |

TABLE 12

| SEQ ID NO: | Clone 59E07 | Protein Sequence |
|---|---|---|
| 95 | CDR1 VH | GFSFSYNVY |
| 96 | CDR2 VH | IYAVSSNTI |

TABLE 12-continued

| SEQ ID NO: | Clone 59E07 | Protein Sequence |
|---|---|---|
| 97 | CDR3 VH | ATRDANAGYSFNL |
| 98 | CDR1 VL | QSISNW |
| 99 | CDR2 VL | SAS |
| 100 | CDR3 VL | EGGYSSGDRNV |

TABLE 13

| SEQ ID NO: | Clone 59F10 | Protein Sequence |
|---|---|---|
| 101 | CDR1 VH | GFSFSSGYY |
| 102 | CDR2 VH | IDAGGRGDT |
| 103 | CDR3 VH | ARRGYSSISSNFGAFNP |
| 104 | CDR1 VL | QSISSY |
| 105 | CDR2 VL | GAS |
| 106 | CDR3 VL | QQGYTSIYVDNA |

TABLE 14

| SEQ ID NO: | Clone 59G03 | Protein Sequence |
|---|---|---|
| 107 | CDR1 VH | GFSFNSNYY |
| 108 | CDR2 VH | IYGGTTVNT |
| 109 | CDR3 VH | AREDLTAYSSYVITL |
| 110 | CDR1 VL | ETIYRN |
| 111 | CDR2 VL | AAS |
| 112 | CDR3 VL | QQAYTRVNIDNA |

TABLE 15

| SEQ ID NO: | Clone 77B06 | Protein Sequence |
|---|---|---|
| 113 | CDR1 VH | GFSFNRGYW |
| 114 | CDR2 VH | VDTGSGS |
| 115 | CDR3 VH | ARNSDSIYFNL |
| 198 | CDR3 VH | ARNSDSIYFNI |
| 116 | CDR1 VL | QSISSY |
| 117 | CDR2 VL | RAS |
| 118 | CDR3 VL | QNYAGVSLYGAV |

TABLE 16

| SEQ ID NO: | Clone 80D08 | Protein Sequence |
|---|---|---|
| 119 | CDR1 VH | GFSFTSRDY |
| 120 | CDR2 VH | IAIDGGV |
| 121 | CDR3 VH | ARDDIGSNSYYNDL |
| 122 | CDR1 VL | QNIYSN |

TABLE 16-continued

| SEQ ID NO: | Clone 80D08 | Protein Sequence |
|---|---|---|
| 123 | CDR2 VL | RAS |
| 124 | CDR3 VL | QQGYTYIHADNA |

TABLE 17

| SEQ ID NO: | Clone 80G08 | Protein Sequence |
|---|---|---|
| 125 | CDR1 VH | GFSFSNNYY |
| 126 | CDR2 VH | IYTGYSW |
| 127 | CDR3 VH | ARADSGYSGFNL |
| 128 | CDR1 VL | QSIDSR |
| 129 | CDR2 VL | GAS |
| 130 | CDR3 VL | QCSVTISTGVGGA |

TABLE 18

| SEQ ID NO: | Clone 81E11 | Protein Sequence |
|---|---|---|
| 131 | CDR1 VH | GFSFSSSYW |
| 132 | CDR2 VH | IYTTTNN |
| 133 | CDR3 VH | AREDYDYYSFHP |
| 134 | CDR1 VL | QSIGTY |
| 135 | CDR2 VL | KAS |
| 136 | CDR3 VL | QQAYTHTYLDNG |

TABLE 19

| SEQ ID NO: | Clone 82C08 | Protein Sequence |
|---|---|---|
| 137 | CDR1 VH | GFTFSSYW |
| 138 | CDR2 VH | IFTSSITF |
| 139 | CDR3 VH | ARDLSSTSYYFNL |
| 140 | CDR1 VL | ETVSYR |
| 141 | CDR2 VL | DAS |
| 142 | CDR3 VL | QQGYTRNNIDNT |

TABLE 20

| SEQ ID NO: | Clone 82F02 | Protein Sequence |
|---|---|---|
| 143 | CDR1 VH | GFSFSGNYH |
| 144 | CDR2 VH | IHTDSGRT |
| 145 | CDR3 VH | RGVSSVYWRTYFNL |
| 146 | CDR1 VL | QTIGSN |
| 147 | CDR2 VL | GAS |
| 148 | CDR3 VL | QSAYWLDSGDNG |

TABLE 21

| SEQ ID NO: | Clone 99A09 | Protein Sequence |
|---|---|---|
| 149 | CDR1 VH | GFSFSNNYW |
| 150 | CDR2 VH | IYLGSSGYT |
| 151 | CDR3 VH | ARSYYTGYAGYIYPTYFNL |
| 152 | CDR1 VL | QSISSY |
| 153 | CDR2 VL | KAS |
| 154 | CDR3 VL | QTYDYSSSNSYGSNA |

TABLE 22

| SEQ ID NO: | Clone SD215 | Protein Sequence |
|---|---|---|
| 155 | CDR1 VH | GFSFSSGFY |
| 156 | CDR2 VH | IYTTSTTT |
| 157 | CDR3 VH | RAGYVDYGYAPYDMDL |
| 158 | CDR1 VL | QSISGY |
| 159 | CDR2 VL | RAS |
| 160 | CDR3 VL | QQGYSMYYIETS |

TABLE 23

| SEQ ID NO: | Clone SD232 | Protein Sequence |
|---|---|---|
| 161 | CDR1 VH | GFSFSSYY |
| 162 | CDR2 VH | IHTDSGR |
| 163 | CDR3 VH | ARGISSVYWRTYFNL |
| 164 | CDR1 VL | QSIGSN |
| 165 | CDR2 VL | GAS |
| 166 | CDR3 VL | QSAYWLDSGDNG |

TABLE 24

| SEQ ID NO: | Clone SD272 | Protein Sequence |
|---|---|---|
| 167 | CDR1 VH | GFSFNAGYW |
| 168 | CDR2 VH | IDTGSGVS |
| 169 | CDR3 VH | RNTDSIYFNL |
| 170 | CDR1 VL | QTIYSY |
| 171 | CDR2 VL | KAS |
| 172 | CDR3 VL | QTYAGVSIYGAA |

TABLE 25

| SEQ ID NO: | Clone SD312 | Protein Sequence |
|---|---|---|
| 173 | CDR1 VH | GFSFSSGYY |
| 174 | CDR2 VH | IDAGGRGDT |
| 175 | CDR3 VH | ARRGYSSISSNFGAFNP |
| 176 | CDR1 VL | QSISSY |
| 177 | CDR2 VL | GAS |
| 178 | CDR3 VL | QQGYTSIYVDNA |

TABLE 26

| SEQ ID NO: | Clone SD331 | Protein Sequence |
|---|---|---|
| 179 | CDR1 VH | GFDFTSYYY |
| 180 | CDR2 VH | IESSSGRI |
| 181 | CDR3 VH | RDISSSGYHGFKW |
| 182 | CDR1 VL | QSISNY |
| 183 | CDR2 VL | RAS |
| 184 | CDR3 VL | QQVYSITNIDNA |

TABLE 27

Amino Acid Sequences of the Humanized Variants - Heavy Chain

| SEQ ID NO: | Name | Sequence |
|---|---|---|
| 186 | HC0 | MGWTLVFLFLLSVTAGVHSQQQLVESGGGLVKPGGTLTLTCTVSGFYFNRGYWICWVR QAPGKGLEWIGCIDTGSGVPYYANWAKGRFTISKTSSTAVTLQMTSLTAADTATYFCAR NSDSIYFNLWGPGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK |
| 187 | HC1 | MGWTLVFLFLLSVTAGVHSEVQLVESGGGLVKPGGSLRLSCTASGFYFNRGYWICWLR QAPGKGLEWVACIDTGSGVPYYANWAKGRFTVSRDNAKNSLFLQMNSLRAEDTAVYYC ARNSDSIYFNLWGPGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKSLSLSPGK |

TABLE 27-continued

Amino Acid Sequences of the Humanized Variants - Heavy Chain

| SEQ ID NO: | Name | Sequence |
|---|---|---|
| 188 | HC2 | MGWTLVFLFLLSVTAGVHSQVQLVESGGGVVQPGRSLRLPCAASGFYFNRGYWICWV<br>RQAPGKGLEWVACIDTGSGVPYYANWAKGRFTISRDTSKNTLYLQMDSLRAEDTAVYY<br>CARNSDSIYFNLWGRGTLVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQKSLSLSPGK |
| 189 | HC3 | MGWTLVFLFLLSVTAGVHSEVQLVESGGDLAQPGGSLRLSCAVSGFYFNRGYWICWVR<br>QAPGKGLEWVSCIDTGSGVPYYANWAKGRFTISRDNSKNTVYLQMTSLRAEDTALYFC<br>ARNSDSIYFNLWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAP<br>IEKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 190 | HC4 | MGWTLVFLFLLSVTAGVHSQVQLVESGGGLVKPGGSLRLSCAASGFYFNRGYWICWIR<br>QAPGKGLEWVSCIDTGSGVPYYANWAKGRFTISRDNAKNSLYLQMNSLRTEDTAVYFC<br>ARNSDSIYFNLWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAP<br>IEKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 191 | HC5 | MGWTLVFLFLLSVTAGVHSEVQLVESGGGLVKPGGSLRLSCAVSGFYFNRGYWICWVR<br>QAPGKGLEWIGCIDTGSGVPYYANWAKGRFTISRHTSKTTLTLQMNSLRAEDTASYFCA<br>RNSDSIYFNLWGPGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 199 | HC4M1 | MGWTLVFLFLLSVTAGVHSQVQLVESGGGLVKPGGSLRLSCAASGFYFNRGYWICWIR<br>QAPGKGLEWVSCIDTGSGVPYYANWAKGRFTISRDNAKNSLYLQMNSLRTEDTAVYFC<br>ARNSDSIYFNIWGQGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDK<br>VEPKSCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 200 | HC4M2 | MGWTLVFLFLLSVTAGVHSQVQLVESGGGLVKPGGSLRLSCAASGFYFNRGYWISWIR<br>QAPGKGLEWVSSIDTGSGVPYYANWAKGRFTISRDNAKNSLYLQMNSLRTEDTAVYFC<br>ARNSDSIYFNLWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAP<br>IEKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 201 | HC4M3 | MGWTLVFLFLLSVTAGVHSQVQLVESGGGLVKPGGSLRLSCAASGFYFNRGYWISWIR<br>QAPGKGLEWVSSIDTGSGVPYYANWAKGRFTISRDNAKNSLYLQMNSLRTEDTAVYFC<br>ARNSDSIYFNIWGQGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 202 | HC5M1 | MGWTLVFLFLLSVTAGVHSEVQLVESGGGLVKPGGSLRLSCAVSGFYFNRGYWICWVR<br>QAPGKGLEWIGCIDTGSGVPYYANWAKGRFTISRHTSKTTLTLQMNSLRAEDTASYFCA<br>RNSDSIYFNIWGQGTLVTVSSASTKGPSVFPLAPSSKSTSGGTAALGCLVKDYFPEPVT<br>SWNSGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK |

TABLE 27-continued

Amino Acid Sequences of the Humanized Variants - Heavy Chain

| SEQ ID NO: | Name | Sequence |
|---|---|---|
| 203 | HC5M2 | MGWTLVFLFLLSVTAGVHSEVQLVESGGGLVKPGGSLRLSCAVSGFYFNRGYWISWVR<br>QAPGKGLEWIGSIDTGSGVPYYANWAKGRFTISRHTSKTTLTLQMNSLRAEDTASYFCA<br>RNSDSIYFNLWGPGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 204 | HC5M3 | MGWTLVFLFLLSVTAGVHSEVQLVESGGGLVKPGGSLRLSCAVSGFYFNRGYWISWVR<br>QAPGKGLEWIGSIDTGSGVPYYANWAKGRFTISRHTSKTTLTLQMNSLRAEDTASYFCA<br>RNSDSIYFNIWGPGTLVTVSSASTKGPSVFPLAPSSKSTSGGTAALGCLVKDYFPEPVTV<br>SWNSGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK |
| 249 | 11E12VH_Hu1 | QVQLVQSGAEVKKPGASVKVSCKASGYTFTSYVINWVRQATGQGLEWIGEIHPRGGNT<br>YYSEKFRGRATMTRDTSISTAYMELSSLRSEDTAVYYCARIRRGNAMDYWGQGTTLTVS<br>SASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 250 | 11E12VH_Hu2 | QVQLVQSGAEVKKPGASVKVSCKASGYTFTSYVINWVRQATGQGLEWIGEIHPRGGNT<br>YYSEKFRGRATLTRDTSISTAYMELSSLRSEDTAVYYCARIRRGNAMDYWGQGTTLTVS<br>SASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 251 | 11E12VH_Hu3 | QVQLVQSGAEVKKPGASVKVSCKASGYTFTSYVINWVRQATGQGLEWIGEIHPRGGNT<br>YYSEKFRGRATLTRDTSISTAYMELSSLRSEDTAVYYCARLRRGNAMDYWGQGTTLTVS<br>SASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |

TABLE 28

Amino Acid Sequences of the Humanized Variants - Light Chain

| SEQ ID NO: | Name | Sequence |
|---|---|---|
| 192 | LC0 | MVSSAQFLGLLLLCFQGTRCDIVMTQTPASVSEPVGGTVTIKCQASQSIGGYLSWYQQK<br>PGQPPKLLIYKASTLASGVPSRFKGSGSGTDFTLTISDLECADAATYYCQNYAGVSIYGA<br>VFGGGTKVVVVRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTKSFNRGEC |
| 193 | LC1 | MVSSAQFLGLLLLCFQGTRCDIVMTQSPSSLSASVGDRVTITCQASQSIGGYLSWYQQK<br>PGKAPKLLIYKASTLASGVPSRFSGSGSGTDFTLTISSLQPEDFATYYCQNYAGVSIYGAV<br>FGGGTKVVIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKSFNRGEC |
| 194 | LC2 | MVSSAQFLGLLLLCFQGTRCDIVLTQSPSSLSASVGDRITITCQASQSIGGYLSWYQQKP<br>GTPPKLLIYKASTLASGVPSRFSGSGSGTDFTLTISRLQPEDVATYYCQNYAGVSIYGAVF<br>GGGTKLEIKRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFNRGEC |
| 195 | LC3 | MVSSAQFLGLLLLCFQGTRCDIQMTQSPSSLSASVGDRITITCQASQSIGGYLSWYQQKP<br>GRVPKLLIYKASTLASGVPSRFSGSGSGTEFTLTISSLQAEDVATYYCQNYAGVSIYGAVF<br>GGGTKVEIKRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFNRGEC |

TABLE 28-continued

Amino Acid Sequences of the Humanized Variants - Light Chain

| SEQ ID NO: | Name | Sequence |
|---|---|---|
| 196 | LC4 | MVSSAQFLGLLLLCFQGTRCDIQMTQSPSSLSASVGDRVTISCQASQSIGGYLSWYQQK<br>PGQAPKLLIYKASTLASGVPSRFSGSGSGTDFTLTISSLQPEDVATYYCQNYAGVSIYGA<br>VFGQGTKVEIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTKSFNRGEC |
| 197 | LC5 | MVSSAQFLGLLLLCFQGTRCDIQMTQSPSSVSASVGDRVTITCQASQSIGGYLSWYQQK<br>PGQPPKLLIYKASTLASGVPSRFKGSGSGTDFTLTISSLDSEDAATYYCQNYAGVSIYGA<br>VFGGGTKVVVKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTKSFNRGEC |
| 205 | LC1M1 | MVSSAQFLGLLLLCFQGTRCDIVMTQSPSSLSASVGDRVTITCQASQSIGGYISWYQQKP<br>GKAPKLLIYKASTLASGVPSRFSGSGSGTDFTLTISSLQPEDFATYYCQNYAGVSIYGAVF<br>GGGTKVVVIKRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFNRGEC |
| 206 | LC5M1 | MVSSAQFLGLLLLCFQGTRCDIQMTQSPSSVSASVGDRVTITCQASQSIGGYISWYQQK<br>PGQPPKLLIYKASTLASGVPSRFKGSGSGTDFTLTISSLDSEDAATYYCQNYAGVSIYGA<br>VFGGGTKVVVKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTKSFNRGEC |
| 252 | 11E12_VL_Hu1 | DIVMTQSPSSLAVSLGERATINCKSSQSLLNSGNQRNYLTWYQQKPGQPPKLLIYWAST<br>RESGVPDRFSGSGSGTDFTLTISSLQAEDVAVYYCQNSYNYPYTFGQGTKLEIKRTVAA<br>PSVFIFPPSDEQLKSGTASVVCLLNNFYPREAKVQWKVDNALQSGNSQESVTEQDSKDS<br>TYSLSSTLTLSKADYEKHKVYACEVTHQGLSSPVTKSFNRGEC |
| 253 | 11E12_VL_Hu2 | DIVMTQSPSSLPVSLGERATINCKSSQSLLNSGNQRNYLTWYQQKPGQPPKLLIYWAST<br>RESGVPDRFSGSGSGTDFTLTISSLQAEDVAVYYCQNSYNYPYTFGQGTKLEIKRTVAA<br>PSVFIFPPSDEQLKSGTASVVCLLNNFYPREAKVQWKVDNALQSGNSQESVTEQDSKDS<br>TYSLSSTLTLSKADYEKHKVYACEVTHQGLSSPVTKSFNRGEC |

TABLE 29

CDRs of Antibodies cloned from Hybridomas - Clone 79C4

| SEQ ID NO: | Clone 79C4 | Protein Sequence |
|---|---|---|
| 207 | CDR1 VH | GFTFSNYWMN |
| 208 | CDR2 VH | EIRLKSKNYATHYAESVKG |
| 209 | CDR3 VH | GHYGTNYGDY |
| 210 | CDR1 VL | RASQEISGYLS |
| 211 | CDR2 VL | AASTLDS |
| 212 | CDR3 VL | LQYDSSPWT |

TABLE 30

CDRs of Antibodies cloned from Hybridomas - Clone 11E12

| SEQ ID NO: | Clone 11E12 | Protein Sequence |
|---|---|---|
| 213 | CDR1 VH | GYTFTSYVIN |
| 214 | CDR2 VH | EIHPRGGNTYYSEKFRG |
| 215 | CDR3 VH | LRRGNAMDY |
| 247 | CDR3 VH | IRRGNAMDY |
| 216 | CDR1 VL | KSSQSLLNSGNQRNYLT |
| 217 | CDR2 VL | WASTRES |
| 218 | CDR3 VL | QNSYNYPYT |

TABLE 31

CDRs of Antibodies cloned from Hybridomas - Clone 83G3

| SEQ ID NO: | Clone 83G3 | Protein Sequence |
|---|---|---|
| 219 | CDR1 VH | GFTFTSYWIH |
| 220 | CDR2 VH | YIDPSNTYTKFNQKFKD |
| 221 | CDR3 VH | GRGFAY |
| 222 | CDR1 VL | DKSSQSLFNSGNQKHYLT |
| 223 | CDR2 VL | RASTRES |
| 224 | CDR3 VL | QNDYSFPLT |

TABLE 32

CDRs of Antibodies cloned from Hybridomas - Clone 30B5

| SEQ ID NO: | Clone 30B5 | Protein Sequence |
|---|---|---|
| 225 | CDR1 VH | GFTFSNYWMN |
| 226 | CDR2 VH | EIRLKSKNYATHYAESVKG |
| 227 | CDR3 VH | GHYGTNYGDY |
| 228 | CDR1 VL | KSSQSLFNSGNQKHYLT |
| 229 | CDR2 VL | RASTRES |
| 230 | CDR3 VL | QNDYSFPLT |

TABLE 33

CDRs of Antibodies cloned from Hybridomas - Clone 85H12

| SEQ ID NO: | Clone 85H12 | Protein Sequence |
|---|---|---|
| 231 | CDR1 VH | GFTFSNYWMN |
| 232 | CDR2 VH | EIRLKSKNYATHYAESVKG |
| 233 | CDR3 VH | GHYGTNYGDY |
| 234 | CDR1 VL | KSSQSLFNSGNQKHYLT |
| 235 | CDR2 VL | RASTRES |
| 236 | CDR3 VL | QNDYSFPLT |

TABLE 34

Heavy chain variable domain Protein Sequence

| SEQ ID NO: | Clone | Heavy chain variable domain Protein Sequence |
|---|---|---|
| 237 | 79C4 | EVKLEESGGGLVQPGGSMKLSCVASGFTFSNYWMNWVRQSPEKGLEWVAEIRLKSKNYATHYAESVKGRFTISRDDSIGSVYLQMNNLRAEDTGIYYCARGHYGTNYGDYWGQGTSVTVSS |
| 238 | 11E12 | QVQLQQSGAELARPGASVKLSCKASGYTFTSYVINWVKQKTGQGLEWIGEIHPRGGNTYYSEKFRGRATLTADKSSSTAYMEFRSLTSEDSAVYFCAILRRGNAMDYWDQGTAVTVSS |
| 239 | 83G3 | QVQLQQSGAELAKPGASVKLSCKASGFTFTSYWIHWVKQRPGQGLEWIGYIDPSNTYTKFNQKFKDKATLTADKSSSTAYMQLNSLTFEDSAVYYCATGRGFAYWGQGTLVTVSS |
| 240 | 30B5 | EVKLEESGGGLVQPGGSMKLSCVASGFTFSNYWMNWVRQSPEKGLEWVAEIRLKSKNYATHYAESVKGRFTISRDDSIGSVYLQMNNLRAEDTGIYYCARGHYGTNYGDYWGQGTSVTVSS |
| 241 | 85H12 | EVKLEESGGGLVQPGGSMKLSCVASGFTFSNYWMNWVRQSPEKGLEWVAEIRLKSKNYATHYAESVKGRFTISRDDSIGSVYLQMNNLRAEDTGIYYCARGHYGTNYGDYWGQGTSVTVSS |
| 248 | 11E12 mutein | QVQLQQSGAELARPGASVKLSCKASGYTFTSYVINWVKQKTGQGLEWIGEIHPRGGNTYYSEKFRGRATLTADKSSSTAYMEFRSLTSEDSAVYFCARIRRGNAMDYWDQGTAVTVSS |

TABLE 35

Light chain variable domain Protein Sequence

| SEQ ID NO: | Clone | Light chain variable domain Protein Sequence |
|---|---|---|
| 242 | 79C4 | DIQTTQSPSSLSASLGERVTLTCRASQEISGYLSWLQQKPDGTIKRLIYAASTLDSGVPKRFSGSRSGDYSLTINSLESEDFVDYYCLQYDSSPWTFGGGTKLEIK |
| 243 | 11E12 | DIVMTQSPSSLPVTAGEMVTMSCKSSQSLLNSGNQRNYLTWYQQKPGQPPKLLIYWASTRESGVPDRFTGSGSGTDFTLTISSVQAEDLAVYYCQNSYNYPYTFGGGTKLERK |
| 244 | 83G3 | DIVMTQSPSSLTVTAGEKVTVSCKSSQSLFNSGNQKHYLTWYQQKPGQPPKWYRASTRESGVPDRFTGSGSGTDFTLTIRNVQAEDLAVYYCQNDYSFPLTFGAGTKLELK |
| 245 | 30B5 | DIVMTQSPSSLTVTAGEKVTVSCKSSQSLFNSGNQKHYLTWYQQKPGQPPKLLIYRASTRESGVPDRFTGSGSGTDFTLTIRNVQAEDLAVYYCQNDYSFPLTFGAGTKLELK |
| 246 | 85H12 | DIVMTQSPSSLTVTAGEKVTVSCKSSQSLFNSGNQKHYLTWYQQKPGQPPKLLIYRASTRESGVPDRFTGSGSGTDFTLTIRNVQAEDLAVYYCQNDYSFPLTFGAGTKLELK |

TABLE 36

11E12 Humanized Sequences

| SEQ ID NO: | Name | Humanized heavy chain and light chain variable domain Protein Sequences |
|---|---|---|
| 254 | hu11E12VHv1 | QVQLVQSGAEVKKPGASVKVSCKASGYTFTSYVINWVRQATGQGLEWIGEIHPRGGNTYYSEKFRGRVTLTADTSISTAYMELSSLRSEDTAVYYCAILRRGNAMDYWDQGTTVTVSS |

TABLE 36-continued

11E12 Humanized Sequences

| SEQ ID NO: | Name | Humanized heavy chain and light chain variable domain Protein Sequences |
|---|---|---|
| 255 | hu11E12VHv2 | QVQLVQSGAEVKKPGASVKVSCKASGYTFTSYVINWVKQKTGQGLEWIGEIHPRGGNTYYSEKFRGRATLTADKSISTAYMELSSLRSEDTAVYFCAILRRGNAMDYWDQGTTVTVSS |
| 256 | hu11E12VHv3 | QVQLVQSGAEVKKPGASVKLSCKASGYTFTSYVINWVKQKTGQGLEWIGEIHPRGGNTYYSEKFRGRATLTADKSISTAYMELSSLRSEDTAVYFCAILRRGNAMDYWDQGTTVTVSS |
| 257 | hu11E12VHv1B | QVQLVQSGAEVKKPGASVKVSCKASGYTFTSYVINWVRQATGQGLEWIGEIHPRGGNTYYSEKFRGRVTLTADTSISTAYMELSSLRSEDTAVYYCARLRRGNAMDYWDQGTTVTVSS |
| 258 | hu11E12VHv2B | QVQLVQSGAEVKKPGASVKVSCKASGYTFTSYVINWVKQKTGQGLEWIGEIHPRGGNTYYSEKFRGRATLTADKSISTAYMELSSLRSEDTAVYFCARLRRGNAMDYWDQGTTVTVSS |
| 259 | hu11E12VHv3B | QVQLVQSGAEVKKPGASVKLSCKASGYTFTSYVINWVKQKTGQGLEWIGEIHPRGGNTYYSEKFRGRATLTADKSISTAYMELSSLRSEDTAVYFCARLRRGNAMDYWDQGTTVTVSS |
| 260 | hu11E12VLv1 | DIVMTQSPSSLAVSLGEMATINCKSSQSLLNSGNQRNYLTWYQQKPGQPPKLLIYWASTRESGVPDRFSGSGSGTDFTLTISSLQAEDVAVYYCQNSYNYPYTFGQGTKLERK |
| 261 | hu11E12VLv2 | DIVMTQSPSSLAVSAGEMVTMNCKSSQSLLNSGNQRNYLTWYQQKPGQPPKLLIYWASTRESGVPDRFSGSGSGTDFTLTISSVQAEDLAVYYCQNSYNYPYTFGQGTKLEIK |
| 262 | hu11E12VLv3 | DIVMTQSPSSLAVSAGEMVTMNCKSSQSLLNSGNQRNYLTWYQQKPGQPPKLLIYWASTRESGVPDRFSGSGSGTDFTLTISSVQAEDLAVYYCQNSYNYPYTFGQGTKLERK |

TABLE 37

83G3 Humanized Sequences

| SEQ ID NO: | Clone | Humanized heavy chain and light chain variable domain Protein Sequences |
|---|---|---|
| 263 | hu83G3VHv1 | QVQLVQSGAEVKKPGASVKVSCKASGFTFTSYWIHWVRQRPGQGLEWIGYIDPSNTYTKFNQKFKDRVTLTADTSTSTAYMELSSLRSEDTAVYYCATGRGFAYWGQGTLVTVSS |
| 264 | hu83G3VHv2 | QVQLVQSGAEVKKPGASVKLSCKASGFTFTSYWIHWVRQRPGQGLEWIGYIDPSNTYTKFNQKFKDRATLTADTSTSTAYMELSSLRSEDTAVYYCATGRGFAYWGQGTLVTVSS |
| 265 | hu83G3VHv3 | QVQLQQSGAEVKKPGASVKLSCKASGFTFTSYWIHWVRQRPGQGLEWIGYIDPSNTYTKFNQKFKDRATLTADTSTSTAYMELSSLRSEDTAVYYCATGRGFAYWGQGTLVTVSS |
| 266 | hu83G3VLv1 | DIVMTQSPSSLAVSLGERATINCKSSQSLFNSGNQKHYLTWYQQKPGQPPKLLIYRASTRESGVPDRFSGSGSGTDFTLTISSLQAEDVAVYYCQNDYSFPLTFGQGTKLEIK |
| 267 | hu83G3VLv2 | DIVMTQSPSSLAVSLGERATVNCKSSQSLFNSGNQKHYLTWYQQKPGQPPKLLIYRASTRESGVPDRFSGSGSGTDFTLTISSLQAEDVAVYYCQNDYSFPLTFGQGTKLEIK |
| 268 | hu83G3VLv3 | DIVMTQSPSSLAVSLGERATVNCKSSQSLFNSGNQKHYLTWYQQKPGQPPKLLIYRASTRESGVPDRFSGSGSGTDFTLTIRSLQAEDVAVYYCQNDYSFPLTFGQGTKLEIK |
| 269 | hu83G3VLv4 | DIVMTQSPSSLAVSLGERATVNCKSSQSLFNSGNQKHYLTWYQQKPGQPPKLLIYRASTRESGVPDRFTGSGSGTDFTLTISSLQAEDVAVYYCQNDYSFPLTFGQGTKLEIK |

The above non-limiting examples are provided for illustrative purposes only in order to facilitate a more complete understanding of the disclosed subject matter. These examples should not be construed to limit any of the embodiments described in the present specification, including those pertaining to the antibodies, pharmaceutical compositions, or methods and uses for treating cancer, a neurodegenerative or an infectious disease.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A method of treating a CLDN18.2 expressing cancer in a subject, the method comprising administering a therapeutic amount of a humanized antibody to the subject, wherein the humanized antibody comprises a heavy chain variable domain selected from SEQ ID NO: 263, 264 and 265 and a light chain variable domain selected from SEQ ID NO: 266, 267, 268 and 269.

2. The method of claim 1, wherein the CLDN18.2 expressing cancer is gastric, esophagus, pancreatic or liver cancer.

3. The method of claim 1, further comprising administering a chemotherapeutic agent to the subject.

4. The method of claim 3, wherein the chemotherapeutic agent is one or more of a nucleoside analog, a platinum compound, a camptothecin analog and a taxane.

5. The method of claim 3, wherein the chemotherapeutic agent is one or more of gemcitabine, 5-fluorouracil, capecitabine, oxaliplatin, irinotecan and paclitaxel.

6. The method of claim 3, wherein the chemotherapeutic agent is one or more of oxaliplatin and paclitaxel.

7. The method of claim 1, wherein the heavy chain and/or the light chain of the humanized antibody is fused with one or more IL-2 polypeptides, one or more IL-2 analogs, one or more IL-15 polypeptides or one or more IL-15 analogs.

8. A method of treating a CLDN18.2 expressing cancer in a subject, the method comprising administering a therapeutic amount of an antibody which binds to human CLDN18.2 protein, wherein the antibody is selected from:

a. an antibody comprising a heavy chain variable region comprising heavy chain CDR1 containing the amino acid sequence as set forth in SEQ ID NO: 47, heavy chain CDR2 containing the amino acid sequence as set forth in SEQ ID NO: 48, and heavy chain CDR3 containing the amino acid sequence as set forth in SEQ ID NO: 49, and a light chain variable region comprising light chain CDR1 containing the amino acid sequence as set forth in SEQ ID NO: 50, light chain CDR2 containing the amino acid sequence as set forth in SEQ ID NO: 51, and light chain CDR3 containing the amino acid sequence as set forth in SEQ ID NO: 52;

b. an antibody comprising a heavy chain variable region comprising heavy chain CDR1 containing the amino acid sequence as set forth in SEQ ID NO: 53, heavy chain CDR2 containing the amino acid sequence as set forth in SEQ ID NO: 54, and heavy chain CDR3 containing the amino acid sequence as set forth in SEQ ID NO: 55, and a light chain variable region comprising light chain CDR1 containing the amino acid sequence as set forth in SEQ ID NO: 56, light chain CDR2 containing the amino acid sequence as set forth in SEQ ID NO: 57, and light chain CDR3 containing the amino acid sequence as set forth in SEQ ID NO: 58;

c. an antibody comprising a heavy chain variable region comprising heavy chain CDR1 containing the amino acid sequence as set forth in SEQ ID NO: 59, heavy chain CDR2 containing the amino acid sequence as set forth in SEQ ID NO: 60, and heavy chain CDR3 containing the amino acid sequence as set forth in SEQ ID NO: 61, and a light chain variable region comprising light chain CDR1 containing the amino acid sequence as set forth in SEQ ID NO: 62, light chain CDR2 containing the amino acid sequence as set forth in SEQ ID NO: 63, and light chain CDR3 containing the amino acid sequence as set forth in SEQ ID NO: 64;

d. an antibody comprising a heavy chain variable region comprising heavy chain CDR1 containing the amino acid sequence as set forth in SEQ ID NO: 65, heavy chain CDR2 containing the amino acid sequence as set forth in SEQ ID NO: 66, and heavy chain CDR3 containing the amino acid sequence as set forth in SEQ ID NO: 67, and a light chain variable region comprising light chain CDR1 containing the amino acid sequence as set forth in SEQ ID NO: 68, light chain CDR2 containing the amino acid sequence as set forth in SEQ ID NO: 69, and light chain CDR3 containing the amino acid sequence as set forth in SEQ ID NO: 70;

e. an antibody comprising a heavy chain variable region comprising heavy chain CDR1 containing the amino acid sequence as set forth in SEQ ID NO: 71, heavy chain CDR2 containing the amino acid sequence as set forth in SEQ ID NO: 72, and heavy chain CDR3 containing the amino acid sequence as set forth in SEQ ID NO: 73, and a light chain variable region comprising light chain CDR1 containing the amino acid sequence as set forth in SEQ ID NO: 74, light chain CDR2 containing the amino acid sequence as set forth in SEQ ID NO: 75, and light chain CDR3 containing the amino acid sequence as set forth in SEQ ID NO: 76;

f. an antibody comprising a heavy chain variable region comprising heavy chain CDR1 containing the amino acid sequence as set forth in SEQ ID NO: 77, heavy chain CDR2 containing the amino acid sequence as set forth in SEQ ID NO: 78, and heavy chain CDR3 containing the amino acid sequence as set forth in SEQ ID NO: 79, and a light chain variable region comprising light chain CDR1 containing the amino acid sequence as set forth in SEQ ID NO: 80, light chain CDR2 containing the amino acid sequence as set forth in SEQ ID NO: 81, and light chain CDR3 containing the amino acid sequence as set forth in SEQ ID NO: 82;

g. an antibody comprising a heavy chain variable region comprising heavy chain CDR1 containing the amino acid sequence as set forth in SEQ ID NO: 83, heavy chain CDR2 containing the amino acid sequence as set forth in SEQ ID NO: 84, and heavy chain CDR3 containing the amino acid sequence as set forth in SEQ ID NO: 85, and a light chain variable region comprising light chain CDR1 containing the amino acid sequence as set forth in SEQ ID NO: 86, light chain CDR2 containing the amino acid sequence as set forth in SEQ ID NO: 87, and light chain CDR3 containing the amino acid sequence as set forth in SEQ ID NO: 88;

h. an antibody comprising a heavy chain variable region comprising heavy chain CDR1 containing the amino acid sequence as set forth in SEQ ID NO: 89, heavy chain CDR2 containing the amino acid sequence as set forth in SEQ ID NO: 90, and heavy chain CDR3 containing the amino acid sequence as set forth in SEQ ID NO: 91, and a light chain variable region comprising light chain CDR1 containing the amino acid sequence as set forth in SEQ ID NO: 92, light chain CDR2 containing the amino acid sequence as set forth in SEQ ID NO: 93, and light chain CDR3 containing the amino acid sequence as set forth in SEQ ID NO: 94;

i. an antibody comprising a heavy chain variable region comprising heavy chain CDR1 containing the amino acid sequence as set forth in SEQ ID NO: 95, heavy chain CDR2 containing the amino acid sequence as set forth in SEQ ID NO: 96, and heavy chain CDR3 containing the amino acid sequence as set forth in SEQ ID NO: 97, and a light chain variable region comprising light chain CDR1 containing the amino acid sequence as set forth in SEQ ID NO: 98, light chain CDR2 containing the amino acid sequence as set forth in SEQ ID NO: 99, and light chain CDR3 containing the amino acid sequence as set forth in SEQ ID NO: 100;

j. an antibody comprising a heavy chain variable region comprising heavy chain CDR1 containing the amino acid sequence as set forth in SEQ ID NO: 101, heavy chain CDR2 containing the amino acid sequence as set forth in SEQ ID NO: 102, and heavy chain CDR3 containing the amino acid sequence as set forth in SEQ ID NO: 103, and a light chain variable region comprising light chain CDR1 containing the amino acid sequence as set forth in SEQ ID NO: 104, light chain CDR2 containing the amino acid sequence as set forth in SEQ ID NO: 105, and light chain CDR3 containing the amino acid sequence as set forth in SEQ ID NO: 106;

k. an antibody comprising a heavy chain variable region comprising heavy chain CDR1 containing the amino acid sequence as set forth in SEQ ID NO: 107, heavy chain CDR2 containing the amino acid sequence as set forth in SEQ ID NO: 108, and heavy chain CDR3 containing the amino acid sequence as set forth in SEQ ID NO: 109, and a light chain variable region comprising light chain CDR1 containing the amino acid sequence as set forth in SEQ ID NO: 110, light chain CDR2 containing the amino acid sequence as set forth in SEQ ID NO: 111, and light chain CDR3 containing the amino acid sequence as set forth in SEQ ID NO: 112;

l. an antibody comprising a heavy chain variable region comprising heavy chain CDR1 containing the amino acid sequence as set forth in SEQ ID NO: 113, heavy chain CDR2 containing the amino acid sequence as set forth in SEQ ID NO: 114, and heavy chain CDR3 containing the amino acid sequence as set forth in SEQ ID NO: 115 or 198, and a light chain variable region comprising light chain CDR1 containing the amino acid sequence as set forth in SEQ ID NO: 116, light chain CDR2 containing the amino acid sequence as set forth in SEQ ID NO: 117, and light chain CDR3 containing the amino acid sequence as set forth in SEQ ID NO: 118;

m. an antibody comprising a heavy chain variable region comprising heavy chain CDR1 containing the amino acid sequence as set forth in SEQ ID NO: 113, heavy chain CDR2 containing the amino acid sequence as set forth in SEQ ID NO: 114, and heavy chain CDR3 containing the amino acid sequence as set forth in SEQ ID NO: 198, and a light chain variable region comprising light chain CDR1 containing the amino acid sequence as set forth in SEQ ID NO: 116, light chain CDR2 containing the amino acid sequence as set forth in SEQ ID NO: 117, and light chain CDR3 containing the amino acid sequence as set forth in SEQ ID NO: 118;

n. an antibody comprising a heavy chain variable region comprising heavy chain CDR1 containing the amino acid sequence as set forth in SEQ ID NO: 119, heavy chain CDR2 containing the amino acid sequence as set forth in SEQ ID NO: 120, and heavy chain CDR3 containing the amino acid sequence as set forth in SEQ ID NO: 121, and a light chain variable region comprising light chain CDR1 containing the amino acid sequence as set forth in SEQ ID NO: 122, light chain CDR2 containing the amino acid sequence as set forth in SEQ ID NO: 123, and light chain CDR3 containing the amino acid sequence as set forth in SEQ ID NO: 124;

o. an antibody comprising a heavy chain variable region comprising heavy chain CDR1 containing the amino acid sequence as set forth in SEQ ID NO: 125, heavy chain CDR2 containing the amino acid sequence as set forth in SEQ ID NO: 126, and heavy chain CDR3 containing the amino acid sequence as set forth in SEQ ID NO: 127, and a light chain variable region comprising light chain CDR1 containing the amino acid sequence as set forth in SEQ ID NO: 128, light chain CDR2 containing the amino acid sequence as set forth in SEQ ID NO: 129, and light chain CDR3 containing the amino acid sequence as set forth in SEQ ID NO: 130;

p. an antibody comprising a heavy chain variable region comprising heavy chain CDR1 containing the amino acid sequence as set forth in SEQ ID NO: 131, heavy chain CDR2 containing the amino acid sequence as set forth in SEQ ID NO: 132, and heavy chain CDR3 containing the amino acid sequence as set forth in SEQ ID NO: 133, and a light chain variable region comprising light chain CDR1 containing the amino acid sequence as set forth in SEQ ID NO: 134, light chain CDR2 containing the amino acid sequence as set forth in SEQ ID NO: 135, and light chain CDR3 containing the amino acid sequence as set forth in SEQ ID NO: 136;

q. an antibody comprising a heavy chain variable region comprising heavy chain CDR1 containing the amino acid sequence as set forth in SEQ ID NO: 137, heavy chain CDR2 containing the amino acid sequence as set forth in SEQ ID NO: 138, and heavy chain CDR3 containing the amino acid sequence as set forth in SEQ ID NO: 139, and a light chain variable region comprising light chain CDR1 containing the amino acid sequence as set forth in SEQ ID NO: 140, light chain CDR2 containing the amino acid sequence as set forth in SEQ ID NO: 141, and light chain CDR3 containing the amino acid sequence as set forth in SEQ ID NO: 142;

r. an antibody comprising a heavy chain variable region comprising heavy chain CDR1 containing the amino acid sequence as set forth in SEQ ID NO: 143, heavy chain CDR2 containing the amino acid sequence as set forth in SEQ ID NO: 144, and heavy chain CDR3 containing the amino acid sequence as set forth in SEQ ID NO: 145, and a light chain variable region comprising light chain CDR1 containing the amino acid sequence as set forth in SEQ ID NO: 146, light chain CDR2 containing the amino acid sequence as set forth in SEQ ID NO: 147, and light chain CDR3 containing the amino acid sequence as set forth in SEQ ID NO: 148;

s. an antibody comprising a heavy chain variable region comprising heavy chain CDR1 containing the amino acid sequence as set forth in SEQ ID NO: 149, heavy chain CDR2 containing the amino acid sequence as set forth in SEQ ID NO: 150, and heavy chain CDR3 containing the amino acid sequence as set forth in SEQ ID NO: 151, and a light chain variable region comprising light chain CDR1 containing the amino acid sequence as set forth in SEQ ID NO: 152, light chain CDR2 containing the amino acid sequence as set forth in SEQ ID NO: 153, and light chain CDR3 containing the amino acid sequence as set forth in SEQ ID NO: 154;

t. an antibody comprising a heavy chain variable region comprising heavy chain CDR1 containing the amino acid sequence as set forth in SEQ ID NO: 155, heavy chain CDR2 containing the amino acid sequence as set forth in SEQ ID NO: 156, and heavy chain CDR3 containing the amino acid sequence as set forth in SEQ ID NO: 157, and a light chain variable region comprising light chain CDR1 containing the amino acid sequence as set forth in SEQ ID NO: 158, light chain CDR2 containing the amino acid sequence as set forth in SEQ ID NO: 159, and light chain CDR3 containing the amino acid sequence as set forth in SEQ ID NO: 160;

u. an antibody comprising a heavy chain variable region comprising heavy chain CDR1 containing the amino acid sequence as set forth in SEQ ID NO: 161, heavy chain CDR2 containing the amino acid sequence as set forth in SEQ ID NO: 162, and heavy chain CDR3 containing the amino acid sequence as set forth in SEQ ID NO: 163, and a light chain variable region comprising light chain CDR1 containing the amino acid sequence as set forth in SEQ ID NO: 164, light chain CDR2 containing the amino acid sequence as set forth in SEQ ID NO: 165, and light chain CDR3 containing the amino acid sequence as set forth in SEQ ID NO: 166;

v. an antibody comprising a heavy chain variable region comprising heavy chain CDR1 containing the amino acid sequence as set forth in SEQ ID NO: 167, heavy chain CDR2 containing the amino acid sequence as set forth in SEQ ID NO: 168, and heavy chain CDR3 containing the amino acid sequence as set forth in SEQ ID NO: 169, and a light chain variable region comprising light chain CDR1 containing the amino acid sequence as set forth in SEQ ID NO: 170, light chain CDR2 containing the amino acid sequence as set forth in SEQ ID NO: 171, and light chain CDR3 containing the amino acid sequence as set forth in SEQ ID NO: 172;
w. an antibody comprising a heavy chain variable region comprising heavy chain CDR1 containing the amino acid sequence as set forth in SEQ ID NO: 173, heavy chain CDR2 containing the amino acid sequence as set forth in SEQ ID NO: 174, and heavy chain CDR3 containing the amino acid sequence as set forth in SEQ ID NO: 175, and a light chain variable region comprising light chain CDR1 containing the amino acid sequence as set forth in SEQ ID NO: 176, light chain CDR2 containing the amino acid sequence as set forth in SEQ ID NO: 177, and light chain CDR3 containing the amino acid sequence as set forth in SEQ ID NO: 178;
x. an antibody comprising a heavy chain variable region comprising heavy chain CDR1 containing the amino acid sequence as set forth in SEQ ID NO: 179, heavy chain CDR2 containing the amino acid sequence as set forth in SEQ ID NO: 180, and heavy chain CDR3 containing the amino acid sequence as set forth in SEQ ID NO: 181, and a light chain variable region comprising light chain CDR1 containing the amino acid sequence as set forth in SEQ ID NO: 182, light chain CDR2 containing the amino acid sequence as set forth in SEQ ID NO: 183, and light chain CDR3 containing the amino acid sequence as set forth in SEQ ID NO: 184;
y. an antibody comprising a heavy chain variable region comprising heavy chain CDR1 containing the amino acid sequence as set forth in SEQ ID NO: 207, heavy chain CDR2 containing the amino acid sequence as set forth in SEQ ID NO: 208, and heavy chain CDR3 containing the amino acid sequence as set forth in SEQ ID NO: 209, and a light chain variable region comprising light chain CDR1 containing the amino acid sequence as set forth in SEQ ID NO: 210, light chain CDR2 containing the amino acid sequence as set forth in SEQ ID NO: 211, and light chain CDR3 containing the amino acid sequence as set forth in SEQ ID NO: 212;
z. an antibody comprising a heavy chain variable region comprising heavy chain CDR1 containing the amino acid sequence as set forth in SEQ ID NO: 213, heavy chain CDR2 containing the amino acid sequence as set forth in SEQ ID NO: 214, and heavy chain CDR3 containing the amino acid sequence as set forth in SEQ ID NO: 215, and a light chain variable region comprising light chain CDR1 containing the amino acid sequence as set forth in SEQ ID NO: 216, light chain CDR2 containing the amino acid sequence as set forth in SEQ ID NO: 217, and light chain CDR3 containing the amino acid sequence as set forth in SEQ ID NO: 218;
aa. an antibody comprising a heavy chain variable region comprising heavy chain CDR1 containing the amino acid sequence as set forth in SEQ ID NO: 213, heavy chain CDR2 containing the amino acid sequence as set forth in SEQ ID NO: 214, and heavy chain CDR3 containing the amino acid sequence as set forth in SEQ ID NO: 247, and a light chain variable region comprising light chain CDR1 containing the amino acid sequence as set forth in SEQ ID NO: 216, light chain CDR2 containing the amino acid sequence as set forth in SEQ ID NO: 217, and light chain CDR3 containing the amino acid sequence as set forth in SEQ ID NO: 218;
bb. an antibody comprising a heavy chain variable region comprising heavy chain CDR1 containing the amino acid sequence as set forth in SEQ ID NO: 219, heavy chain CDR2 containing the amino acid sequence as set forth in SEQ ID NO: 220, and heavy chain CDR3 containing the amino acid sequence as set forth in SEQ ID NO: 221, and a light chain variable region comprising light chain CDR1 containing the amino acid sequence as set forth in SEQ ID NO: 222, light chain CDR2 containing the amino acid sequence as set forth in SEQ ID NO: 223, and light chain CDR3 containing the amino acid sequence as set forth in SEQ ID NO: 224;
cc. an antibody comprising a heavy chain variable region comprising heavy chain CDR1 containing the amino acid sequence as set forth in SEQ ID NO: 225, heavy chain CDR2 containing the amino acid sequence as set forth in SEQ ID NO: 226, and heavy chain CDR3 containing the amino acid sequence as set forth in SEQ ID NO: 227, and a light chain variable region comprising light chain CDR1 containing the amino acid sequence as set forth in SEQ ID NO: 228, light chain CDR2 containing the amino acid sequence as set forth in SEQ ID NO: 229, and light chain CDR3 containing the amino acid sequence as set forth in SEQ ID NO: 230; and
dd. an antibody comprising a heavy chain variable region comprising heavy chain CDR1 containing the amino acid sequence as set forth in SEQ ID NO: 231, heavy chain CDR2 containing the amino acid sequence as set forth in SEQ ID NO: 232, and heavy chain CDR3 containing the amino acid sequence as set forth in SEQ ID NO: 233, and a light chain variable region comprising light chain CDR1 containing the amino acid sequence as set forth in SEQ ID NO: 234, light chain CDR2 containing the amino acid sequence as set forth in SEQ ID NO: 235, and light chain CDR3 containing the amino acid sequence as set forth in SEQ ID NO: 236.

9. The method of claim 8, wherein the CLDN18.2 expressing cancer is gastric, esophagus, pancreatic or liver cancer.

10. The method of claim 8, further comprising administering a chemotherapeutic agent to the subject.

11. The method of claim 10, wherein the chemotherapeutic agent is one or more of a nucleoside analog, a platinum compound, a camptothecin analog and a taxane.

12. The method of claim 10, wherein the chemotherapeutic agent is one or more of gemcitabine, 5-fluorouracil, capecitabine, oxaliplatin, irinotecan and paclitaxel.

13. The method of claim 10, wherein the chemotherapeutic agent is one or more of oxaliplatin and paclitaxel.

14. The method of claim 8, wherein the heavy chain and/or the light chain of the antibody is fused with one or more IL-2 polypeptides, one or more IL-2 analogs, one or more IL-15 polypeptides or one or more IL-15 analogs.

* * * * *